(12) United States Patent
McHugh

(10) Patent No.: US 10,719,579 B2
(45) Date of Patent: Jul. 21, 2020

(54) VALIDATING BIOMARKER MEASUREMENT

(71) Applicant: ImmuneXpress Pty Ltd, Boonah (AU)

(72) Inventor: Leo Charles McHugh, Seattle, WA (US)

(73) Assignee: IMMUNEXPRESS PTY LTD, Queensland (AU)

( * ) Notice: Subject to any disclaimer, the term of this patent is extended or adjusted under 35 U.S.C. 154(b) by 525 days.

(21) Appl. No.: 15/160,749

(22) Filed: May 20, 2016

(65) Prior Publication Data

US 2016/0350477 A1 Dec. 1, 2016

(30) Foreign Application Priority Data

May 28, 2015 (AU) .............................. 2015901982

(51) Int. Cl.
*G06F 19/20* (2011.01)

(52) U.S. Cl.
CPC .................................. *G06F 19/20* (2013.01)

(58) Field of Classification Search
CPC .......... G06F 19/20; C12Q 1/68; C12Q 1/6883
See application file for complete search history.

(56) References Cited

U.S. PATENT DOCUMENTS

| | | | | |
|---|---|---|---|---|
| 7,622,260 B2* | 11/2009 | Gordon | ................ | C12Q 1/6886 435/6.18 |
| 7,767,395 B2* | 8/2010 | Garrett | ................ | C12Q 1/6883 435/6.1 |
| 2003/0148339 A1 | 8/2003 | Samartzidou et al. | | |
| 2004/0180365 A1 | 9/2004 | David | | |
| 2006/0246495 A1* | 11/2006 | Garrett | ................ | C12Q 1/6883 435/6.1 |
| 2008/0213768 A1* | 9/2008 | Cai | ...................... | C12Q 1/6883 435/6.12 |
| 2010/0009370 A1 | 1/2010 | Sazuka et al. | | |
| 2010/0184608 A1 | 7/2010 | Russwurm et al. | | |
| 2011/0077931 A1* | 3/2011 | Grimes | ................ | G01N 33/574 703/11 |
| 2012/0176487 A1* | 7/2012 | Pinard | ................ | G06K 9/00127 348/79 |
| 2014/0037649 A1* | 2/2014 | Brandon | .............. | C12Q 1/6883 424/164.1 |
| 2015/0218640 A1 | 8/2015 | Brandon et al. | | |
| 2016/0237493 A1 | 8/2016 | Brandon et al. | | |
| 2017/0191129 A1 | 7/2017 | Brandon et al. | | |

FOREIGN PATENT DOCUMENTS

| | | | |
|---|---|---|---|
| EP | 2392668 A2 | 12/2011 | |
| WO | 2006023769 A2 | 3/2006 | |
| WO | 2011139901 A2 | 11/2011 | |
| WO | WO 2013152989 A2 * | 10/2013 | ....... G01N 33/57419 |
| WO | WO 2013153461 A2 * | 10/2013 | ......... G01N 33/6896 |

OTHER PUBLICATIONS

*Electric Power Group, LLC.* v. *Alstom S.A.*, United States Court of Appeals for the Federal Circuit, 2016, 1-12.*
Wang, E., RNA Amplification for Successful Gene Profiling Analysis, Journal of Translational Medicine, 2005, 3(28), 1-11. (Year: 2005).*
Vandesompele et al., Accurate Normalization of Real-Time Quantitative RT-PCR Data by Geometric Averaging of Multiple Internal Control Genes, Genome Biology, 2002, 3(7), 1-12. (Year: 2002).*
Duffy et al., Validation of New Cancer Biomarkers: A Position Statement from the European Group on Tumor Markers, 2015, 61(6), 809-820. (Year: 2015).*
Nygaard et al., Effects of mRNA Amplification on Gene Expression Ratios in cDNA Experiments Estimated by Analysis of Variance, BMC Genomics, 2003, 4(11), 1-13. (Year: 2003).*
Merker et al., "Design and Evaluation of a Real-Time PCR Assay for Quantification of JAK2 V617F and Wild-Type JAK2 Transcript Levels in the Clinical Laboratory," Journal of Molecular Diagnostics 12(1): 58-64, Jan. 2010.
Brazma, A., et al., "Minimum information about a microarray experiment (MIAME)—toward standards for microarray data." Nat Genet. (2001); 29(4): 365-371.
Bustin, S.A., et al., "The MIQE guidelines: minimum information for publication of quantitative real-time PCR experiments." Clin Chem. (2009); 55(4): 611-622. doi: 10.1373/clinchem.2008.112797. Epub Feb. 26, 2009.
Comak, E., et al., "A new medical decision making system: Least square support vector machine (LSSVM) with Fuzzy Weighting Pre-processing." Expert Systems with Applications (2007); 32(2): 409-414.
Fardin, P., et al., "Normalization of low-density microarray using external spike-in controls: analysis of macrophage cell lines expression profile." BMC Genomics (2007); 8: 17. http://doi.org/10.1186/1471-2164-8-17.
Irizarry, R.A., et al., "Exploration, normalization, and summaries of high density oligonucleotide array probe level data." Biostatistics (2003); 4(2): 249-264.
Jiang, L., et al., "Synthetic spike-in standards for RNA-seq experiments." Genome Res. (2011); 21(9): 1543-1551. doi: 10.1101/gr.121095.111. Epub Aug. 4, 2011.
Levy, M.M., et al., "2001 SCCM/ESICM/ACCP/ATS/SIS International Sepsis Definitions Conference." Intensive Care Med. (2003); 29(4): 530-538. Epub Mar. 28, 2003.
Perkel, J.M., "Overcoming the Challenges of Multiplex PCR." Biocompare, Oct. 23, 2012, 5 pages, Downloaded Dec. 15, 2016, http://www.biocompare.com/Editorial-Articles/117895-Multiplex-PCR/.

(Continued)

*Primary Examiner* — Amy M Bunker

(57) ABSTRACT

A method for validating quantification of biomarkers, the biomarkers being quantified using a quantification technique of a selected type, and the method including determining a plurality of biomarker values, each biomarker value being indicative of a value measured or derived from a measured value, for at least one corresponding biomarker of the biological subject and being at least partially indicative of a concentration of the biomarker in a sample taken from the subject, determining at least one control value by determining a combination of biomarker values, comparing each control value to a respective control reference and determining if the biomarker values are valid using results of the comparison.

15 Claims, 21 Drawing Sheets

(56) References Cited

OTHER PUBLICATIONS

Rangel-Frausto, M.S., et al., "The natural history of the systemic inflammatory response syndrome (SIRS). A prospective study." JAMA (1995); ;273(2): 117-123.

Reinhart, K., et al., "New Approaches to Sepsis: Molecular Diagnostics and Biomarkers." Clin Microbiol Rev. (2012); 25(4): 609-634. doi: 0.1128/CMR.00016-12.

Vandesompele, J., et al., "Accurate normalization of real-time quantitative RT-PCR data by geometric averaging of multiple internal control genes." Genome Biol. (2002); 3(7):RESEARCH0034. Epub Jun. 18, 2002.

Benjamini, Y., and Hochberg, Y. "Controlling the false discovery rate: a practical and powerful approach to multiple testing", Journal of the Royal Statistical Society Series B (Methodological) (1995); 57(1): 289-300.

Biagini, R. E., et al. "Rapid, Sensitive, and Specific Lateral-Flow Immunochromatographic Device to Measure Anti-Anthrax Protective Antigen Immunoglobulin G in Serum and Whole Blood", Clinical and Vaccine Immunology (2006); 13(5): 541-546.

Fahy, E., et al. "Update of the LIPID Maps comprehensive classification system for lipids", The Journal of Lipid Research (2009); 50(Supplement), S9-S14.

Fraser, J., et al. "Chromatin conformation signatures of cellular differentiation", Genome Biology (2009); 10(4): R37.

Gaydos, C. A., et al., "Use of ligase chain reaction with urine versus cervical culture for detection of Chlamydia trachomatis in an asymptomatic military population of pregnant and nonpregnant females attending Papanicolaou smear clinics", Journal of Clinical Microbiology (1998); 36(5): 1300-1304.

Gerber, S. A., et al., "Absolute quantification of proteins and phosphoproteins from cell lysates by tandem MS", Proceedings of the National Academy of Sciences (2003); 100(12): 6940-6945.

Harris, R. A, et al., "Comparison of sequencing-based methods to profile DNA methylation and identification of monoallelic epigenetic modifications", Nature Biotechnology (2010); 28(10): 1097-1105.

Ho, Yen-Peng and Reddy, P.M., "Identification of Pathogens by Mass Spectrometry", Clinical Chemistry (2010); 56(4): 525-536—doi:10.1373/clinchem.2009.138867.

Jothi et al., "Genome-wide identification of in vivo protein—DNA binding sites from ChIP-seq data", Nucleic Acids Research (2008); 36(16): 5221-5231.

Levy, M.M., et al., "2001 SCCM/ESICM/ACCP/ATS/SIS International Sepsis Definitions Conference", Critical Care Medicine (2003); 31(4): 1250-1256.

Li, C., et al., "Development of a robust flow cytometry-based pharmacodynamic assay to detect phospho-protein signals for phosphatidylinositol 3-kinase inhibitors in multiple myeloma", Journal of Translational Medicine (2013); 11(1): 76.

Martins, T. B., "Development of Internal Controls for the Luminex Instrument as Part of a Multiplex Seven-Analyte Viral Respiratory Antibody Profile", Clinical and Vaccine Immunology (2002); 9(1): 41-45.

Ritchie, G., et al., "Identification of N-linked carbohydrates from severe acute respiratory syndrome (SARS) spike glycoprotein", Virology (2010); 399(2): 257-269.

Roche Applied Science Technical Note No. LC15/2002, Roche Diagnostics GmbH (2002) 20 pages.

Xu, H., et al., "A signal-noise model for significance analysis of ChIPseq with negative control", Bioinformatics (2010); 26(9): 1199-1204.

* cited by examiner

VALIDATING BIOMARKER MEASUREMENT

CROSS REFERENCE TO RELATED APPLICATION

This application claims priority to Australian Application No. 2015901982, filed on May 28, 2015, which is incorporated herein by reference in its entirety.

BACKGROUND OF THE INVENTION

The present invention relates to a method and apparatus for validating measurement of biomarker values used in generating an indicator, and in one example, to a method and apparatus for validating an indicator used in determining the likelihood of a biological subject having at least one medical condition.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

Measurement of gene expression (as RNA or protein) in samples taken from living organisms has practical applications including, but not limited to, determining a disease state, determining disease extent or severity, disease prognosis and early identification, identifying a tissue type (both normal and diseased including cancers), identifying and enumerating cell types in a cell mix, and understanding normal metabolic processes and their response to external factors or insults (including injury, wounds, burns, stress, viral or bacterial or parasitic or fungal infection, exercise, diet, therapeutics, toxins, therapies, treatments and experimental procedures). There are a number of methods available for measuring gene expression (as RNA or protein) that are well known in the art, from low-throughput (single genes and gene products) to high-throughput (exome and arrays), including northern blots, polymerase chain reaction (qPCR), microarrays, RNA sequencing (RNA-seq), targeted RNA sequencing, ELISA, EIA, mass spectrometry, HPLC, SNP analysis, and epigenetic technologies (ChIP-Seq, Chromatin Conformational Signatures (CCA), DNA methylation analyses).

Each of these technologies produces a value, or a set of values for each of the products measured. In the context of medical discovery and its applications, these values are termed 'biomarkers'. A measured value for any gene expression product (as RNA or protein) is defined as a measured biomarker, as measured by the processing instrument or device. Examples of a measured biomarker include a protein concentration for a specified protein, the transcript count for a single transcript in the case of RNA sequencing, the expression value for an exon or transcript in the case of microarrays, an m/z value in the case of mass spectrometry or a fluorescence value in the case of flow cytometry. Measured biomarkers can be understood as 'raw data', as measured by the instrument. Multi-biomarker assays will measure a number of biomarkers in parallel, reporting a collection of measured biomarkers.

Indicator values are values that are designed to correlate, classify, or otherwise be indicative of some condition, stage, diagnosis or prognosis or absence thereof. For example temperature reported in degrees is an indicator value for fever. Arbitrarily complex indicators may be built for any purpose, and in the case of multi-biomarker medical devices, the indicator will be some combination of biomarkers that, through an equation, generate an indicator value that correlates to some state or condition (or the absence of such) for a patient.

The development and use of indicator values requires accurate and valid measurement of gene expression (as RNA or protein) measured values, and can be achieved through the use of two key steps: normalisation and controls. Controls provide a check that the underlying values are valid, and normalisation is any method by which samples can be made comparable by removing non-biological sources of variation between samples.

Controls are used to ensure that relevant potential modes of failure can be detected. If a failure is detected in a control, the assay or experiment can be declared failed and the indicator value (if any) will consequently also be invalid. In the context of medical devices, controls guard against the results of the test (indicator values) being reported when the underlying inputs to the indicator may be invalid thus avoiding the potential of the operator drawing false conclusions. Controls that can be used include the following (which ones used depends in part upon the user, the application and the stage of development of the assay):

- No template control (run in parallel with other reactions to determine the extent of contamination—for PCR)
- No amplification control for assays relying on nucleic acid amplification (e.g., contains no polymerase—this checks for example the integrity of a labelled probe relying on the FRET principle—for PCR)
- Positive control (a sample used during assay use to confirm that the test is able to produce a result in the reportable range). This does not imply that the reported value for this control will be above a given threshold (for example positive for a disease), merely that the control is positively able to generate a value in the reportable range of the test. Positive controls may be biological in origin or synthetic (or a hybrid of the two, such as recombinant products), and the positive controls can be internal (coming from within a sample being tested) or external (run in parallel and independent of the sample being tested). Positive controls can include positive or negative biological or synthetic controls.
- A control containing no reverse transcriptase (to determine the extent of contaminating DNA especially if primers are not designed across an exon/intron border—for PCR)
- Spike-in controls include artificial nucleic acid added to either the sample to be tested (at any stage) and are used to determine the extent of PCR inhibition and for quality control in array and RNA-seq (for quantification, sensitivity, coverage and linearity).

Of these measured controls perhaps the most common are external positive controls containing known concentrations of a given analyte, and spike-ins. The use of such controls contributes to the expense and complexity of running an experiment, or assay, through having to purchase reagents and the controls themselves, through the use of experimental "real estate" which could otherwise be used for targets, and in the additional resources and complexity inherent in having these control targets in addition to the targets required to produce the indicator value. It is therefore advantageous to reduce the additional measured controls not measured in the course of determining the indictor value.

Normalisation is an important step that ensures that comparisons between samples, or between a reference and a sample can be made. The objective of the normalisation step is to remove differences not attributable to biological variability, such as batch effect and other sources of technical variability including those introduced by concentration, time, temperature, instruments, operators or assay parameters (including those unknown or outside of the control of the assay users) such as those introduced in a typical workflow, such as that described below.

Measurement of gene expression using microarrays or PCR or RNA-seq by example usually involves some or all of the following steps depending on the method (similar types of controls are required in most experiments measuring biomarkers):

Experimental design including power calculation and number of replicates to be used
Isolation of RNA or mRNA from sample(s) of interest
Determination of RNA quality and quantity
Fragmentation and size selection (for RNA-seq)
Conversion of RNA to complementary DNA (cDNA)
Conversion of cDNA to cRNA (for certain microarrays)
Fragmentation and labelling (for arrays, or use of a labelled probe for PCR)
Detection
Data capture
Determination of data quality
Data normalisation
Control for false discovery.

Some of the experimental method variables that need to be controlled for (normalized) are detailed in Table 1 below, adapted from Roche Applied Science Technical Note No. LC15/2002, under the appropriate step.

TABLE 1

| Sample | | | | |
| --- | --- | --- | --- | --- |
| | DNA/RNA cDNA | | | |
| Sample Preparation | Nucleic acid isolation | Reverse transcription | Product | |
| | | | Amplification | Detection |
| Preparation method Stability of nucleic acid Storage | Isolation method Purity Variability of isolation Storage | Efficiency Enzyme variability | Efficiency Enzyme variability | Method used Linearity of assay |

So that datasets can be compared, and that publicly available data is of high quality, minimum information guidelines for gene expression analysis experiments have been published in scientific journals for both PCR and microarrays (Bustin S A, Benes V, Garson J A, Hellemans J, Huggett J, et al. (2009) The MIQE Guidelines: Minimum Information for Publication of Quantitative Real-Time PCR Experiments. Clinical Chemistry 55: 611-622) (Brazma A, Hingamp P, Quackenbush J, Sherlock G, Spellman P, et al. (2001) Minimum information about a microarray experiment (MIAME)-toward standards for microarray data. Nat Genet 29: 365-371) and are publicly available for RNA-seq (MINSEQE—www.mged.org/minseqe/).

Normalisation of data to account for these effects using measured biomarkers is common. For example, an external positive control at a known concentration may be run in parallel with a sample. The value of the measured biomarker value in the sample can then be inferred (normalized) with reference to the measured external positive control. This is the concept behind a standard calibration curve used for normalisation. Another common normalisation method using measured biomarkers uses internal positive controls; for example, in an RNA sequencing experiment, certain genes (or groups of genes) may be assumed to have a constant biological level of expression (these are the normalizer biomarkers). Differences in the measured values for these normalizer biomarkers between samples is then assumed to be non-biological. The measured values for each sample are then adjusted up or down such that the normalizer biomarkers in each sample have the same value and the data is then said to be normalized. The normalized values of each biomarker may then be directly compared between samples, for example for the diagnosis of a medical condition. Extensions of this concept are also known, for example Robust Microarray Analysis (Irizarry, R A; Hobbs, B; Collin, F; Beazer-Barclay, Y D; Antonellis, K J; Scherf, U; Speed, T P (2003). "Exploration, normalisation, and summaries of high density oligonucleotide array probe level data.". *Biostatistics* 4 (2): 249-64) where the measured values for each sample are adjusted such that the normalized values for each sample fit the same distribution.

In practice, microarrays and RNA-seq and other platforms are often used in the early "discovery" or research stage of experimentation to generate sets of measured biomarkers covering the exome or genome or regulatory mechanisms thereof. The set of measured biomarkers generated in such discovery experiments may be upwards of 6,000 genes or transcripts, or up to 1,000,000 peaks in the case of tandem mass spectrometry discovery datasets. There are typically many more measured biomarkers in each dataset than patient samples. This leads directly to false discovery problems as will be appreciated by someone skilled in the art of biomarker discovery. A false discovery is when a measured biomarker with no genuine biological correlation to the condition under consideration by chance happens to correlate to said condition. These false discoveries are indistinguishable from true discoveries until more patient samples have been tested.

Once certain biomarkers have been "discovered", or shown to be significantly correlated to the desired experimental endpoint, a minimal set of biomarkers is often migrated to an appropriate clinical device, such as qPCR or Point-Of-Care RNA-sequencing platforms, along with a minimal set of appropriate controls.

qPCR currently has significant and commercially attractive advantages over microarrays and RNA-seq (including targeted RNA-seq), especially when used in a clinical environment. Such advantages include fast turnaround time, limited technician hands-on-time to set up an assay, limited technical skill level required to run an assay, accessibility and availability of PCR machines, small footprint of PCR machines, ease of results interpretation, limited need for supporting information technology infrastructure (software, algorithms, hardware, networks), limited license fees, availability and cost of reagents. Such factors lead to reduced cost of goods sold and a higher likelihood of market acceptance of an assay.

The successful migration of relevant biomarkers to qPCR is currently limited by a number of factors including:
Limited multiplexing capability
Limited reporter dyes (with non-overlapping emission spectra or with good spectral resolution)
The need for positive controls and spike-ins
The need to run a passive reference dye
Cost of spike-in controls
Cost and added complexity of controls, especially external controls
Sample prep limitations.

Such factors generally limit multiplex qPCR to two to four targets at the maximum since up to three dyes are used as controls (passive reference, internal, spike-in).

Thus, for cost and practical reasons, there is a need for a better control strategy in gene expression analysis, and in particular one tailored for use in medical devices.

Prior art practices in the design and use of controls in gene expression analyses is limited and is generally based on variations on the themes of the use of spike-ins (artificial sequences and naturally occurring sequences) and internal measured controls. For example, Vandesompele et al., (2002) (Vandesompele J, De Preter K, Pattyn F, Poppe B, Van Roy N, et al. (2002) Accurate normalisation of real-time quantitative RT-PCR data by geometric averaging of multiple internal control genes. Genome Biol 3: RESEARCH0034) describe the use of multiple internal control genes (a collection of measured biomarkers), rather than just a single internal control gene, and a method of identifying stably expressed genes in different tissues for the use of tissue-specific internal control genes. The authors suggest that different tissues may require the use of different internal control genes and that the use of more than one internal control gene provides more consistent results with respect to normalisation. Prior to this publication it was generally accepted that a single gene was sufficient for normalisation and that the genes GAPDH, beta-2 microglobulin or 18S ribosomal were stably expressed across all tissues and all conditions, which has since been proven to be incorrect, especially in conditions that have a large effect on gene expression, such as peripheral blood gene expression in sepsis.

Fardin et al., (2007) (Fardin P, Moretti S, Biasotti B, Ricciardi A, Bonassi S, et al. (2007) Normalisation of low-density microarray using external spike-in controls: analysis of macrophage cell lines expression profile. BMC Genomics 8: 17. doi:10.1186/1471-2164-8-17) describe the use of artificial spike-in RNAs as a method of providing more consistent normalisation for low density array qPCR data, especially when the distribution of up- and down-regulated genes is asymmetric. Similarly, Jiang et al., (2011) (Jiang L, Schlesinger F, Davis C A, Zhang Y, Li R, et al. (2011) Synthetic spike-in standards for RNA-seq experiments. Genome Res 21: 1543-1551. doi:10.1101/gr.121095.111) describe synthetic RNA spike-in controls for use in RNA-seq experiments.

Various published patents describe the use of internal control genes (measured biomarkers) specifically for blood (EP2392668A2, US20100184608) or artificial universal spike-in (external) controls for use with any tissue type (US20030148339).

In the patent entitled "Diagnostic and Prognostic Tests" (U.S. Pat. No. 7,622,260) the inventors describe an approach using ratios of gene expression to diagnose biological states or conditions, in particular cancer, and for distinguishing malignant pleural mesothelioma from other lung cancers or from normal lung tissue, and for distinguishing between subclasses of malignant pleural mesothelioma.

SUMMARY OF THE PRESENT INVENTION

In one broad form the present invention seeks to provide a method for validating quantification of biomarkers, the biomarkers being quantified using a quantification technique of a selected type, and the method including:
  a) determining a plurality of biomarker values, each biomarker value being indicative of a value measured or derived from a measured value, for at least one corresponding biomarker of the biological subject and being at least partially indicative of a concentration of the biomarker in a sample taken from the subject;
  b) determining at least one control value by determining a combination of biomarker values;
  c) comparing each control value to a respective control reference; and,
  d) determining if the biomarker values are valid using results of the comparison.

Typically at least first and second biomarker values are used to determine an indicator indicative of a test result, and wherein the method includes determining control values including:
  a) a combination of the first and at least one other biomarker value; and,
  b) a combination of the second and at least one other biomarker value.

Typically the method includes:
  a) determining at least four biomarker values, the indicator being based on a combination of:
    i) a first indicator value calculated using first and second biomarker values; and,
    ii) a second indicator value calculated using third and fourth biomarker values; and,
  b) determining control values including:
    i) a first control value calculated using first and third biomarker values;
    ii) a second control value calculated using first and fourth biomarker values;
    iii) a third control value calculated using second and third biomarker values; and,
    iv) a fourth control value calculated using second and fourth biomarker values.

Typically the method includes determining control values including:
  a) a fifth control value calculated using first and second biomarker values;
  b) a sixth control value calculated using third and fourth biomarker values; and,
  c) control values calculated using a combination of measured biomarkers not used in determining an indicator value.

Typically the method includes calculating at least one of the indicator values and the control values by applying a function to the respective biomarker values.

Typically the function includes at least one of:
  a) multiplying two biomarker values;
  b) dividing two biomarker values;
  c) a ratio of two biomarker values;
  d) adding two biomarker values;
  e) subtracting two biomarker values;
  f) a weighted sum of at least two biomarker values;
  g) a log sum of at least two biomarker values; and,
  h) a sigmoidal function of at least two biomarker values.

Typically the method includes determining:
  a) a first control value using a ratio of first and third biomarker values;
  b) a second control value using a ratio of first and fourth biomarker values;
  c) a third control value using a ratio of second and third biomarker values; and,
  d) a fourth control value using a ratio of second and fourth biomarker values.

Typically the method includes determining control values including:
  a) a fifth control value using a ratio of first and second biomarker values;
  b) a sixth control value using a ratio of third and fourth biomarker values; and, c) controls values calculated using a ratio of measured biomarkers not used in determining an indicator value.

Typically the method includes:
a) determining a validity probability based on the result of the comparison; and,
b) using the validity probability to determine if the biomarker values are valid.

Typically the method includes:
a) determining a control value probability for the comparison of each control value to the respective control reference; and,
b) combining the control value probabilities to determine the validity probability.

Typically the control reference is at least one of:
a) a control value threshold range;
b) a control value threshold; and,
c) a control value distribution.

Typically the control reference is a control value threshold range, and wherein the method includes:
a) comparing each control value to a respective control value threshold range; and,
b) determining at least one of the biomarker values to be invalid if any one of the control values falls outside the respective control value threshold range.

Typically the control reference is a control value distribution, and wherein the method includes:
a) comparing each control value to a respective control value distribution; and,
b) determining the validity using the results of the comparisons.

Typically each respective reference is derived from biomarker values collected from a number of individuals in a sample population.

Typically each respective reference is determined for at least part of the sample population.

Typically the sample population includes:
a) a plurality of individuals of different sexes;
b) a plurality of individuals of different ethnicities;
c) a plurality of healthy individuals;
d) a plurality of individuals suffering from at least one diagnosed medical condition;
e) a plurality of individuals showing clinical signs of at least one medical condition; and,
f) first and second groups of individuals, each group of individuals suffering from a respective diagnosed medical condition.

Typically the indicator is for use in determining the likelihood that a biological subject has at least one medical condition, and wherein the sample population includes:
a) individuals presenting with clinical signs of the at least one medical condition;
b) individuals diagnosed with the at least one medical condition; and,
c) healthy individuals.

Typically the indicator is determined by combining the first and second derived indicator values using a combining function, the combining function being at least one of:
a) an additive model;
b) a linear model;
c) a support vector machine;
d) a neural network model;
e) a random forest model;
f) a regression model;
g) a genetic algorithm;
h) an annealing algorithm;
i) a weighted sum; and,
j) A nearest neighbour model.

Typically the method includes:
a) determining an indicator value;
b) comparing the indicator value to at least one indicator value range; and,
c) determining the indicator at least in part using a result of the comparison.

Typically the indicator is indicative of a likelihood of the subject having at least one medical condition.

Typically the method includes generating a representation of the indicator.

Typically the representation includes:
a) an alphanumeric indication of the indicator value;
b) a graphical indication of a comparison of the indicator value to one or more thresholds; and,
c) an alphanumeric indication of a likelihood of the subject having at least one medical condition.

Typically the biomarker value is indicative of a level or abundance of a molecule, cell or organism selected from one or more of:
a) proteins;
b) nucleic acids;
c) carbohydrates;
d) lipids;
e) proteoglycans;
f) cells;
g) metabolites;
h) tissue sections;
i) whole organisms; and,
j) molecular complexes.

Typically the method is performed at least in part using one or more electronic processing devices.

Typically the indicator reference is retrieved from a database.

Typically the method includes, in the one or more electronic processing devices:
a) receiving the biomarker values;
b) determining the at least one control value using at least two of the biomarker values;
c) comparing the at least one control value to the respective control value threshold; and,
d) determining if the test is a valid test using the results of the comparison.

Typically the method includes, in the one or more electronic processing devices:
a) determining the indicator by:
  i) calculating a first indicator value using a ratio of first and second biomarker values;
  ii) calculating a second indicator value using a ratio of third and fourth second biomarker values; and,
  iii) determining a sum of the first and second indicator values;
b) determining a plurality of control values by:
  i) calculating a first control value using a ratio of the first and third biomarker values;
  ii) calculating a second control value using a ratio of the first and fourth biomarker values;
  iii) calculating a third control value using a ratio of the second and third biomarker values; and,
  iv) calculating a fourth control value using a ratio of the second and fourth biomarker values;
c) comparing each control value to a respective threshold range; and,
d) displaying the indicator in response to a successful comparison for each control value.

Typically the method includes, in the one or more electronic processing devices:
a) calculating a fifth control value using a ratio of the first and second biomarker values;
b) calculating a sixth control value using a ratio of the third and fourth biomarker values; and,
c) calculating an additional or set of control values by using a combination of biomarkers not used in determining an indicator value.

Typically the biomarkers are gene expression products and wherein the method includes:
a) obtaining a sample from a biological subject, the sample including the gene expression products;
b) amplifying at least the gene expression products in the sample; and,
c) for each gene expression product, determining an amplification amount representing a degree of amplification required to obtain a defined level of the respective gene expression.

Typically the amplification amount is at least one of:
a) a cycle time;
b) a number of cycles;
c) a cycle threshold; and,
d) an amplification time.

Typically the biomarkers are gene expression products and wherein the method includes, determining a combination of biomarker values by subtracting amplification amounts for the respective gene expression products so that the combination of biomarker values represents a ratio of the relative concentration of the respective gene expression products.

Typically the biomarker values are obtained from a biological subject presenting with clinical signs of at least one medical condition.

Typically the at least one condition includes ipSIRS (infection positive Systemic Inflammatory Response Syndrome) and wherein the biomarker values correspond to relative concentrations of LAMP1, CEACAM4, PLAC8 and PLA2G7.

Typically the biomarker values are obtained from a biological subject presenting with clinical signs common to first and second conditions and wherein the indicator is for use in distinguishing between the first and second conditions.

Typically the first and second conditions include inSIRS (infection negative Systemic Inflammatory Response Syndrome) and ipSIRS.

Typically the quantification technique is at least one of:
a) a nucleic acid amplification technique;
b) polymerase chain reaction (PCR);
c) a hybridisation technique;
d) microarray analysis;
e) low density arrays;
f) hybridisation with allele-specific probes;
g) enzymatic mutation detection;
h) ligation chain reaction (LCR);
i) oligonucleotide ligation assay (OLA);
j) flow-cytometric heteroduplex analysis;
k) chemical cleavage of mismatches;
l) mass spectrometry;
m) flow cytometry;
n) liquid chromatography;
o) gas chromatography;
p) immunohistochemistry;
q) nucleic acid sequencing;
r) single strand conformation polymorphism (SSCP);
s) denaturing gradient gel electrophoresis (DGGE);
t) temperature gradient gel electrophoresis (TGGE);
u) restriction fragment polymorphisms;
v) serial analysis of gene expression (SAGE);
w) affinity assays;
x) radioimmunoassay (RIA);
y) lateral flow immunochromatography;
z) flow cytometry;
aa) electron microscopy (EM); and,
bb) enzyme-substrate assay.

In one broad form the present invention seeks to provide apparatus for validating measurement of biomarker values used in generating an indicator, the biomarkers being quantified using a quantification technique of a selected type, and the apparatus including at least one processing device that:
a) determines a plurality of biomarker values, each biomarker value being indicative of a value measured or derived from a measured value, for at least one corresponding biomarker of the biological subject and being at least partially indicative of a concentration of the biomarker in a sample taken from the subject;
b) determines at least one control value by determining a combination of biomarker values;
c) compares each control value to a respective control reference; and,
d) determines if the biomarker values are valid using results of the comparison.

In one broad form the present invention seeks to provide a method for validating an indicator used in determining the likelihood of a biological subject having at least one medical condition, the biomarkers being quantified using a quantification technique of a selected type and the method including:
a) determining a plurality of biomarker values, each biomarker value being indicative of a value measured or derived for at least one corresponding biomarker of the biological subject;
b) determining an indicator indicative of the likelihood of a biological subject having at least one medical condition by:
i) calculating a first indicator value using first and second biomarker values;
ii) calculating a second indicator value using third and fourth second biomarker values; and,
iii) determining the indicator using the first and second indicator values;
c) calculating at least one of:
i) a first control value using the first and third biomarker values;
ii) a second control value using the first and fourth biomarker values;
iii) a third control value using the second and third biomarker values;
iv) a fourth control value using the second and fourth biomarker values;
v) a fifth control value using the first and fourth second values;
vi) a sixth control value using the third and fourth biomarker values; and,
vii) an additional or set of control values by using a combination of biomarkers not used in determining an indicator value;
d) comparing the at least one control value to a respective control value threshold; and,
e) selectively validating the indicator using the results of the comparison.

In one broad form the present invention seeks to provide apparatus for validating an indicator indicative of measured values of gene expression products, the biomarkers being quantified using a quantification technique of a selected type, the apparatus including at least one processing device that:
  a) determines a plurality of biomarker values, each biomarker value being indicative of a value measured or derived for at least one corresponding biomarker of the biological subject;
  b) determines the indicator by:
    i) calculating a first indicator value using first and second biomarker values;
    ii) calculating a second indicator value using third and fourth second biomarker values; and,
    iii) determining the indicator using the first and second indicator values;
  c) calculates at least one of:
    i) a first control value using the first and third biomarker values;
    ii) a second control value using the first and fourth biomarker values;
    iii) a third control value using the second and third biomarker values;
    iv) a fourth control value using the second and fourth biomarker values;
    v) a fifth control value using the first and second biomarker values;
    vi) a sixth control value using the third and fourth biomarker values; and,
    vii) an additional or set of control values by using a combination of biomarkers not used in determining an indicator value.
  d) compares the at least one control value to a respective control value threshold; and,
  e) selectively validates the indicator using the results of the comparison.

In one broad form the present invention seeks to provide a method for validating an indicator used in determining the likelihood of a biological subject having at least one medical condition, the biomarkers being quantified using a quantification technique of a selected type and the method including:
  a) obtaining a sample from a biological subject, the sample including gene expression products;
  b) quantifying at least some gene expression products in the sample to determine a concentration of the gene expression product in the sample;
  c) determining an indicator indicative of the likelihood of a biological subject having at least one medical condition by combining:
    i) a first indicator value indicative of a ratio of the concentration of the first and second gene expression products; and,
    ii) a second indicator value indicative of a ratio of the concentration of the third and fourth gene expression products;
  d) determining control values by determining at least one of:
    i) a first control value indicative of a ratio of the concentration of the first and third gene expression products;
    ii) a second control value indicative of a ratio of the concentration of the first and fourth gene expression products;
    iii) a third control value indicative of a ratio of the concentration of the second and third gene expression products;
    iv) a fourth control value indicative of a ratio of the concentration of the second and fourth gene expression products;
    v) a fifth control value indicative of a ratio of the concentration of the first and second gene expression products;
    vi) a sixth control value indicative of a ratio of the concentration of the third and fourth gene expression products; and,
    vii) an additional or set of control values by using a combination of gene expression products not used in determining an indicator value;
  e) comparing each control value to a respective control value threshold range; and,
  f) validating the indicator if each of the control values is within the respective control value range.

Typically the method includes quantifying the concentration of the gene expression products by:
  a) amplifying at least some gene expression products in the sample; and,
  b) for each of a plurality of gene expression products, determining an amplification amount representing a degree of amplification required to obtain a defined level of the respective gene expression product.

Typically the method includes:
  a) determining the indicator by:
    i) determining a first indicator value calculated using the first and second amplification times indicative of the concentration of first and second gene expression products; and,
    ii) a second indicator value calculated using third and fourth amplification times indicative of the relative concentration of third and fourth gene expression products; and,
  b) determining control values by determining at least one of:
    i) a first control value calculated using first and third amplification times indicative of the relative concentration of first and third gene expression products;
    ii) a second control value calculated using first and fourth amplification times indicative of the relative concentration of first and fourth gene expression products;
    iii) a third control value calculated using second and third amplification times indicative of the relative concentration of second and third gene expression products;
    iv) a fourth control value calculated using second and fourth amplification times indicative of the relative concentration of second and fourth gene expression products;
    v) a fifth control value calculated using first and second amplification times indicative of the relative concentration of first and second gene expression products;
    vi) a sixth control value calculated using third and fourth amplification times indicative of the relative concentration of third and fourth gene expression products; and
    vii) an additional or set of control values by using a combination of amplification times not used in determining an indicator value.

In one broad form the present invention seeks to provide apparatus for validating an indicator used in determining the likelihood of a biological subject having at least one medical condition, the apparatus including:

a) a sampling device that obtains a sample from a biological subject, the sample including gene expression products;
b) a quantification device that quantifies at least some gene expression products in the sample to determine a concentration of the gene expression product in the sample; and,
c) at least one processing device that:
   i) determines an indicator indicative of the likelihood of a biological subject having at least one medical condition by combining:
      (1) a first indicator value indicative of a ratio of the concentration of the first and second gene expression products; and,
      (2) a second indicator value indicative of a ratio of the concentration of the third and fourth gene expression products;
   ii) determines control values by determining at least one of:
      (1) a first control value indicative of a ratio of the concentration of the first and third gene expression products;
      (2) a second control value indicative of a ratio of the concentration of the first and fourth gene expression products;
      (3) a third control value indicative of a ratio of the concentration of the second and third gene expression products;
      (4) a fourth control value indicative of a ratio of the concentration of the second and fourth gene expression products;
      (5) a fifth control value indicative of a ratio of the concentration of the first and second gene expression products;
      (6) a sixth control value indicative of a ratio of the concentration of the third and fourth gene expression products; and,
      (7) an additional or set of control values indicative of a ratio of the concentration of biomarkers not used in determining an indicator value;
   iii) compares each control value to a respective control value threshold range; and,
   iv) validates the indicator if each of the control values is within the respective control value range.

In one broad form the present invention seeks to provide a method for validating quantification of biomarkers, the method including:
a) determining a plurality of biomarker values, each biomarker value being indicative of a value measured or derived from a measured value, for at least one corresponding biomarker of the biological subject and being at least partially indicative of a concentration of the biomarker in a sample taken from the subject;
b) determining at least one control value by determining a combination of biomarker values;
c) comparing each control value to a respective control reference; and,
d) determining if the biomarker values are valid using results of the comparison, wherein the biomarker value is indicative of a level or abundance of a molecule, cell or organism selected from one or more of:
   i) proteins;
   ii) nucleic acids;
   iii) carbohydrates;
   iv) lipids;
   v) proteoglycans;
   vi) cells; and,
   vii) pathogenic organisms.

In one broad form the present invention seeks to provide a method for validating quantification of biomarkers, the method including:
a) determining a plurality of biomarker values, each biomarker value being indicative of a value measured or derived from a measured value, for at least one corresponding biomarker of the biological subject and being at least partially indicative of a concentration of the biomarker in a sample taken from the subject;
b) determining at least one control value by determining a combination of biomarker values;
c) comparing each control value to a respective control reference; and,
d) determining if the biomarker values are valid using results of the comparison, wherein the biomarker value is indicative of a level or abundance of a molecule, cell or organism selected from one or more of:
   i) proteins;
   ii) nucleic acids;
   iii) carbohydrates;
   iv) lipids;
   v) proteoglycans;
   vi) cells;
   vii) metabolites;
   viii) tissue sections;
   ix) whole organisms; and,
   x) molecular complexes.

In one broad form the present invention seeks to provide a method for validating quantification of biomarkers, the method including:
a) determining a plurality of biomarker values, each biomarker value being indicative of a value measured or derived from a measured value, for at least one corresponding biomarker of the biological subject and being at least partially indicative of a concentration of the biomarker in a sample taken from the subject;
b) determining at least one control value by determining a combination of biomarker values;
c) comparing each control value to a respective control reference; and,
d) determining if the biomarker values are valid using results of the comparison, wherein the biomarkers are quantified using at least one of:
   i) a nucleic acid amplification technique;
   ii) polymerase chain reaction (PCR);
   iii) a hybridisation technique;
   iv) microarray analysis;
   v) low density arrays;
   vi) hybridisation with allele-specific probes;
   vii) enzymatic mutation detection;
   viii) ligation chain reaction (LCR);
   ix) oligonucleotide ligation assay (OLA);
   x) flow-cytometric heteroduplex analysis;
   xi) chemical cleavage of mismatches;
   xii) mass spectrometry;
   xiii) flow cytometry;
   xiv) liquid chromatography;
   xv) gas chromatography;
   xvi) immunohistochemistry;
   xvii) nucleic acid sequencing;
   xviii) single strand conformation polymorphism (SSCP);
   xix) denaturing gradient gel electrophoresis (DGGE);
   xx) temperature gradient gel electrophoresis (TGGE);
   xxi) restriction fragment polymorphisms;
   xxii) serial analysis of gene expression (SAGE);
   xxiii) affinity assays;

xxiv) radioimmunoassay (RIA);
xxv) lateral flow immunochromatography;
xxvi) flow cytometry;
xxvii) electron microscopy (EM); and,
xxviii) enzyme-substrate assay.

It will be appreciated that the broad forms of the invention and their respective features can be used in conjunction, interchangeably and/or independently, and reference to separate broad forms is not intended to be limiting.

BRIEF DESCRIPTION OF THE DRAWINGS

An example of the present invention will now be described with reference to the accompanying drawings, in which.

DETAILED DESCRIPTION OF THE PREFERRED EMBODIMENTS

Figure 1A:
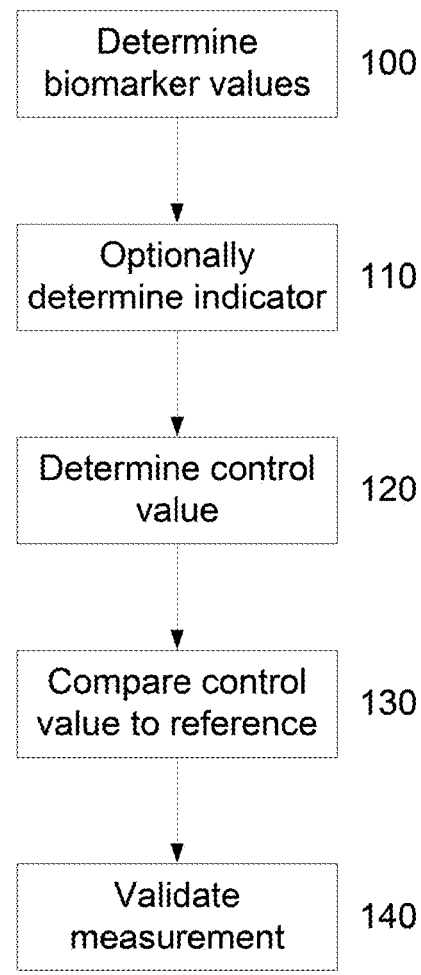
FIG. 1A is a flow chart of an example of a method for validating measurement of biomarker values.
Figure 1B:
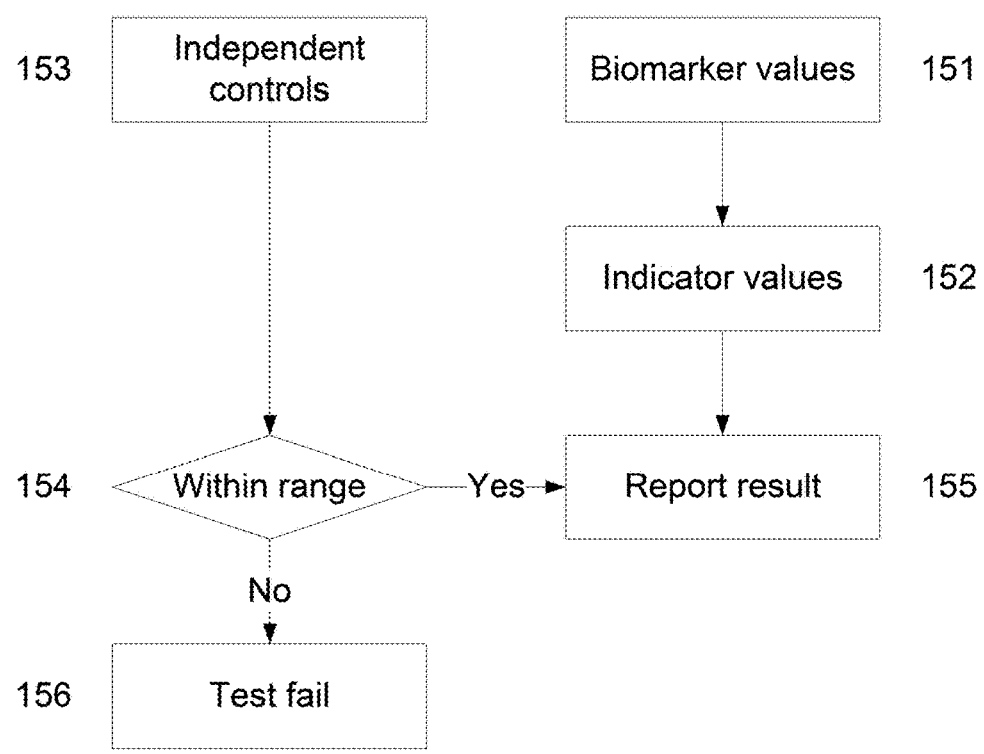
FIGS. 1B and 1C are flow charts of an example of the comparison of independent and relative control approaches.
Figure 1C:
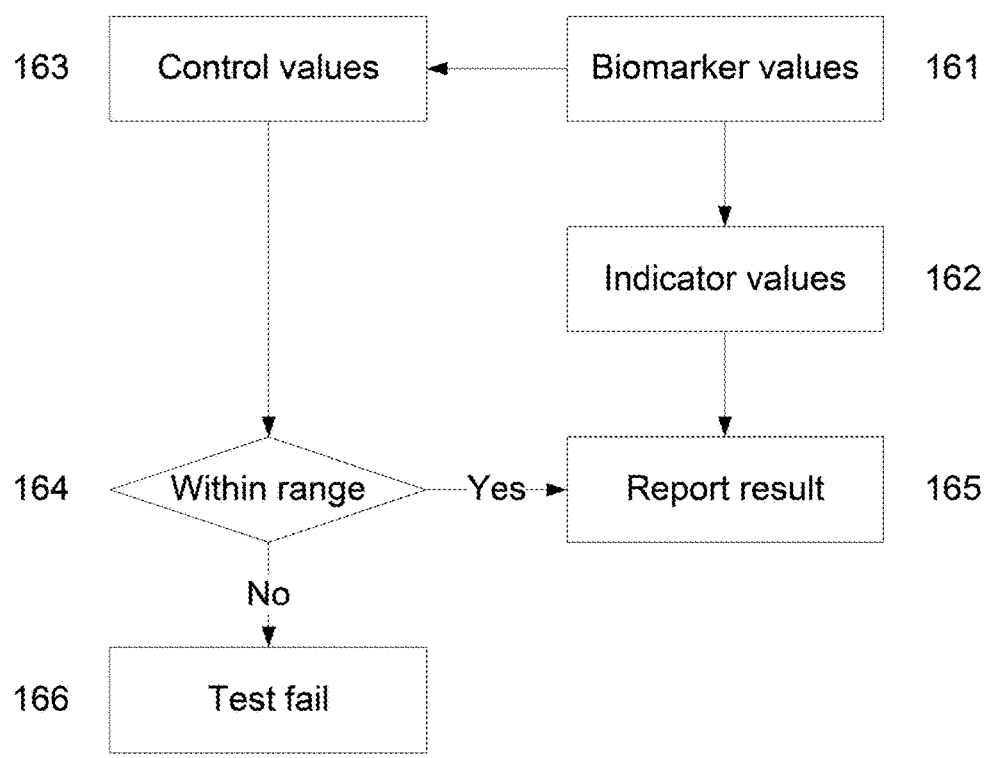

An example of a process for validating measurement of biomarkers for use in determining an indicator, such an as an indicator indicative of the likelihood of a biological subject having at least one predominant medical condition will now be described with reference to FIG. 1.

For the purpose of explanation, a number of different terms will be used.

For example, the term "biomarker" refers to any quantifiable value, or combination or derivative of parameters, that can be used as an indicator of a biological state. In the context of the current application, biomarkers include proteins, nucleic acids, such as DNA, RNA or the like, carbohydrates, lipids, proteoglycans, cells, metabolites, tissue sections, whole organisms (e.g. pathogenic and non-pathogenic microorganisms) and molecular complexes (e.g. protein/nucleic acid complex), or the like.

The term "biomarker value" refers to a value determined by quantifying the amount of, abundance of, level of, concentration of, quantity of, or activity of, the corresponding biomarker within a subject or individual. The biomarker value can be based on a measured biomarker value or a value derived therefrom, and examples will be described in more detail below.

The term "reference biomarkers" is used to refer to biomarkers whose values are known for a sample population of one or more individuals having one or more conditions, stages of one or more conditions, subtypes of one or more conditions or different prognoses. The term "reference data" refers to data measured for one or more individuals in a sample population, and may include quantification of the level or activity of the biomarkers measured for each individual, information regarding any conditions of the individuals, and optionally any other information of interest including derived biomarkers which have been derived from measured markers. Reference biomarkers are named for their primary purpose of providing a reference against which new or unknown samples can be compared.

The term "indicator values" is used to refer to combinations of biomarker values that are used in deriving an indicator, which may be indicative of the likelihood of a subject suffering from a biological condition. The indicator could be in the form of an absolute or relative numerical or other value, and could be based on comparison of a value to one or more thresholds.

The term "test" is used to refer to mechanism that is used in quantifying a plurality of biomarkers to determine respective biomarker values, which can then be used subsequently in determining indicator values. The "test" could include one or more measurement processes or steps, that could be performed collectively or independently, but which are performed using a quantification platform or technique of a selected type. The "test" may form a part of a broader "medical assessment", which could include a number of different tests, performed to allow for the diagnosis of a presence, absence, degree or prognosis associated with a medical condition.

The terms "quantification platform of a selected type" and "quantification technique of a selected type" are used interchangeably herein to refer to a device and/or method or combination of devices and/or methods that can determine the amount of, abundance of, level of, concentration of, quantity of, or activity of, one or more biomarkers of interest where either quality control measures are used as part of the overall procedure, or the use of control(s) is/are used. Representative examples of such include nucleic acid amplification techniques including polymerase chain reaction (PCR) (e.g., PCR-based methods such as real time polymerase chain reaction (RT-PCR), quantitative real time polymerase chain reaction (Q-PCR/qPCR), use of PCR to analyse chromatin conformation (CCA), and the like), hybridisation techniques including microarray analysis, low density arrays, hybridisation with allele-specific probes, enzymatic mutation detection, ligation chain reaction (LCR), oligonucleotide ligation assay (OLA), flow-cytometric heteroduplex analysis, chemical cleavage of mismatches, mass spectrometry, flow cytometry, liquid chromatography, gas chromatography, immunohistochemistry, nucleic acid sequencing (including next generation sequencing, ChIP-seq, DNA methylation analyses), single strand conformation polymorphism (SSCP), denaturing gradient gel electrophoresis (DGGE), temperature gradient gel electrophoresis (TGGE), restriction fragment polymorphisms, serial analysis of gene expression (SAGE), affinity assays including immunoassays such as immunoblot, immunoprecipitation, enzyme-linked immunosorbant assay (ELISA; EIA), lateral flow immunochromatography, radioimmunoassay (RIA), electron microscopy (EM), enzyme-substrate assay, or combinations thereof.

The term "control" is used to refer to a mechanism utilised on order to determine a pass or fail state for the validity of a test, and therefore the validity of the output.

Controls can include "independent controls", which are added to a test and are independent of the biomarkers being quantified. Thus, the independent controls are independent of the measured biomarkers and can be considered a stand-alone test for the validity of the test overall. An example is a synthetically produced in vitro transcript in a gene expression test at a known concentration. In this case, the sample being tested (ie blood) does not interact at all with the independent control. The control serves only to ensure that the reagents used across the whole test are capable of reproducing a value for this independent control to the expected value.

The term "control values" is used to refer to combinations of biomarker values or indicators that are used in assessing whether biomarker values, such as the biomarker values used to derive indicator values and the resulting indicator values, are valid. In this regard, a biomarker value or indicator value may be invalid if it has been incorrectly measured, calculated or quantified and as such is not genuinely indicative of the target condition, or if it's value is sufficiently rarely represented in the corresponding reference data that it could be reasonably presumed as true that the value could not have derived from a successful test and therefore the assay should be declared invalid (in the case of a failed control). Examples of p values that may be considered presumed to be true range from:

0.50 to 0.20
0.20 to 0.10
0.10 to 0.05
0.05 to 0.01
0.01 to 0.001
0.001 to zero.

Control values are "Relative Controls" that define a pass or fail state of a test that are not independent of the biomarkers being quantified. For example, if there are two markers measured in the test marker A and marker B, then one way in which these markers may be relative to each other is the ratio of marker A to marker B. This relationship is a control if its value is used to pass or fail the validity of a test. In this example, if the ratio of marker A to marker B is a value outside of an acceptable range, the test will be declared invalid.

A "positive control" is used to show that the test is able to produce a positive result. Typically the positive control is designed so that when exposed to the same treatment as the other markers being measured it will result in a detection at a certain level. The assumption is that if the treatment worked acceptably for the positive control, then it also worked for the other assays in the test. An example of where this will be useful is in the case where the test has been exposed to unacceptable temperatures during transport, which has destroyed some key ingredient in the test. With a key ingredient destroyed, the positive control will not work as expected and the test will be declared invalid.

A "negative control" is used to show that the test is able to produce a negative result. Typically the negative control is designed so that when exposed to the same treatment as the other markers being measured it will result in a detection below a certain level (usually below the detectable limit of the test). The assumption is that if the treatment did not result in positive detection for the negative control, then the other assays in the test are also capable of a negative detection.

The terms "biological subject", "subject," "individual" and "patient" are used interchangeably herein to refer to an animal subject, particularly a vertebrate subject, and even more particularly a mammalian subject. Suitable vertebrate animals that fall within the scope of the invention include, but are not restricted to, any member of the subphylum Chordata including primates, rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as canaries, budgerigars etc.), marine mammals (e.g., dolphins, whales), reptiles (snakes, frogs, lizards, etc.), and fish. A preferred subject is a primate (e.g., a human, ape, monkey, chimpanzee).

As used herein, the term SIRS ("systemic inflammatory response syndrome") refers to a clinical response arising from a non-specific insult with two or more of the following measurable clinical characteristics; a body temperature greater than 38° C. or less than 36° C., a heart rate greater than 90 beats per minute, a respiratory rate greater than 20 per minute, a white blood cell count (total leukocytes) greater than 12,000 per $mm^3$ or less than 4,000 per $mm^3$, or a band neutrophil percentage greater than 10%. From an immunological perspective, it may be seen as representing a systemic response to insult (e.g., major surgery) or systemic inflammation. As used herein, "inSIRS" (which includes within its scope "post-surgical" (PS) inflammation) includes the clinical response noted above but in the absence of a systemic infectious process (infection-negative systemic inflammatory response syndrome). By contrast, "ipSIRS" (infection-positive systemic inflammatory response syndrome) includes the clinical response noted above but in the presence of a presumed or confirmed infection. Presumed infection can be based on clinician's judgement whereas confirmation of an infection can be determined using microbiological culture, isolation or detection of the infectious agent or through the use of other parameters that provide evidence of infection. From an immunological perspective, ipSIRS may be seen as a systemic response to microorganisms, be it a local, peripheral or systemic infection.

As used herein, the term "likelihood" of a condition refers to a level of certainty associated with whether or not the subject may be suffering from a condition. It should be noted that this does not necessarily correlate with a degree, seriousness, severity, stage or state of a condition.

It will be appreciated that the above described terms and associated definitions are used for the purpose of explanation only and are not intended to be limiting.

In this example, the method includes determining a plurality of biomarker values at step 100, each biomarker value being indicative of a value measured or derived for at least one biomarker of the biological subject.

The biomarker values can be of any appropriate form and in particular can relate to any attribute of a subject for which a value can be quantified. This technique is particularly suited to high-throughput technologies such as mass spectrometry, sequencing platforms, array and hybridisation platforms, immunoassays, flow cytometry, and in one preferred example, the biomarker values relate to a level of activity or abundance of an expression product or other measurable molecule.

The biomarker values could be measured biomarker values, which are values of biomarkers measured for the subject, or alternatively could be derived biomarker values, which are values that have been derived from one or more measured biomarker values, for example by applying a function to the one or more measured biomarker values. As used herein, biomarkers to which a function has been applied are referred to as "derived biomarkers".

The biomarker values may be determined in any one of a number of ways. In one example, the process of determining the biomarker values can include measuring the biomarker values, for example by obtaining a sample from the biological subject and then quantifying the biomarkers within the sample. More typically however, the step of determining the biomarker values includes having an electronic processing device receive or otherwise obtain biomarker values that have been previously measured or derived. This could include for example, retrieving the biomarker values from a data store such as a local or remote instrument or database, obtaining biomarker values that have been manually input, using an input device, or the like.

At step 110 an indicator can optionally be determined with the indicator being at least partially based on the biomarker values. The indicator is generally indicative of a test result and can be determined in any one of a number of ways and may be at least partially based on a ratio of biomarker values, as will be described in more detail below. However, this is not essential and alternatively the biomarker values could be used to validate that the quantification has been performed correctly, with indicators or other interpretation of the biomarker values being performed in subsequent downstream processes.

At step 120 one or more control values are determined. The control values are determined based on a combination of the biomarker values. The biomarker values can be combined in any one of a number of ways and this can include for example adding, multiplying, subtracting, or dividing biomarker values to determine the control value. This step is performed so that multiple biomarker values can be combined into a single control value, and typically a self-normalised value, as will be described in more detail below.

At step 130 each control value is compared to a respective control reference. The respective control reference is typically established based on reference control values determined for a sample population including a mixture of healthy individuals and individuals suffering from or demonstrating clinical signs of one or more conditions. The control reference can be a single threshold value or a range defined by respective upper and lower values but more typically is in the form of distribution of control values.

At step 140 measurements of the biomarker values are validated using results of the comparison. Thus, if any control values are beyond/under the threshold, outside of a defined threshold range, or beyond a certain point in the threshold, or beyond a certain point of the distribution, this is used to indicate that the ascertained biomarker values measured are not suitable for use in generating an indicator that is reliable enough for use in determining the likelihood of a condition.

Accordingly, the above technique uses different combinations of biomarker values to identify if biomarker values are valid.

In one example, the control values are based on a combination of biomarker values, which differs to a combination of biomarkers used to establish an indicator indicative of a test result. For example, if values are quantified for three biomarkers for the subject, namely A, B and C, and the biomarker values A and B are used to establish the indicator, then combinations of A and C and B and C can be used to determine the control values.

In this example, if measurement of biomarker A is spurious, for example, due to failures in acquiring, storing or processing of a sample from the subject, or the like, this could result in an indicator value based on the combination of biomarkers A and B which is indicative of the subject having or not having a condition. However, in reality, because the measurement biomarker A is incorrect, this result is meaningless, and hence could lead to inaccurate diagnosis if relied upon.

In this case, by also determining values of control values using the combinations of A and C and B and C, it will be identified that the control value corresponding to A and C is outside an expected range for individuals either having or not having a condition of interest, meaning that the biomarker values for A and/or B are not valid, and hence can't be used in establishing an accurate indicator.

Thus, the above described process recognises that biomarkers values are typically within defined ranges for individuals regardless or not of whether they are suffering from conditions. Thus by measuring various combinations of different biomarker values, and comparing these to established ranges for a reference population of individuals having a range of different conditions, including healthy individuals, this can be used to establish whether the biomarker values are within expected ranges.

It will be further appreciated that whilst this could in theory be performed using individual biomarkers as opposed to combinations, this would require the ability to measure absolute values, such as absolute concentrations of biomarkers within a sample, which generally cannot be achieved. This is typically addressed through the use of independent controls, so that the concentration of biomarkers relative to a control of known concentration is measured. However, the use of such independent controls is typically expensive, as the control biomarkers themselves are difficult to produce, introduce complexity, and also limit the number of biomarkers that can be measured by the ability of the measuring procedures, so as more controls are introduced, this reduces the number of biomarkers that can be measured for the subject. However, by using combinations of biomarker values, such as ratios, or the like, this allows the measured biomarker values to be indicative of relative concentrations, and hence self-normalising. In particular, if the ultimate output is based on, for example, ratios of genes, then measurements of validity using similar ratios of genes is more intuitive, robust, and appropriate. Thus, by comparing different combinations of biomarker values to thresholds, this allows checks to be performed of the validity of the measured value in the native measurement space (i.e. ratios), essentially leading to a self-validating test without the need for measurement of independent controls.

Such an approach provides a better control strategy. Using the biomarkers being measured as controls specifically addresses issues associated with normalising results, improves the statistical power for the detection of failed assays, reduces the overall number of controls used, reduces the complexity of an assay and reduces overall assay cost and risk.

Firstly and by example, by using the described control strategy, many biomarkers can be used to define derived biomarkers for use as control ranges against a corresponding reference range for each derived biomarker. These biomarkers need not be those involved in the indictor biomarkers used for classification of the patient for the condition of interest. Using many relative internal biomarkers for this purpose has a smoothing and stabilizing effect on normalisation thereby reducing overall variance.

Secondly, by relying on external or spike-in controls, if there is a failure of these controls, the assay will be called invalid, even if the result from the measured genes, and therefore of the indicator value, is accurate. Thirdly, by measuring multiple interactions between measured biomarkers by looking at the larger number of relative biomarkers available, there are more relevant control checks for each biomarker being measured, resulting in higher statistical power, confidence and sensitivity. Fourthly, by avoiding the use of external controls, or use of extraneous housekeeping controls, the complexity of the assay is reduced which translates to decreased cost and risk.

In particular, this technique can avoid the need for independent controls, by using control values derived from measured biomarkers of interest to self validate a test. This approach is exemplified by comparison of the independent and relative control approaches, shown in FIGS. 1B and 1C.

As shown in this example, in each case, biomarker values are measured at steps 151, 161 and used to generate indicator values at steps 152, 162. In the dependent controls process, separate controls are measured at step 153 and assessed to determine if these are in an expected range at step 154. In contrast, in the relative controls approach, the measured biomarker values are used to derive control values at step 163, which are then assessed to determine if they are within the expected range at step 164. In each case, if the control is in range, the test results are reported at steps 155, 165, otherwise the test is failed at step 156, 166.

Thus, it can be seen the relative controls formed from control values derived from the measured biomarker values can be used in a manner similar to independent controls, but without requiring the presence of independent controls. This avoids the need for additional control markers, meaning the test can be cheaper. This also avoids the need for added independent controls failing independently, which can needlessly invalidate a valid test. Additionally, relationships between measured markers put tighter and more numerous constraints on expected values, thus increasing statistical power and therefore confidence in detection of an invalid test, as will be described in more detail below.

1) A method for validating quantification of biomarkers, the biomarkers being quantified using a quantification technique of a selected type, and the method including:
  a) determining a plurality of biomarker values, each biomarker value being indicative of a value measured or derived from a measured value, for at least one corresponding biomarker of the biological subject and being at least partially indicative of a concentration of the biomarker in a sample taken from the subject;
  b) determining at least one control value by determining a combination of biomarker values;
  c) comparing each control value to a respective control reference; and,
  d) determining if the biomarker values are valid using results of the comparison.

2) A method according to claim 1, wherein at least first and second biomarker values are used to determine an indicator indicative of a test result, and wherein the method includes determining control values including:
  a) a combination of the first and at least one other biomarker value; and,
  b) a combination of the second and at least one other biomarker value.

3) A method according to claim 2, wherein the method includes:
  a) determining at least four biomarker values, the indicator being based on a combination of:
    i) a first indicator value calculated using first and second biomarker values; and,
    ii) a second indicator value calculated using third and fourth biomarker values; and,
  b) determining control values including:
    i) a first control value calculated using first and third biomarker values;
    ii) a second control value calculated using first and fourth biomarker values;
    iii) a third control value calculated using second and third biomarker values; and,
    iv) a fourth control value calculated using second and fourth biomarker values.

4) A method according to claim 3, wherein the method includes determining control values including:
  a) a fifth control value calculated using first and second biomarker values;
  b) a sixth control value calculated using third and fourth biomarker values; and,
  c) control values calculated using a combination of measured biomarkers not used in determining an indicator value.

5) A method according to claim 3, wherein the method includes calculating at least one of the indicator values and the control values by applying a function to the respective biomarker values.

6) A method according to claim 5, wherein the function includes at least one of:
  a) multiplying two biomarker values;
  b) dividing two biomarker values;
  c) a ratio of two biomarker values;
  d) adding two biomarker values;
  e) subtracting two biomarker values;
  f) a weighted sum of at least two biomarker values;
  g) a log sum of at least two biomarker values; and,
  h) a sigmoidal function of at least two biomarker values.

7) A method according to claim 1, wherein the method includes determining:
  a) a first control value using a ratio of first and third biomarker values;

b) a second control value using a ratio of first and fourth biomarker values;
c) a third control value using a ratio of second and third biomarker values; and,
d) a fourth control value using a ratio of second and fourth biomarker values.
8) A method according to claim 7, wherein the method includes determining control values including:
a) a fifth control value using a ratio of first and second biomarker values;
b) a sixth control value using a ratio of third and fourth biomarker values; and,
c) controls values calculated using a ratio of measured biomarkers not used in determining an indicator value.
9) A method according to claim 1, wherein the method includes:
a) determining a validity probability based on the result of the comparison; and,
b) using the validity probability to determine if the biomarker values are valid.
10) A method according to claim 1, wherein the method includes:
a) determining a control value probability for the comparison of each control value to the respective control reference; and,
b) combining the control value probabilities to determine the validity probability.
11) A method according to claim 1, wherein the control reference is at least one of:
a) a control value threshold range;
b) a control value threshold; and,
c) a control value distribution.
12) A method according to claim 11, wherein the control reference is a control value threshold range, and wherein the method includes:
a) comparing each control value to a respective control value threshold range; and,
b) determining at least one of the biomarker values to be invalid if any one of the control values falls outside the respective control value threshold range.
13) A method according to claim 11, wherein the control reference is a control value distribution, and wherein the method includes:
a) comparing each control value to a respective control value distribution; and,
b) determining the validity using the results of the comparisons.
14) A method according to claim 11, wherein each respective reference is derived from biomarker values collected from a number of individuals in a sample population.
15) A method according to claim 14, wherein each respective reference is determined for at least part of the sample population.
16) A method according to claim 14, wherein the sample population includes:
a) a plurality of individuals of different sexes;
b) a plurality of individuals of different ethnicities;
c) a plurality of healthy individuals;
d) a plurality of individuals suffering from at least one diagnosed medical condition;
e) a plurality of individuals showing clinical signs of at least one medical condition; and,
f) first and second groups of individuals, each group of individuals suffering from a respective diagnosed medical condition.
17) A method according to claim 2, wherein the indicator is for use in determining the likelihood that a biological subject has at least one medical condition, and wherein the sample population includes:
a) individuals presenting with clinical signs of the at least one medical condition;
b) individuals diagnosed with the at least one medical condition; and,
c) healthy individuals.
18) A method according to claim 2, wherein the indicator is determined by combining the first and second derived indicator values using a combining function, the combining function being at least one of:
a) an additive model;
b) a linear model;
c) a support vector machine;
d) a neural network model;
e) a random forest model;
f) a regression model;
g) a genetic algorithm;
h) an annealing algorithm;
i) a weighted sum; and,
j) A nearest neighbour model.
19) A method according to claim 2, wherein the method includes:
a) determining an indicator value;
b) comparing the indicator value to at least one indicator value range; and,
c) determining the indicator at least in part using a result of the comparison.
20) A method according to claim 2, wherein the indicator is indicative of a likelihood of the subject having at least one medical condition.
21) A method according to claim 2, wherein the method includes generating a representation of the indicator.
22) A method according to claim 21, wherein the representation includes:
a) an alphanumeric indication of the indicator value;
b) a graphical indication of a comparison of the indicator value to one or more thresholds; and,
c) an alphanumeric indication of a likelihood of the subject having at least one medical condition.
23) A method according to claim 1, wherein the biomarker value is indicative of a level or abundance of a molecule, cell or organism selected from one or more of:
a) proteins;
b) nucleic acids;
c) carbohydrates;
d) lipids;
e) proteoglycans;
f) cells;
g) metabolites;
h) tissue sections;
i) whole organisms; and,
j) molecular complexes.
24) A method according to claim 1, wherein the method is performed at least in part using one or more electronic processing devices.
25) A method according to claim 1, wherein the indicator reference is retrieved from a database.
26) A method according to claim 1, wherein the method includes, in the one or more electronic processing devices:
a) receiving the biomarker values;
b) determining the at least one control value using at least two of the biomarker values;
c) comparing the at least one control value to the respective control value threshold; and, d) determining if the test is a valid test using the results of the comparison.

27) A method according to claim 26, wherein the method includes, in the one or more electronic processing devices:
   a) determining the indicator by:
      i) calculating a first indicator value using a ratio of first and second biomarker values;
      ii) calculating a second indicator value using a ratio of third and fourth second biomarker values; and,
      iii) determining a sum of the first and second indicator values;
   b) determining a plurality of control values by:
      i) calculating a first control value using a ratio of the first and third biomarker values;
      ii) calculating a second control value using a ratio of the first and fourth biomarker values;
      iii) calculating a third control value using a ratio of the second and third biomarker values; and,
      iv) calculating a fourth control value using a ratio of the second and fourth biomarker values;
   c) comparing each control value to a respective threshold range; and,
   d) displaying the indicator in response to a successful comparison for each control value.

28) A method according to claim 27, wherein the method includes, in the one or more electronic processing devices:
   a) calculating a fifth control value using a ratio of the first and second biomarker values;
   b) calculating a sixth control value using a ratio of the third and fourth biomarker values; and,
   c) calculating an additional or set of control values by using a combination of biomarkers not used in determining an indicator value.

29) A method according to claim 1, wherein the biomarkers are gene expression products and wherein the method includes:
   a) obtaining a sample from a biological subject, the sample including the gene expression products;
   b) amplifying at least the gene expression products in the sample; and,
   c) for each gene expression product, determining an amplification amount representing a degree of amplification required to obtain a defined level of the respective gene expression.

30) A method according to claim 29, wherein the amplification amount is at least one of:
   a) a cycle time;
   b) a number of cycles;
   c) a cycle threshold; and,
   d) an amplification time.

31) A method according to claim 29, wherein the biomarkers are gene expression products and wherein the method includes, determining a combination of biomarker values by subtracting amplification amounts for the respective gene expression products so that the combination of biomarker values represents a ratio of the relative concentration of the respective gene expression products.

32) A method according to claim 1, wherein the biomarker values are obtained from a biological subject presenting with clinical signs of at least one medical condition.

33) A method according to claim 32, wherein the at least one condition includes ipSIRS and wherein the biomarker values correspond to relative concentrations of LAMP1, CEACAM4, PLAC8 and PLA2G7.

34) A method according to claim 32, wherein the biomarker values are obtained from a biological subject presenting with clinical signs common to first and second conditions and wherein the indicator is for use in distinguishing between the first and second conditions.

35) A method according to claim 34, wherein the first and second conditions include inSIRS and ipSIRS.

36) A method according to claim 1, wherein the quantification technique is at least one of:
   a) a nucleic acid amplification technique;
   b) polymerase chain reaction (PCR);
   c) a hybridisation technique;
   d) microarray analysis;
   e) low density arrays;
   f) hybridisation with allele-specific probes;
   g) enzymatic mutation detection;
   h) ligation chain reaction (LCR);
   i) oligonucleotide ligation assay (OLA);
   j) flow-cytometric heteroduplex analysis;
   k) chemical cleavage of mismatches;
   l) mass spectrometry;
   m) flow cytometry;
   n) liquid chromatography;
   o) gas chromatography;
   p) immunohistochemistry;
   q) nucleic acid sequencing;
   r) single strand conformation polymorphism (SSCP);
   s) denaturing gradient gel electrophoresis (DGGE);
   t) temperature gradient gel electrophoresis (TGGE);
   u) restriction fragment polymorphisms;
   v) serial analysis of gene expression (SAGE);
   w) affinity assays;
   x) radioimmunoassay (RIA);
   y) lateral flow immunochromatography;
   z) flow cytometry;
   aa) electron microscopy (EM); and,
   bb) enzyme-substrate assay.

37) Apparatus for validating measurement of biomarker values used in generating an indicator, the biomarkers being quantified using a quantification technique of a selected type, and the apparatus including at least one processing device that:
   a) determines a plurality of biomarker values, each biomarker value being indicative of a value measured or derived from a measured value, for at least one corresponding biomarker of the biological subject and being at least partially indicative of a concentration of the biomarker in a sample taken from the subject;
   b) determines at least one control value by determining a combination of biomarker values;
   c) compares each control value to a respective control reference; and,
   d) determines if the biomarker values are valid using results of the comparison.

38) A method for validating an indicator used in determining the likelihood of a biological subject having at least one medical condition, the biomarkers being quantified using a quantification technique of a selected type and the method including:
   a) determining a plurality of biomarker values, each biomarker value being indicative of a value measured or derived for at least one corresponding biomarker of the biological subject;
   b) determining an indicator indicative of the likelihood of a biological subject having at least one medical condition by:

i) calculating a first indicator value using first and second biomarker values;
ii) calculating a second indicator value using third and fourth second biomarker values; and,
iii) determining the indicator using the first and second indicator values;
c) calculating at least one of:
i) a first control value using the first and third biomarker values;
ii) a second control value using the first and fourth biomarker values;
iii) a third control value using the second and third biomarker values;
iv) a fourth control value using the second and fourth biomarker values;
v) a fifth control value using the first and fourth second values;
vi) a sixth control value using the third and fourth biomarker values; and,
vii) an additional or set of control values by using a combination of biomarkers not used in determining an indicator value;
d) comparing the at least one control value to a respective control value threshold; and,
e) selectively validating the indicator using the results of the comparison.

39) Apparatus for validating an indicator indicative of measured values of gene expression products, the biomarkers being quantified using a quantification technique of a selected type, the apparatus including at least one processing device that:
a) determines a plurality of biomarker values, each biomarker value being indicative of a value measured or derived for at least one corresponding biomarker of the biological subject;
b) determines the indicator by:
i) calculating a first indicator value using first and second biomarker values;
ii) calculating a second indicator value using third and fourth second biomarker values; and,
iii) determining the indicator using the first and second indicator values;
c) calculates at least one of:
i) a first control value using the first and third biomarker values;
ii) a second control value using the first and fourth biomarker values;
iii) a third control value using the second and third biomarker values;
iv) a fourth control value using the second and fourth biomarker values;
v) a fifth control value using the first and second biomarker values;
vi) a sixth control value using the third and fourth biomarker values; and,
vii) an additional or set of control values by using a combination of biomarkers not used in determining an indicator value.
d) compares the at least one control value to a respective control value threshold; and,
e) selectively validates the indicator using the results of the comparison.

40) A method for validating an indicator used in determining the likelihood of a biological subject having at least one medical condition, the biomarkers being quantified using a quantification technique of a selected type and the method including:

a) obtaining a sample from a biological subject, the sample including gene expression products;
b) quantifying at least some gene expression products in the sample to determine a concentration of the gene expression product in the sample;
c) determining an indicator indicative of the likelihood of a biological subject having at least one medical condition by combining:
i) a first indicator value indicative of a ratio of the concentration of the first and second gene expression products; and,
ii) a second indicator value indicative of a ratio of the concentration of the third and fourth gene expression products;
d) determining control values by determining at least one of:
i) a first control value indicative of a ratio of the concentration of the first and third gene expression products;
ii) a second control value indicative of a ratio of the concentration of the first and fourth gene expression products;
iii) a third control value indicative of a ratio of the concentration of the second and third gene expression products;
iv) a fourth control value indicative of a ratio of the concentration of the second and fourth gene expression products;
v) a fifth control value indicative of a ratio of the concentration of the first and second gene expression products;
vi) a sixth control value indicative of a ratio of the concentration of the third and fourth gene expression products; and,
vii) an additional or set of control values by using a combination of gene expression products not used in determining an indicator value;
e) comparing each control value to a respective control value threshold range; and,
f) validating the indicator if each of the control values is within the respective control value range.

41) A method according to claim 40, wherein the method includes quantifying the concentration of the gene expression products by:
a) amplifying at least some gene expression products in the sample; and,
b) for each of a plurality of gene expression products, determining an amplification amount representing a degree of amplification required to obtain a defined level of the respective gene expression product.

42) A method according to claim 40, wherein the method includes:
a) determining the indicator by:
i) determining a first indicator value calculated using the first and second amplification times indicative of the concentration of first and second gene expression products; and,
ii) a second indicator value calculated using third and fourth amplification times indicative of the relative concentration of third and fourth gene expression products; and,
b) determining control values by determining at least one of:
i) a first control value calculated using first and third amplification times indicative of the relative concentration of first and third gene expression products;

ii) a second control value calculated using first and fourth amplification times indicative of the relative concentration of first and fourth gene expression products;

iii) a third control value calculated using second and third amplification times indicative of the relative concentration of second and third gene expression products;

iv) a fourth control value calculated using second and fourth amplification times indicative of the relative concentration of second and fourth gene expression products;

v) a fifth control value calculated using first and second amplification times indicative of the relative concentration of first and second gene expression products;

vi) a sixth control value calculated using third and fourth amplification times indicative of the relative concentration of third and fourth gene expression products; and, vii) an additional or set of control values by using a combination of amplification times not used in determining an indicator value.

43) Apparatus for validating an indicator used in determining the likelihood of a biological subject having at least one medical condition, the apparatus including:
 a) a sampling device that obtains a sample from a biological subject, the sample including gene expression products;
 b) a quantification device that quantifies at least some gene expression products in the sample to determine a concentration of the gene expression product in the sample; and,
 c) at least one processing device that:
  i) determines an indicator indicative of the likelihood of a biological subject having at least one medical condition by combining:
   (1) a first indicator value indicative of a ratio of the concentration of the first and second gene expression products; and,
   (2) a second indicator value indicative of a ratio of the concentration of the third and fourth gene expression products;
  ii) determines control values by determining at least one of:
   (1) a first control value indicative of a ratio of the concentration of the first and third gene expression products;
   (2) a second control value indicative of a ratio of the concentration of the first and fourth gene expression products;
   (3) a third control value indicative of a ratio of the concentration of the second and third gene expression products;
   (4) a fourth control value indicative of a ratio of the concentration of the second and fourth gene expression products;
   (5) a fifth control value indicative of a ratio of the concentration of the first and second gene expression products;
   (6) a sixth control value indicative of a ratio of the concentration of the third and fourth gene expression products; and,
   (7) an additional or set of control values indicative of a ratio of the concentration of biomarkers not used in determining an indicator value;
  iii) compares each control value to a respective control value threshold range; and,
  iv) validates the indicator if each of the control values is within the respective control value range.

44) A method for validating quantification of biomarkers, the method including:
 a) determining a plurality of biomarker values, each biomarker value being indicative of a value measured or derived from a measured value, for at least one corresponding biomarker of the biological subject and being at least partially indicative of a concentration of the biomarker in a sample taken from the subject;
 b) determining at least one control value by determining a combination of biomarker values;
 c) comparing each control value to a respective control reference; and,
 d) determining if the biomarker values are valid using results of the comparison, wherein the biomarker value is indicative of a level or abundance of a molecule, cell or organism selected from one or more of:
  i) proteins;
  ii) nucleic acids;
  iii) carbohydrates;
  iv) lipids;
  v) proteoglycans;
  vi) cells; and,
  vii) pathogenic organisms.

45) A method for validating quantification of biomarkers, the method including:
 a) determining a plurality of biomarker values, each biomarker value being indicative of a value measured or derived from a measured value, for at least one corresponding biomarker of the biological subject and being at least partially indicative of a concentration of the biomarker in a sample taken from the subject;
 b) determining at least one control value by determining a combination of biomarker values;
 c) comparing each control value to a respective control reference; and,
 d) determining if the biomarker values are valid using results of the comparison, wherein the biomarker value is indicative of a level or abundance of a molecule, cell or organism selected from one or more of:
  i) proteins;
  ii) nucleic acids;
  iii) carbohydrates;
  iv) lipids;
  v) proteoglycans;
  vi) cells;
  vii) metabolites;
  viii) tissue sections;
  ix) whole organisms; and,
  x) molecular complexes.

46) A method for validating quantification of biomarkers, the method including:
 a) determining a plurality of biomarker values, each biomarker value being indicative of a value measured or derived from a measured value, for at least one corresponding biomarker of the biological subject and being at least partially indicative of a concentration of the biomarker in a sample taken from the subject;
 b) determining at least one control value by determining a combination of biomarker values;
 c) comparing each control value to a respective control reference; and,
 d) determining if the biomarker values are valid using results of the comparison, wherein the biomarkers are quantified using at least one of:
  i) a nucleic acid amplification technique;
  ii) polymerase chain reaction (PCR);
  iii) a hybridisation technique;

iv) microarray analysis;
v) low density arrays;
vi) hybridisation with allele-specific probes;
vii) enzymatic mutation detection;
viii) ligation chain reaction (LCR);
ix) oligonucleotide ligation assay (OLA);
x) flow-cytometric heteroduplex analysis;
xi) chemical cleavage of mismatches;
xii) mass spectrometry;
xiii) flow cytometry;
xiv) liquid chromatography;
xv) gas chromatography;
xvi) immunohistochemistry;
xvii) nucleic acid sequencing;
xviii) single strand conformation polymorphism (SSCP);
xix) denaturing gradient gel electrophoresis (DGGE);
xx) temperature gradient gel electrophoresis (TGGE);
xxi) restriction fragment polymorphisms;
xxii) serial analysis of gene expression (SAGE);
xxiii) affinity assays;
xxiv) radioimmunoassay (RIA);
xxv) lateral flow immunochromatography;
xxvi) flow cytometry;
xxvii) electron microscopy (EM); and,
xxviii) enzyme-substrate assay.

A number of further features will now be described.

In one example, at least three biomarker values are used, with first and second biomarker values being used to determine the indicator and with the control values being determined using a combination of the first and at least one other biomarker value and the second and at least one other biomarker value. However, in another preferred example, the method includes determining at least four biomarker values. In this case, the indicator can be based on a combination of a first indicator value calculated using first and second biomarker values and a second indicator value calculated using third and fourth biomarker values. These two indicator values can then be combined to form the indicator, which combines the discriminatory power of each of the first two indicator values. This allows two independent pairs of biomarker values to be combined and used to establish the indicator, which can significantly enhance the ability of the indicator to discriminate the likelihood of the subject having the condition.

Furthermore, when using four biomarker values, this allows at least four control values to be determined including a first control value calculated using first and third biomarker values, a second control value calculated using first and fourth biomarker values, a third control value calculated using second and third biomarker values and a fourth control value calculated using second and fourth biomarker values. Thus, again, this allows for additional control values to be utilised, further increasing the likelihood that invalid measurements can be accurately discriminated. It will be appreciated that combinations of biomarkers comprising the indicator value can also be control values: in this example the first and second biomarkers and the third and fourth biomarkers make up the indicator value, and they too, if out of range to a corresponding reference, may indicate failure of the assay.

It will also be appreciated that in the above example, each of the biomarker values used in establishing the indicator are also used in the validation check. This maximises the use of biomarkers, so that in effect each measured biomarker value is used in both generating the indicator and the validation. For platforms and processes that can only handle limited numbers of biomarker values, this can therefore maximise the discriminatory power of the indicator, by allowing all measured biomarker values to be used in determining the indicator, whilst still ensuring indicator validity. However, this is not essential, and additionally and/or alternatively, comparison to a biomarker value measured for the subject, but not used in generating the indicator could be performed.

It should also be noted that the indicator values could also be used as control values. In this instance, typically an acceptable range for indicator values would be specified for assessing the likelihood of a subject having a condition, with this range representing the maximum and minimum indicator values observed or expected in the target population. Values outside of this range may imply a problem with at least one of the underlying values comprising the indicator value, and the test will be declared invalid. Accordingly, in this example, the method includes determining control values including one or more of a fifth control value using a ratio of first and second biomarker values, a sixth control value using a ratio of third and fourth biomarker values and, a single or set of controls values calculated using a ratio of measured biomarkers not used in determining an indicator value.

The method typically includes calculating at least one of the indicator values and the control values by applying a function to the respective biomarker values. The function used will therefore vary depending on the preferred implementation. In one example, the function includes at least one of multiplying two biomarker values, dividing two biomarker values; adding two biomarker values, subtracting two biomarker values, a weighted sum of at least two biomarker values, a log sum of at least two biomarker values and, a sigmoidal function of at least two biomarker values.

More typically the function is division of two biomarker values, or log subtraction (which is equivalent to division of absolute values) so that the derived biomarker value corresponds to a ratio of two measured biomarker values. There are a number of reasons why the ratio might be preferred. For example, use of a ratio is self-normalising, meaning variations in measuring techniques will automatically be accommodated. For example, if the input concentration of a sample is doubled, the relative proportions of biomarkers will remain the same. As a result, the type of function therefore has a stable profile over a range of input concentrations, which is important because input concentration is a known variable for expression data. Additionally, many biomarkers are nodes on biochemical pathways, so the ratio of biomarkers gives information about the relative activation of one biological pathway to another, which is a natural representation of biological change within a system. Finally, ratios are typically easily interpreted.

In one example, the control values are ratios, with each control value being compared to a respective control value threshold range and determining at least one of the biomarker values to be invalid if any one of the control values falls outside the respective control value threshold range. In this instance, each respective threshold range is typically derived from biomarker values collected from a number of individuals in a sample population. This can be performed for example using a statistical method or computer-implemented classifier algorithm trained on biomarker values for the sample population. The sample population typically includes a plurality of healthy individuals, a plurality of individuals suffering from at least one diagnosed medical condition, a plurality of individuals showing clinical signs of at least one medical condition or first and second groups of individuals, each group of individuals suffering from a respective diagnosed medical condition. This can be used to provide a suitable cross section of the population and to ensure that the control value threshold ranges are not influenced by the presence or absence of conditions.

In particular, when an indicator is for use in determining the likelihood that a biological subject has a specific medical condition, the sample population includes individuals presenting with clinical signs of the specific medical condition, individuals diagnosed or confirmed to have or have had (including retrospectively) the specific medical condition and/or healthy individuals. This ensures that the assessment of indicator validity applies regardless of not or whether the individual has the specific condition or not.

It will also be appreciated that the sample population could also include a plurality of individuals of different sexes, ethnicities, ages, or the like, allowing the control value ranges to be common across populations. However, this is not essential, and alternatively control value thresholds could be established that are specific to a particular sub-set of the population. In this case, it would be necessary to ensure that the control value threshold ranges used are appropriate for the subject under consideration.

Typically the indicator is determined by combining the first and second derived indicator values using a combining function, the combining function being at least one of an additive model, a linear model, a support vector machine, a neural network model, a random forest model, a regression model, a genetic algorithm, an annealing algorithm, a weighted sum and a nearest neighbour model.

In one example, the method further includes determining an indicator value, comparing the indicator value to at least one indicator value range and determining the indicator at least in part using a result of the comparison. Thus, once it has been established that the biomarker values are suitable for use in determining the indicator, the indicator can be calculated and compared to an indicator value range to assess the likelihood of the subject having at least one medical condition.

Following this, the method can further include generating a representation of the indicator. In this regard, the representation allows the indicator to be viewed, for example by a medical practitioner, allowing the medical practitioner to perform a diagnosis and assess what intervention, if any, to perform. The representation can be of any appropriate form and can include one or more of an alphanumeric indication of an indicator value, a graphical indication of a comparison of the indicator value to one or more thresholds and an alphanumeric indication of a likelihood of the subject having at least one medical condition. A specific example representation will be described in more detail below.

The method is typically performed at least in part using one or more electronic processing devices, for example forming part of one or more processing systems, such as computers or servers, which could in turn connected to one or more other computing devices, such as mobile phones, portable computers or the like, via a network architecture, as will be described in more detail below.

In one example, the one or more electronic processing devices receive the biomarker values, determine the indicator using biomarker values, determine the at least one control value using at least two of the biomarker values, compare the at least one control value to the respective control value threshold and determine if the test is a valid test using the results of the comparison.

In this regard, the biomarker values can be received from a database or the like, in which the values have been previously stored, or could be received directly from a measuring device, such as a PCR machine or the like, which is used in determining the biomarker values. The processing devices can then automatically assess the validity of the measurements and then, if valid calculate the indicator, generating and displaying a representation of this as required. Thus, it will be appreciated that this can provide a substantially automated procedure from the point at which a sample is loaded into a measuring device.

In one example, the one or more electronic processing devices determine the indicator by calculating a first indicator value using a ratio of first and second biomarker values, calculating a second indicator value using a ratio of third and fourth second biomarker values and determining a sum of the first and second indicator values. The one or more electronic processing devices similarly determine a plurality of internal relative control values by calculating a first control value using a ratio of the first and third biomarker values, calculating a second control value using a ratio of the first and fourth biomarker values, calculating a third control value using a ratio of the second and third biomarker values and calculating a fourth control value using a ratio of the second and fourth biomarker values, before comparing each control value to a respective threshold range and displaying the indicator in response to a successful comparison for each control value.

When the biomarkers are gene expression products, the relative abundance of target biomarkers can be determined thus; obtain a sample from a biological subject, such that the sample includes the target gene expression products, then amplify at least the target gene expression products in the sample, then for each gene expression product determine an amplification amount required to obtain a defined level of the respective gene expression product, the amplification amount being dependent on the concentration of the gene expression product in the sample being based on a cycle time, number of amplification cycles, a cycle threshold, an amplification time, or the like. In this case, relative biomarkers can be generated using combinations of amplification times by subtracting amplification times for the respective gene expression products so that these relative biomarker values represent a ratio of the relative concentration of the respective gene expression products.

It will be appreciated that the above described process is typically performed on a biological subject presenting with clinical signs of at least one medical condition. In this case, a medical practitioner will typically perform an initial assessment of the clinical signs and establish a specific test to be performed. For example, if the practitioner identifies that the subject may have ipSIRS, the above described process is typically performed with relative biomarker values corresponding to relative concentrations of LAMP1, CEACAM4, PLAC8 and PLA2G7.

More typically the clinical signs could be common to first and second conditions, which case the indicator is for use in distinguishing between the first and second conditions. Thus, for example, inSIRS and ipSIRS typically have similar clinical signs, so practitioners can use the indicator to distinguish between the conditions.

Thus, the above could be used for validating an indicator used in determining the likelihood of a biological subject having at least one medical condition, the biomarkers being quantified using a quantification technique of a selected type and the method including:
    a) determining a plurality of biomarker values, each biomarker value being indicative of a value measured or derived from at least one corresponding measured biomarker of the biological subject;

b) determining an indicator indicative of the likelihood of a biological subject having at least one medical condition by:
  i) calculating a first indicator value using first and second biomarker values;
  ii) calculating a second indicator value using third and fourth second biomarker values;
  iii) determining the indicator using the first and second indicator values; and,
c) calculating at least one of:
  i) a first control value using the first and third biomarker values;
  ii) a second control value using the first and fourth biomarker values;
  iii) a third control value using the second and third biomarker values;
  iv) a fourth control value using the second and fourth biomarker values;
d) comparing the at least one control value to a respective control value threshold; and,
e) selectively validating the indicator using the results of the comparison.

Thus, the above could also be used for validating an indicator used in determining the likelihood of a biological subject having at least one medical condition, the biomarkers being quantified using a quantification technique of a selected type and the method including:
a) obtaining a sample from a biological subject, the sample including gene expression products;
b) quantifying at least some gene expression products in the sample to determine a concentration of the gene expression product in the sample;
c) determining an indicator indicative of the likelihood of a biological subject having at least one medical condition by combining:
  i) a first indicator value indicative of a ratio of the concentration of the first and second gene expression products; and,
  ii) a second indicator value indicative of a ratio of the concentration of the third and fourth gene expression products; and,
d) determining control values by determining:
  i) a first control value indicative of a ratio of the concentration of the first and third gene expression products;
  ii) a second control value indicative of a ratio of the concentration of the first and fourth gene expression products;
  iii) a third control value indicative of a ratio of the concentration of the second and third gene expression products; and,
  iv) a fourth control value indicative of a ratio of the concentration of the second and fourth gene expression products;
e) comparing each control value to a respective control value threshold; and,
f) selectively validate the indicator using the results of the comparison.

Figure 2:
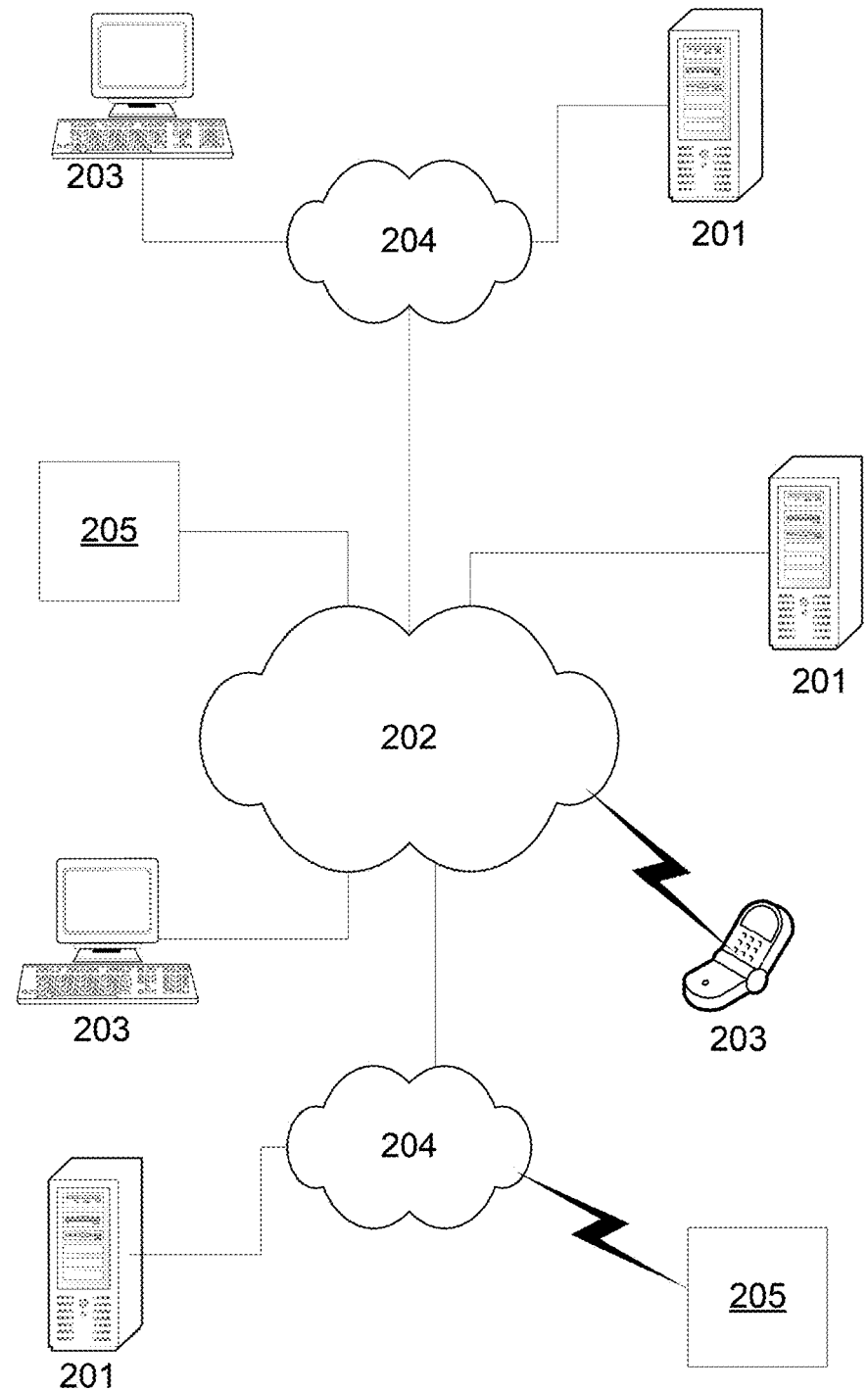
FIG. 2 is a schematic diagram of an example of a distributed computer architecture.

In one example, the process is performed by one or more processing systems operating as part of a distributed architecture, an example of which will now be described with reference to FIG. 2.

In this example, a number of base stations 201 are coupled via communications networks, such as the Internet 202, and/or a number of local area networks (LANs) 204, to a number of client devices 203 and one or more measuring devices 205, such as PCR, sequencing machines, or the like.

It will be appreciated that the configuration of the networks 202, 204 are for the purpose of example only, and in practice the base stations 201, client devices 203 and measuring devices 205, an communicate via any appropriate mechanism, such as via wired or wireless connections, including, but not limited to mobile networks, private networks, such as an 802.11 networks, the Internet, LANs, WANs, or the like, as well as via direct or point-to-point connections, such as Bluetooth, or the like.

In one example, each base station 201 includes one or more processing systems 210, each of which may be coupled to one or more databases 211. The base station 201 is adapted to be used in calculating and validating indicators and generating representations for these to be displayed via client devices. The client devices 203 are typically adapted to communicate with the base station 201, allowing indicator representations to be displayed.

Whilst the base station 201 is a shown as a single entity, it will be appreciated that the base station 201 can be distributed over a number of geographically separate locations, for example by using processing systems 210 and/or databases 211 that are provided as part of a cloud based environment. However, the above described arrangement is not essential and other suitable configurations could be used.

Figure 3:
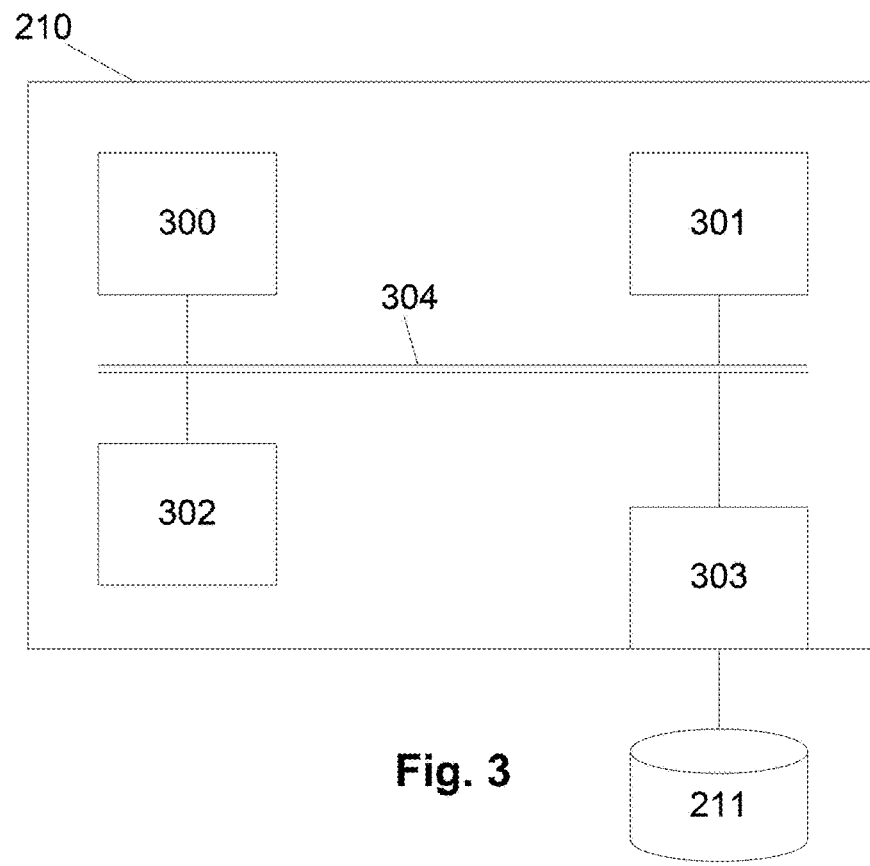
FIG. 3 is a schematic diagram of an example of a base station processing system.

An example of a suitable processing system 210 is shown in FIG. 3. In this example, the processing system 210 includes at least one microprocessor 300, a memory 301, an optional input/output device 302, such as a keyboard and/or display, and an external interface 303, interconnected via a bus 304 as shown. In this example the external interface 303 can be utilised for connecting the processing system 210 to peripheral devices, such as the communications networks 202, 204, databases 211, other storage devices, or the like. Although a single external interface 303 is shown, this is for the purpose of example only, and in practice multiple interfaces using various methods (e.g., Ethernet, serial, USB, wireless or the like) may be provided.

In use, the microprocessor 300 executes instructions in the form of applications software stored in the memory 301 to allow the required processes to be performed. The applications software may include one or more software modules, and may be executed in a suitable execution environment, such as an operating system environment, or the like.

Accordingly, it will be appreciated that the processing system 210 may be formed from any suitable processing system, such as a suitably programmed client device, PC, web server, network server, or the like. In one particular example, the processing system 210 is a standard processing system, which executes software applications stored on non-volatile (e.g., hard disk) storage, although this is not essential. However, it will also be understood that the processing system could be any electronic processing device such as a microprocessor, microchip processor, logic gate configuration, firmware optionally associated with implementing logic such as an FPGA (Field Programmable Gate Array), or any other electronic device, system or arrangement.

Figure 4:
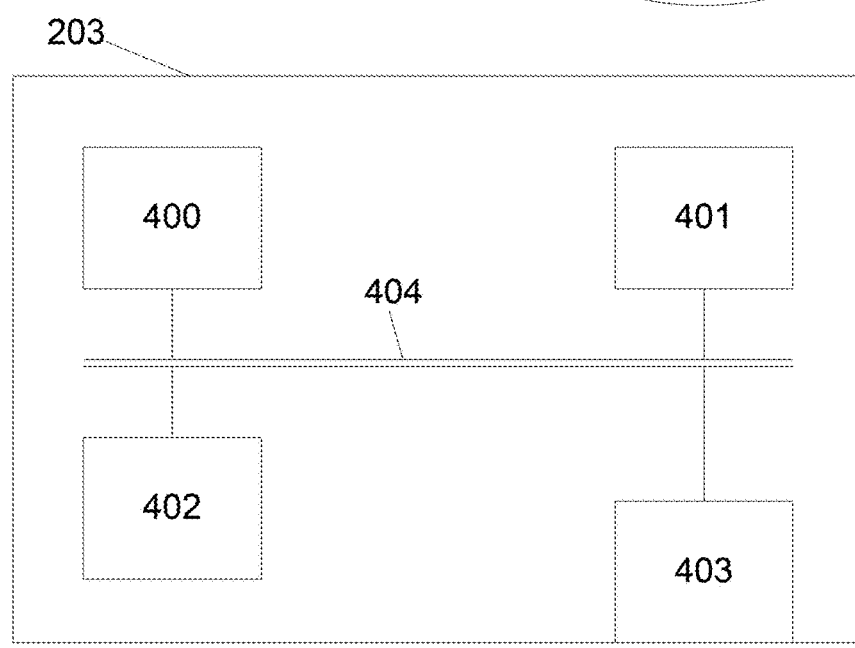
FIG. 4 is a schematic diagram of an example of a client device of FIG. 2.

As shown in FIG. 4, in one example, the client device 203 includes at least one microprocessor 400, a memory 401, an input/output device 402, such as a keyboard and/or display, and an external interface 403, interconnected via a bus 404 as shown. In this example the external interface 403 can be utilised for connecting the client device 203 to peripheral devices, such as the communications networks 202, 204, databases, other storage devices, or the like. Although a single external interface 403 is shown, this is for the purpose of example only, and in practice multiple interfaces using various methods (e.g., Ethernet, serial, USB, wireless or the like) may be provided.

In use, the microprocessor 400 executes instructions in the form of applications software stored in the memory 401 to allow communication with the base station 201, for example to allow for selection of parameter values and viewing of representations, or the like.

Accordingly, it will be appreciated that the client devices 203 may be formed from any suitable processing system, such as a suitably programmed PC, Internet terminal, laptop, or hand-held PC, and in one preferred example is either a tablet, or smart phone, or the like. Thus, in one example, the processing system 210 is a standard processing system, which executes software applications stored on non-volatile (e.g., hard disk) storage, although this is not essential. However, it will also be understood that the client devices 203 can be any electronic processing device such as a microprocessor, microchip processor, logic gate configuration, firmware optionally associated with implementing logic such as an FPGA (Field Programmable Gate Array), or any other electronic device, system or arrangement.

Examples of the processes for determining and validating measurements of indicators will now be described in further detail. For the purpose of these examples it is assumed that one or more processing systems 210 acts to receive measured biomarker values from the measuring devices, calculate indicator values and control values, and use these to calculate and validate an indicator which can then be displayed as part of a representation via hosted webpages or an App residing on the client device 203. The processing system 210 is therefore typically a server which communicates with the client device 203 and measuring devices 205 via a communications network, or the like, depending on the particular network infrastructure available.

To achieve this the processing system 210 of the base station 201 typically executes applications software for performing required processes, with actions performed by the processing system 210 being performed by the processor 300 in accordance with instructions stored as applications software in the memory 301 and/or input commands received from a user via the I/O device 302, or commands received from the client device 203.

It will also be assumed that the user interacts with the processing system 210 via a GUI (Graphical User Interface), or the like presented on the client device 203, and in one particular example via a browser application that displays webpages hosted by the base station 201, or an App that displays data supplied by the processing system 210. Actions performed by the client device 203 are performed by the processor 400 in accordance with instructions stored as applications software in the memory 401 and/or input commands received from a user via the I/O device 402.

However, it will be appreciated that the above described configuration assumed for the purpose of the following examples is not essential, and numerous other configurations may be used. It will also be appreciated that the partitioning of functionality between the client devices 203, and the base station 201 may vary, depending on the particular implementation.

Figure 5:
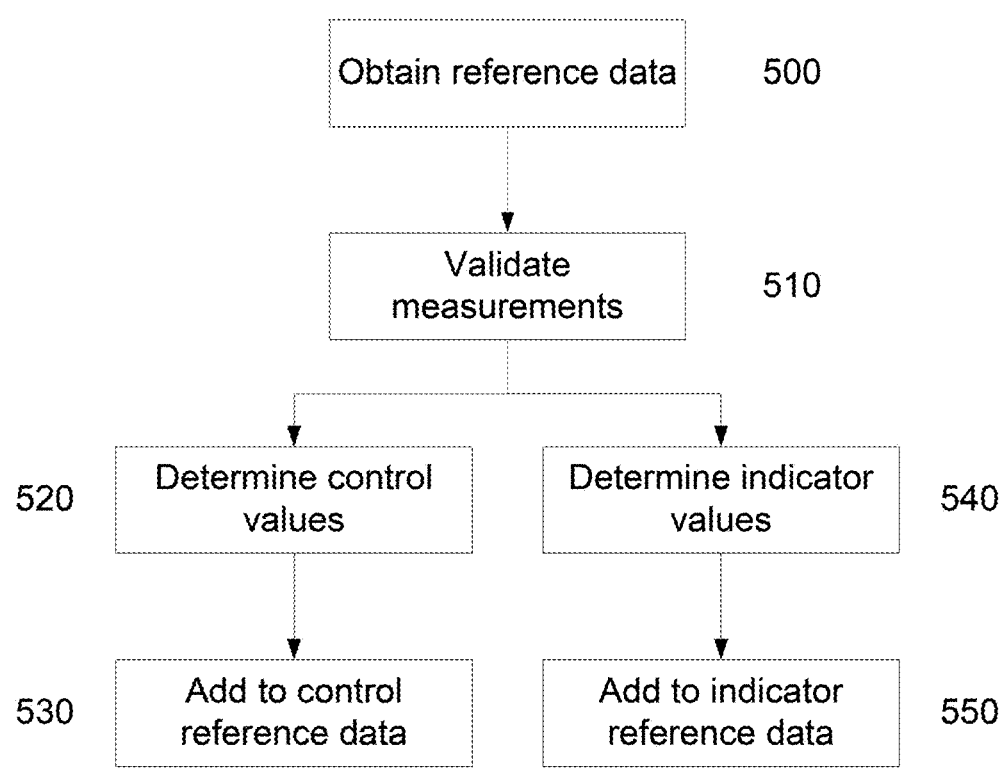
FIG. 5 is a flowchart of an example of a method for validating an indicator derived from biomarker measurements and corresponding reference distributions.

An example process for establishing control and indicator references will now be described in more detail with reference to FIG. 5.

In this example, at step 500 the processing system 210 determines reference data in the form of biomarker values obtained for a reference population.

A reference population is any population of interest for which information is collected against which reference can be made. For example the population may be characterized into those with or without a condition, or with varying degrees of severity, prognosis, stage, or similar disease or condition stratification method.

The reference data may be acquired in any appropriate manner but typically this involves obtaining gene expression product data from a plurality of individuals, selected to include individuals diagnosed with one or more conditions of interest, as well as healthy individuals. The terms "expression" or "gene expression" refer to production of RNA only or production of RNA and translation of RNA into proteins or polypeptides. In specific embodiments, the terms "expression" or "gene expression" refer to production of messenger RNA (mRNA), ribosomal RNA (rRNA), microRNA (miRNA) or other RNA classes such mitochondrial RNA (mtRNA), non-coding RNA (ncRNA, lncRNA (long)), small interfering RNA (siRNA), transfer RNA (tRNA) or proteins.

As used herein, the terms "microRNA" or "miRNA" refer to a short ribonucleic acid (RNA) approximately 18-30 nucleotides in length (suitably 18-24 nucleotides, typically 21-23 nucleotides in length) that regulates a target messenger RNA (mRNA) transcript post-transcriptionally through binding to the complementary sequences on the target mRNA and results in the degradation of the target mRNA. The terms also encompass the precursor (unprocessed) or mature (processed) RNA transcript from a miRNA gene. The conversion of precursor miRNA to mature miRNA is aided by RNAse such as Dicer, Argonaut, or RNAse III.

The conditions captured in the reference data are typically medical, veterinary or other health status conditions and may include any illness, disease, stages of disease, disease subtypes, seventies of disease, diseases of varying prognoses, or the like.

Example reference biomarkers could include expression products such as nucleic acid or proteinaceous molecules, as well as other molecules relevant in making a clinical assessment.

The individuals in the reference population also typically undergo a clinical assessment allowing any conditions to be clinically identified as part of the characterization process for the reference population, and with an indication of any assessment or condition forming part of the reference data. Whilst any conditions can be assessed, in one example the process is utilized specifically to identify conditions such as SIRS (Systemic Inflammatory Response Syndrome) (M S Rangel-Frausto, D Pittet, M Costigan, T Hwang, C S Davis, and R P Wenzel, "The Natural History of the Systemic Inflammatory Response Syndrome (SIRS). a Prospective Study.," *JAMA: the Journal of the American Medical Association* 273, no. 2 (Jan. 11, 1995): 117-123.). SIRS is an overwhelming whole body reaction that may have an infectious or non-infectious aetiology, whereas sepsis is SIRS that occurs during infection. Both are defined by a number of non-specific host response parameters including changes in heart and respiratory rate, body temperature and white cell counts (Mitchell M Levy et al., "2001 SCCM/ESICM/ACCP/ATS/SIS International Sepsis Definitions Conference," *Critical Care Medicine* 31, no. 4 (April 2003): 1250-1256.; K Reinhart, M Bauer, N C Riedemann, and C S Hartog, "New Approaches to Sepsis: Molecular Diagnostics and Biomarkers," *Clinical Microbiology Reviews* 25, no. 4 (Oct. 3, 2012): 609-634). To differentiate these conditions they are referred herein to as SIRS (both conditions), infection-negative SIRS (SIRS without infection, hereafter referred to as "inSIRS") and infection-positive SIRS (sepsis, SIRS with a known or suspected infection, hereafter referred to as "ipSIRS"). The causes of SIRS are multiple and varied and can include, but are not limited to, trauma, burns, pancreatitis, endotoxaemia, surgery, adverse drug reactions, and infections (local and systemic). It will be appreciated from the following, however, that this can be applied to a range of different conditions, and reference to inSIRS or ipSIRS is not intended to be limiting.

Additional reference data may also be collected for the reference population and may include additional biomarkers such as one or more phenotypic or clinical parameters of the individuals and/or their relatives that has not been generated or captured by instrument measurements or a clinical assessment. Phenotypic parameters can include information such as the gender, ethnicity, age, hair colour, eye colour, height, weight, waist and hip circumference, or the like. Also, in the case of the technology being applied to individuals other than humans, this can also include information such as designation of a species, breed or the like. Clinical traits may include genetic information, white blood cell count, diastolic blood pressure and systolic blood pressure, bone density, body-mass index, presence of diabetes or not, resting heart rate, HOMA (homeostasis model assessment), HOMA-IR (homeostasis model assessment insulin resistance), IVGT (intravenous glucose tolerance test), resting heart rate, β cell function, macrovascular function, microvascular function, atherogenic index, low-density lipoprotein/high-density lipoprotein ratio, intima-media thickness, body temperature, Sequential Organ Failure Score (SOFA) and the like.

The reference population has two functions, the first is to characterize patients with respect to the condition of interest, in this example categorize patients into inSIRS and ipSIRS. The second is to capture the values required to generate values used in the assay. Thus, for a reference population and for a specific indicator, application of the indicator to the reference data will produce a reference indicator distribution of values corresponding to known categories or degrees such as inSIRS and ipSIRS, against which indicator values determined from new samples can be compared.

Similarly, internal relative controls can be generated using the reference population data and compared to internal relative controls similarly generated for each new sample.

Each individual within the reference population is typically allocated to a group. The groups may be defined in any appropriate manner such as any one or more of an indication of a presence, absence, degree, stage, severity, prognosis or progression of a condition, other tests or assays, or measured biomarkers associated with the individuals.

For example, a first selection of groups may be used to identify one or more groups of individuals suffering from SIRS, one or more groups of individuals suffering ipSIRS, and one or more groups of individuals suffering inSIRS. Further groups may also be defined for individuals suffering from other conditions. The groups may include overlapping groups, so for example it may be desirable to define groups of healthy individuals and individuals having SIRS, with further being defined to distinguish inSIRS patients from ipSIRS patients, as well as different degrees of inSIRS or ipSIRS, with these groups having SIRS in common, but each group of patients differing in whether a clinician has determined the presence of an infection or not. Additionally, further subdivision may be performed based on phenotypic traits, so groups could be defined based on gender, ethnicity or the like so that a plurality of groups of individuals suffering from a condition are defined, with each group relating to a different phenotypic trait.

It will also be appreciated, however, that identification of different groups can be performed in other manners, for example on the basis of particular activities or properties of biomarkers within the biological samples of the reference individuals and accordingly, reference to conditions is not intended to be limiting and other information may be used as required.

The manner in which classification of patients in the reference population into groups is performed may vary depending on the preferred implementation. In one example, this can be performed automatically by the processing system 201, for example, using unsupervised methods such as Principal Components Analysis (PCA), or supervised methods such as k-means or Self Organising Map (SOM). Alternatively, this may be performed manually by an operator by allowing the operator to review reference data presented on a Graphical User Interface (GUI), and define respective groups using appropriate input commands.

Accordingly, in one example the reference data can include for each of the reference individuals information relating to at least one and desirably to a plurality of reference biomarkers and a presence, absence, degree or progression of a condition.

The reference data may be collected from individuals presenting at a medical centre with clinical signs relating to any relevant conditions of interest, and may involve follow-on consultations in order to confirm clinical assessments, as well as to identify changes in biomarkers, and/or clinical signs, and/or severity of clinical signs, over a period of time. In this latter case, the reference data can include time series data indicative of the progression of a condition, and/or the activity of the reference biomarkers, so that the reference data for an individual can be used to determine if the condition of the individual is improving, worsening or static. It will also be appreciated that the reference biomarkers are preferably substantially similar for the individuals within the sample population, so that comparisons of measured activities between individuals can be made.

This reference data could also be collected from a single individual over time, for example as a condition within the individual progresses, although more typically it would be obtained from multiple individuals each of which has a different stage of the one or more conditions of interest.

It will be appreciated that once collected, the reference data can be stored in the database 211 allowing this to be subsequently retrieved by the processing system 210 for subsequent analysis, or could be provided directly to the processing system 210 for analysis.

In one example, the measurements are received as raw data, which then undergoes preliminary processing. Such raw data corresponds to information that has come from a source without modification, such as outputs from instruments such as PCR machines, array (e.g., microarray) scanners, sequencing machines, clinical notes or any other biochemical, biological, observational data, or the like. This step can be used to convert the raw data into a format that is better suited to analysis. In one example this is performed in order to normalise the raw data and thereby assist in ensuring the biomarker values demonstrate consistency even when measured using different techniques, different equipment, or the like. Thus, the goal of normalisation is to remove the variation within the samples that is not directly attributable to the specific analysis under consideration. For example, to remove variances caused by differences in sample processing at different sites. Examples of normalisation that are well known in the art include z-score transformation for generic data, or popular domain specific normalisations, such as RMA normalisation for microarrays.

However, it will also be appreciated that in some applications, such as a single sample experiment run on a single data acquisition machine, this step may not strictly be necessary, in which case the function can be a Null function producing an output identical to the input.

In one example, the preferred approach for generating reference data is a paired function approach over log normalised data. Log normalisation is a standard data transformation on gene and protein expression data, because the measured biomarkers follow a log-normal distribution as directly measured by the instrument. Applying a log transform turns the data into process-friendly normally distributed data. The biomarker values measured will depend on the predominant condition that is being assessed so, for example, in the case of determining the likelihood of a subject having ipSIRS as opposed to inSIRS, the RNA biomarkers $Bm_1$, $Bm_2$, $Bm_3$, $Bm_4$ used could be LAMP1, CEACAM4, PLAC8 and PLA2G7. A second possible example, in the case of determining the likelihood of a subject having liver disease, the protein biomarkers $Bm_1$, $Bm_2$, $Bm_3$, $Bm_4$ used could be Alkaline Phosphatase (AP), Aminotransferase (AT), Aspartate Aminotransferase (AspAT) and Gamma-glutamyl transpeptidase (GGT).

As part of the above process, at step 510 the measurements are validated using traditional prior art techniques, to ensure that the measurements have been performed successfully, and hence are valid.

At step 520 at least four internal relative control values $Ctrl_1$, $Ctrl_2$, $Ctrl_3$, $Ctrl_4$, are determined for the reference population, with two additional control values $Ctrl_5$, $Ctrl_6$, being optionally determined as follows:

$$Ctrl_1=(Bm_1/Bm_3)$$

$$Ctrl_2=(Bm_1/Bm_4)$$

$$Ctrl_3=(Bm_2/Bm_3)$$

$$Ctrl_4=(Bm_2/Bm_4)$$

$$Ctrl_5=(Bm_1/Bm_2)$$

$$Ctrl_6=(Bm_3/Bm_4)$$

At step 530, the control values used to update or create respective control reference data. In this regard, in the current example, each control reference is in the form of a distribution of control values for the reference population including healthy individuals and individuals suffering from the conditions of interest. The distribution itself can be used as a control reference, or alternatively one or more values could be derived therefrom, such as to define a threshold range. For example this could be set to encompass 99% of the distribution.

Additionally, the control reference could be defined so that it is specific to characteristics of the individuals, such as the sex, ethnicity, age, weight, height or other physical characteristic of the subject, thereby allowing different control references to be defined for different groups of individuals with similar characteristics.

Once created the control references and in particular the control distributions, are stored in the database 211 for subsequent use.

At step 540, first and second indicator values are determined. The first and second indicator values $In_1$, $In_2$ are determined on a basis of ratios of first and second, and third and fourth biomarker values respectively:

$$In_1=(Bm_1/Bm_2)$$

$$In_2=(Bm_3/Bm_4)$$

The indicator values used to update or create a set of indicator references at step 550, which is used in analysing measured indicator values for a subject to establish a likelihood of the subject having a condition. In particular, indicator values for each reference group are statistically analysed to establish a range or distribution of indicator values that is indicative of each group, thereby allowing the indicator values to be used to discriminate between the different groups, and hence ascertain the likelihood a subject is suffering from a particular condition, as will be described in more detail below.

An example process of a process for validating measurement of biomarker values used in generating an indicator will now be described in more details with reference to FIG. 6.

In this example, at step 600 values of four biomarkers $Bm_1$, $Bm_2$, $Bm_3$, $Bm_4$ are measured by the measuring device 205. The four biomarker values selected will depend on the predominant condition that is being assessed. For example, in the case of determining the likelihood of a patient having ipSIRS as opposed to inSIRS, the biomarkers $Bm_1$, $Bm_2$, $Bm_3$, $Bm_4$ used will be LAMP1, CEACAM4, PLAC8 and PLA2G7.

At step 610 the processing system 210 determines first and second indicator values, either directly from the measuring device 205, or by retrieving the values after storage in a database 211 or other data store. The first and second indicator values $In_1$, $In_2$ are determined on a basis of ratios of first and second, and third and fourth biomarker values respectively:

$$In_1=(Bm_1/Bm_2)$$

$$In_2=(Bm_3/Bm_4)$$

At step 620 the processing device 210 combines the indicator values to determine an indicator In which may be achieved utilising a sum of the first and second indicator values or other similar measure. So for example:

$$In=In_1+In_2=(Bm_1/Bm_2)+(Bm_3/Bm_4)$$

At step 630, the processing device 210 determines the four control values $Ctrl_1$, $Ctrl_2$, $Ctrl_3$, $Ctrl_4$, and optionally additional control values $Ctrl_5$, $Ctrl_6$, as follows:

$$Ctrl_1=(Bm_1/Bm_3)$$

$$Ctrl_2=(Bm_1/Bm_4)$$

$$Ctrl_3=(Bm_2/Bm_3)$$

$$Ctrl_4=(Bm_2/Bm_4)$$

$$Ctrl_5=(Bm_1/Bm_2)$$

$$Ctrl_6=(Bm_3/Bm_4)$$

Figure 6:
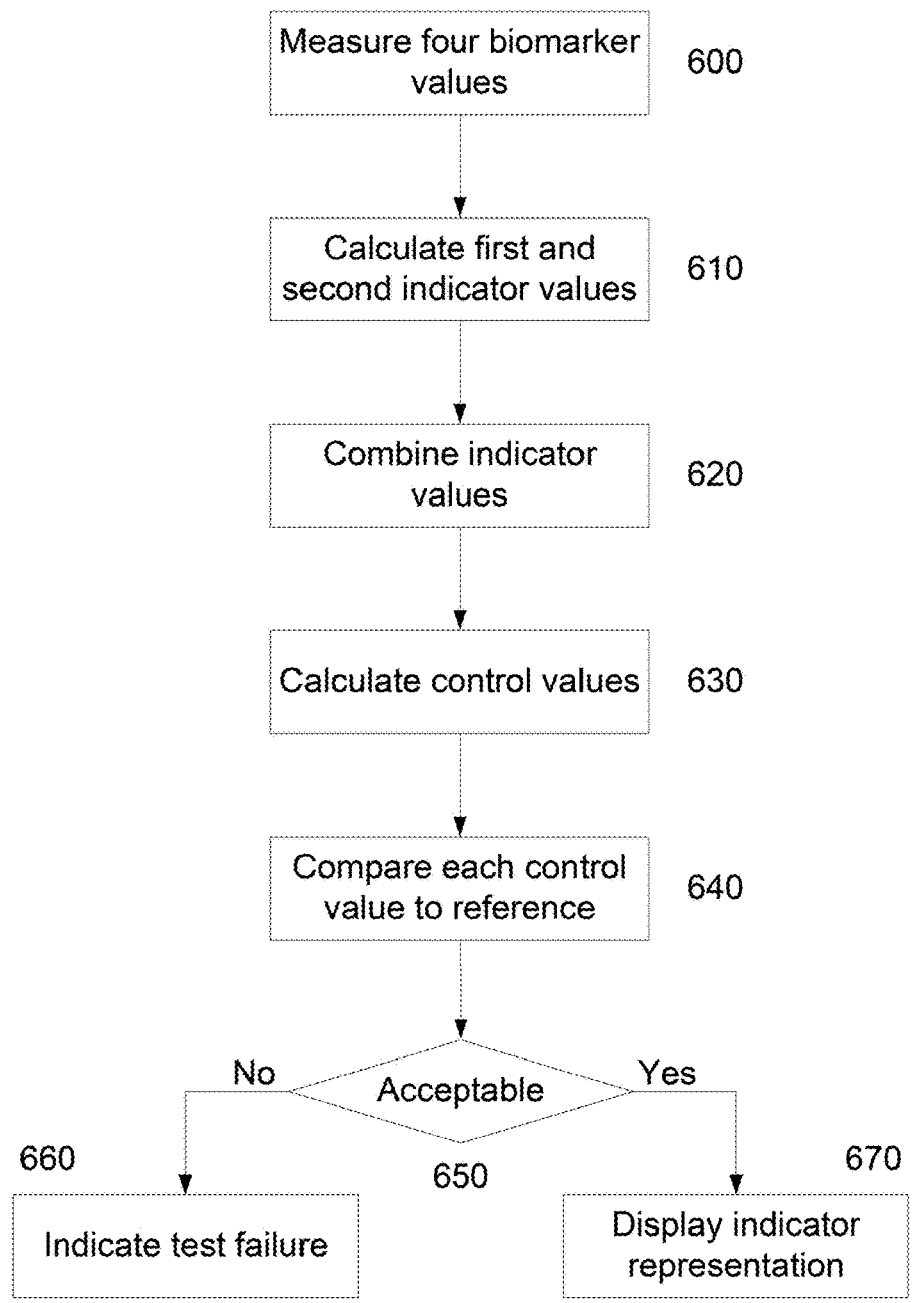
FIG. 6 is a flowchart of an example of a method for validating an indicator derived from biomarker measurements.

Thus, as shown in FIG. 6, each possible ratio of the values of the four biomarkers $Bm_1$, $Bm_2$, $Bm_3$, $Bm_4$ is calculated, with two of the ratios being used to form the indicator values and hence the indicator, and all of the ratios being used for control values.

Each of the control values is then compared to a respective control reference, and in particular control distribution, at step 640. In this regard, it will be appreciated that the processing system 210 will retrieve respective control distributions for the particular biomarkers that are used to determine the respective control values $Ctrl_1$, $Ctrl_2$, $Ctrl_3$, $Ctrl_4$, optionally additional control values $Ctrl_5$, $Ctrl_6$ with these control distributions being previously determined and stored in the database 211, as described above. At step 650, the processing system 210 determines if each control value is acceptable based on the results of the comparison. In this regard, if any one control value is outside the defined control value threshold range, then this is indicative of a test failure which is communicated to the user at step 660, for example by providing an indication on a client device 203 of a medical practitioner requesting the test. Otherwise a representation of the indicator is displayed at step 670 on the client device 203, as will be described in more detail below.

In the above described process, the values of the four biomarkers $Bm_1$, $Bm_2$, $Bm_3$, $Bm_4$ are used to determine four (or optionally six) control values. Because each biomarker ($Bm_1$, $Bm_2$, $Bm_3$, $Bm_4$) is involved in multiple comparisons with other biomarkers as controls ($Ctrl_1$, $Ctrl_2$, $Ctrl_3$, $Ctrl_4$), there are more opportunities for detection of an invalid underlying biomarker than if each biomarker was measured against only a single expected range or against a single control biomarker. This multiple testing of each biomarker results in far greater sensitivity than would be achieved with individual comparison to an independent control, as shown in the arrangement of FIG. 7B.

Figure 7A:
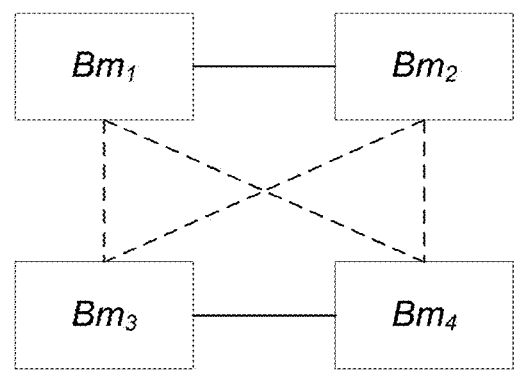
FIG. 7A is schematic diagram of an indication of the relationship of biomarker values in the process of FIG. 5.
Figure 7B:
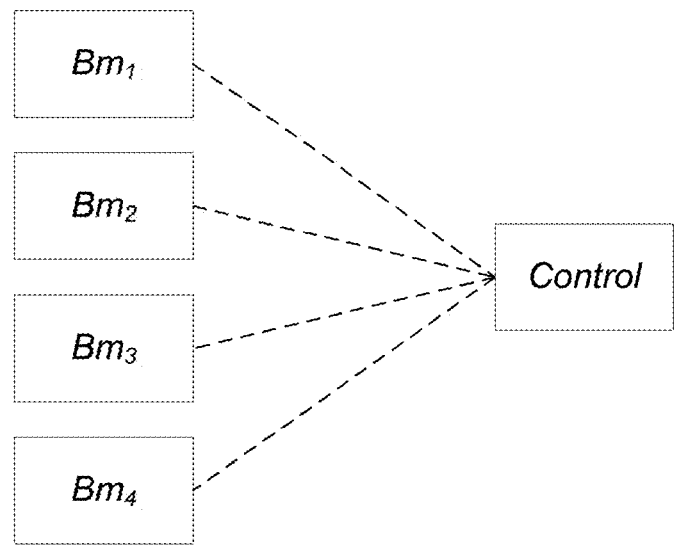
FIG. 7B is schematic diagram of an indication of the relationship of biomarker values to a control in a standard control arrangement.

For example, in the case of FIG. 7B, representing a standard control strategy based on measured biomarkers, $Bm_1$ is measured relative to the control, or equivalently to an absolute value using the control to derive the value. The measured value being outside an expected range is only seen once in every thousand samples, so if the measured value falls outside of this range, the probability that this sample measurement belongs to the distribution (that is, it is valid) is therefore 1/1000 and p value for failure detection: 0.001.

In contrast in the case of the current system of FIG. 7A, the measured value of biomarker $Bm_1$ is compared to each of biomarkers $Bm_2$, $Bm_3$, $Bm_4$. Each represents an independent check on the measured value of $Bm_1$, so values outside the range are only once every 1000 samples for each comparison. The probability that this sample is not in the distribution of valid samples (a failure) is 1/1000×1/1000× 1/1000, so that the p value for failure detection: 1e-9, meaning this relative control combination shown in FIG. 7A is a million times more sensitive than a standard measured control shown in FIG. 7B.

Figure 8A:
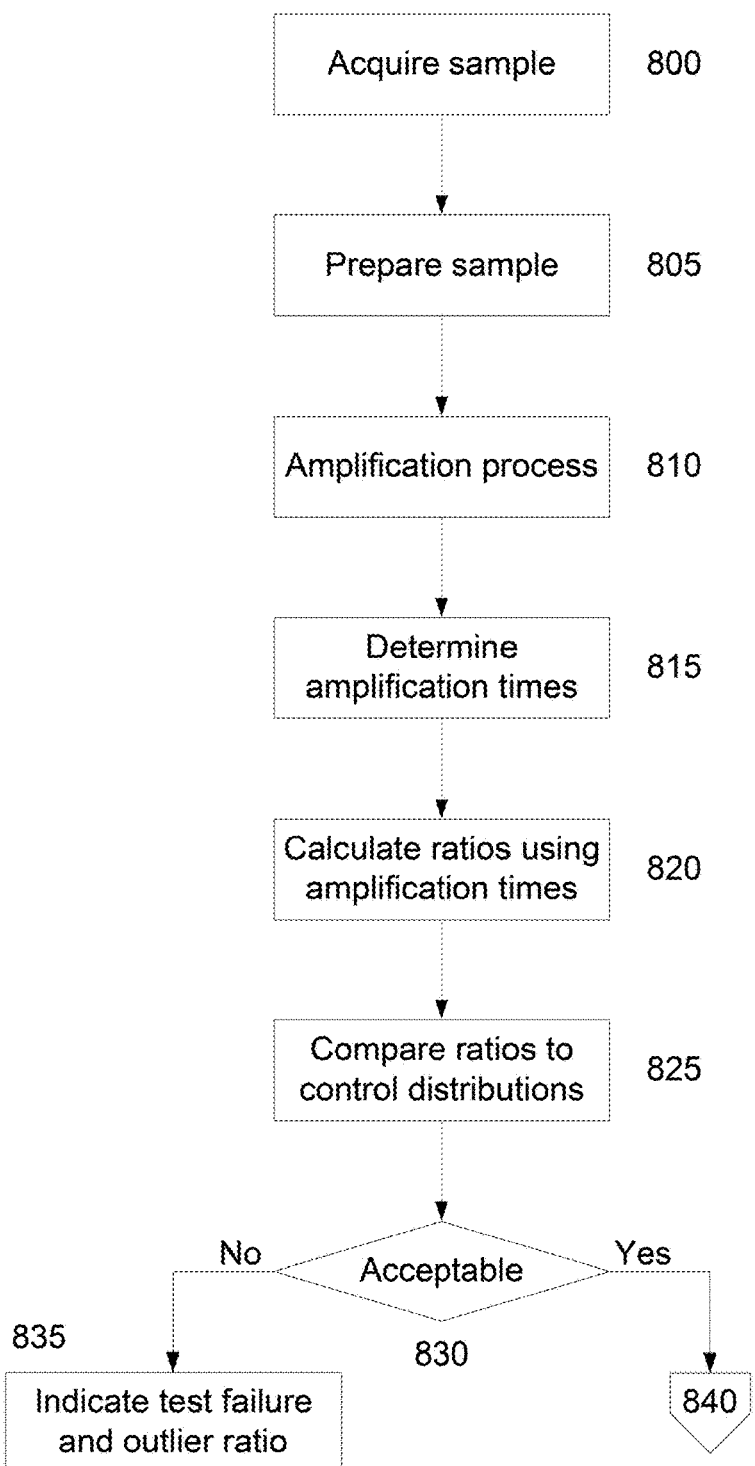
FIGS. 8A and 8B are a flowchart of an example of a method for validating an indicator derived from biomarker measurements.
Figure 8B:
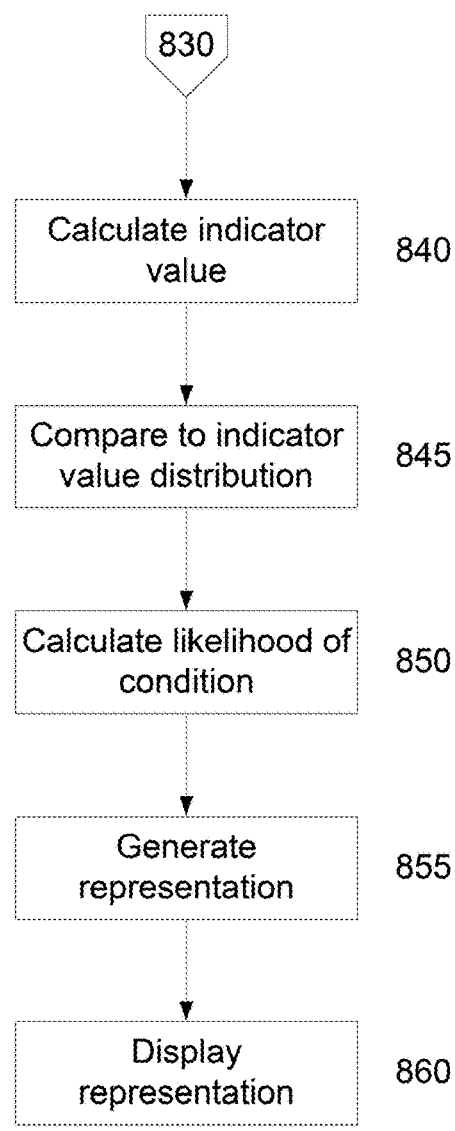

A further example will now be described with reference to FIGS. 8A and 8B.

In this example, at step 800 a sample is acquired from the subject. The sample could be any suitable sample such as a peripheral blood sample, or the like, depending on the nature of the biomarker values being determined. At step 805 the sample undergoes preparation allowing this to be provided to the measuring device 205 and used in a quantification process at step 810. For the purpose of this example, the quantification process involves PCR amplification, with the measuring device being a PCR machine, although other suitable biomarker measurement devices and techniques could be used. In this instance, amplifications times $At_1$, $At_2$, $At_3$, $At_4$, are determined for each of the four biomarkers $Bm_1$, $Bm_2$, $Bm_3$, $Bm_4$ at step 815, with the amplification times being transferred from the measuring device 205 to the processing system 210 allowing the processing system 210 to perform analysis of the corresponding biomarker values.

Accordingly, at step 820 the processing system 210 calculates ratios using the amplifications times. In this regard, as the amplification times represent a log value, the ratios are determined by subtracting amplifications times as will be appreciated by a person skilled in the art.

Accordingly, in this example the indicator and control values would be determined as follows:

$Ctrl_1 = (\text{Log } Bm_1 - \text{Log } Bm_3) = (At_1 - At_3)$ $Ctrl_2 = (\text{Log } Bm_1 - \text{Log } Bm_4) = (At_1 - At_4)$ $Ctrl_3 = (\text{Log } Bm_2 - \text{Log } Bm_3) = (At_2 - At_3)$ $Ctrl_4 = (\text{Log } Bm_2 - \text{Log } Bm_4) = (At_2 - At_4)$ As previously mentioned, the indicator values can also be used as control values, leading to two further control valves:

$Ctrl_5 = (\text{Log } Bm_1 - \text{Log } Bm_2) = (At_1 - At_2)$ $Ctrl_6 = (\text{Log } Bm_3 - \text{Log } Bm_4) = (At_3 - At_4)$ The processing system compares the ratios representing the control values to respective control value threshold ranges retrieved from the database 211, at step 825. Again, this can be based on characteristics of the subject, with the control values being derived from control values measured for a sample population of individuals with similar characteristics.

At step 830, the processing system 210 determines if the control ratios correspond to control values that are acceptable, in other words if they fall within the defined threshold range. If this is not the case then test failure is indicated, for example, by having the processing system 210 generate a failure notification and provide this to a client device 205 at step 835. The notification could be of any suitable form and could include an email, notification in a dash board of a test management software application or the like. As part of this, any outlier ratios that fall outside the control value ranges can be identified, allow an operator to identify which if any of the biomarker values failed or was inaccurately measured for any reason.

In the event that each of the control values are acceptable, at step 840 the processing system 210 determines an indicator value by combining the ratios for the indicator values, as follows:

$In = (\text{Log } Bm_1 - \text{Log } Bm_2) + (\text{Log } Bm_3 - \text{Log } Bm_4) = (At_1 - At_2) + (At_3 - At_4)$ The processing system 210 then compares the indicator value to one or more respective indicator thresholds at step 845.

As previously described, the indicator references are derived for a sample population and are used to indicate the likelihood of a subject suffering from ipSIRS or another condition. To achieve this, the indicator reference is typically derived from a sample population having similar characteristics to the subject. The sample population is typically grouped based on a clinical assessment into groups having/not having the conditions or a measure of severity, risk or progression stage of the condition, with this then being used to assess threshold indicator values that can distinguish between the groups or provide a measure of severity, risk or progression stage. The results of this comparison are used by the processing system 210 to calculate a likelihood of the subject having ipSIRS at step 850, with this being used to generate a representation of the results at step 855, which is transferred to the client device 203 for display at step 860, for example as part of an email, dashboard indication or the like.

Figure 9A:
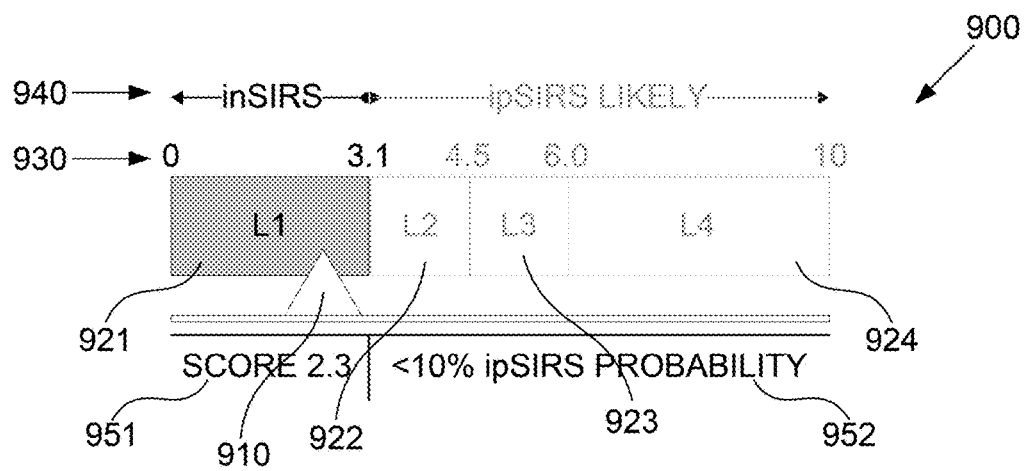
FIGS. 9A and 9B are schematic diagrams of examples of representations of indicator values.
Figure 9B:
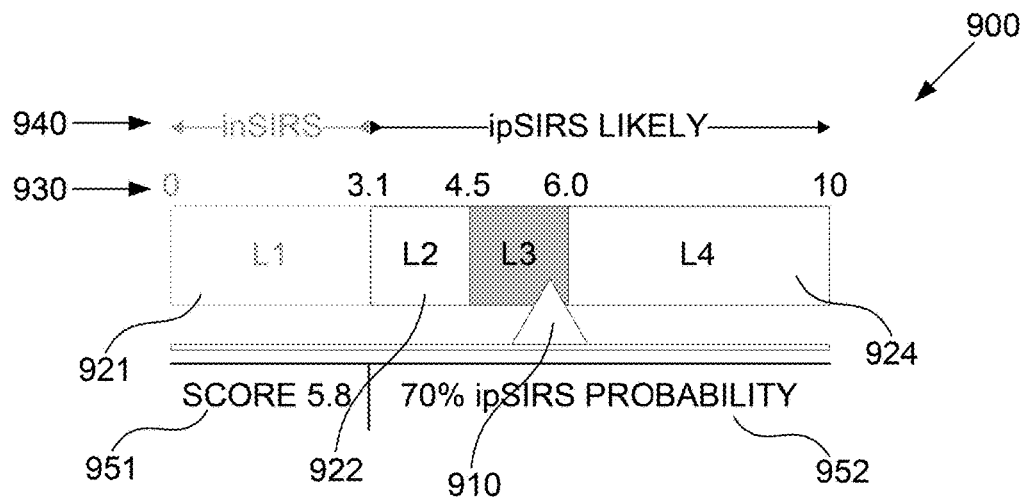

An example of the representation is shown in FIGS. 9A and 9B.

In this example, the representation 900 includes a pointer 910 that moves relative to a linear scale 930. The linear scale is divided into regions 921, 922, 923, 924 which indicates the probability of a subject having either SIRS or sepsis. Corresponding indicator number values are displayed at step 930 with an indication of whether the corresponding value represents a likelihood of inSIRS or ipSIRS being showing at step 940. An alphanumeric indication of the score is shown at step 951 together with an associated probability of the biological subject having ipSIRS at step 952.

As shown in this example, regions of the linear scale where the pointer is situated are highlighted with the diagnosis that is most unlikely being greyed out to make it absolutely clear where the subject sits on the scale. This results in a representation which when displayed at step 860 is easy for a clinician to readily understand and to make a rapid diagnosis.

Features of the benefits of using derived internal controls over prior art will now be described with reference to FIGS. 10A, 10B and 10C.

Figure 10A:
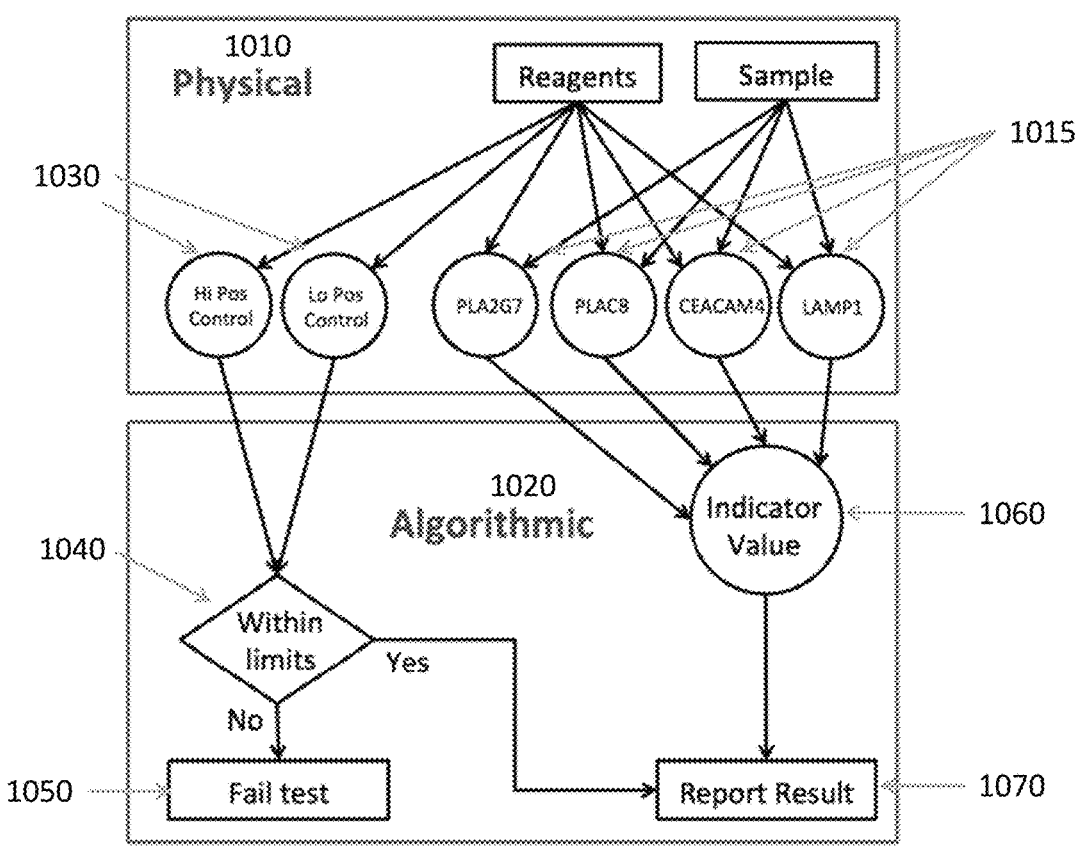
FIG. 10A is a flow chart of an example of the standard use of controls in a multi-biomarker medical device.

Using the above example with four measured biomarkers used in generating the indicator value, a standard control methodology is shown in FIG. 10A. The work flow of the assay is divided up into physical 1010 and algorithmic 1020 components, where the physical components 1010 are inherent hardware, reagents and non-software components and the algorithmic components 1020 are carried out on an appropriate computing device 210. The values of the measured biomarkers 1015 and external measured controls 1030 are generated using the physical device 1010. External positive controls 1030 are used to validate that the test is able to produce a result in the reportable range by measuring against a reference range 1040, and if no, then fail the test 1050, or if yes, output the indicator value 1060 in a report 1070.

Figure 10B:
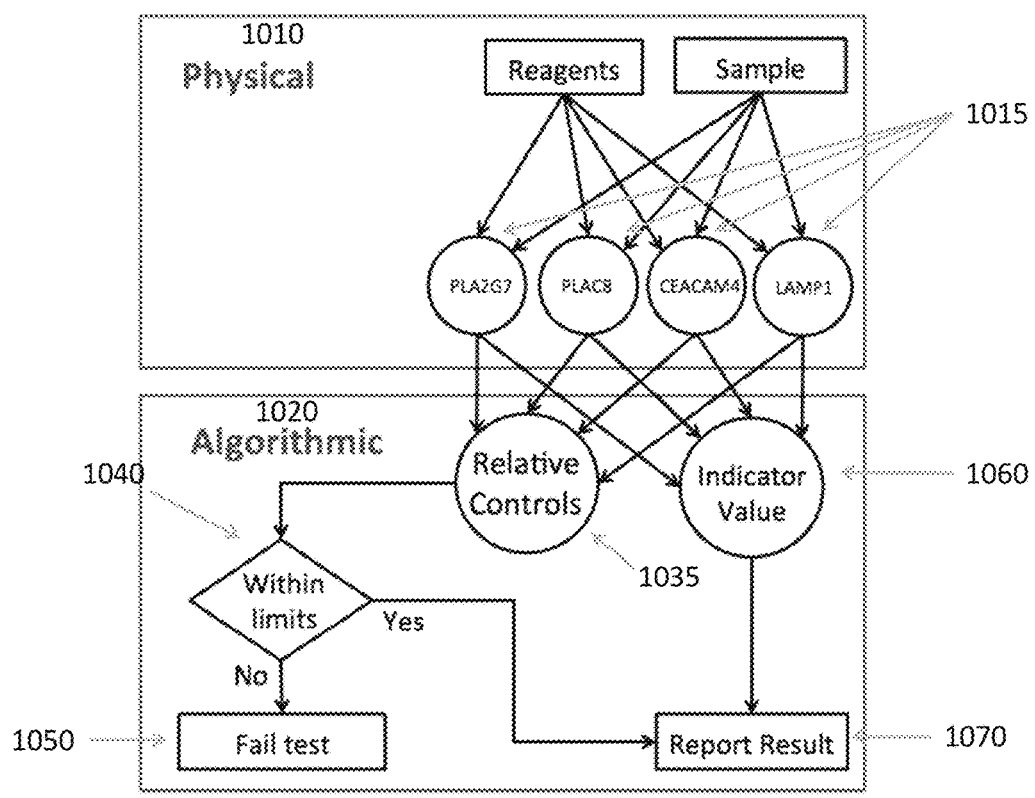
FIG. 10B is a flow chart of an example of the use of relative controls in place of standard controls in a multi-biomarker medical device.

For comparison, the same device using internal relative controls is shown in FIG. 10B. Again the workflow is divided up into physical 1010 and algorithmic 1020 components and the measured biomarkers 1015 are generated on the physical device 1010. Note that the external positive controls 1030 shown in FIG. 10A are not present, and there is an additional generation of internal relative controls 1035 which are derived from the measured biomarkers 1015. Otherwise the two methods are similar with the testing of controls against reference thresholds 1040, and if outside these thresholds a failure of the assay will be reported 1050, else the indicator value 1060 will be output in the form of a report 1070.

It will be appreciated that by removing physical components of a device in the form of external controls 1030, and replacing their function with the use of internal relative controls 1035, the control component of the test has been shifted from a physical component, with fixed costs per unit, to the algorithmic component, which is substantially more scalable as software. Therefore the use of internal relative controls as shown in FIG. 10B has advantages over the use of prior art measured controls FIG. 10A including lower cost, complexity and risk for industrial manufacture or processing risk.

Figure 10C:
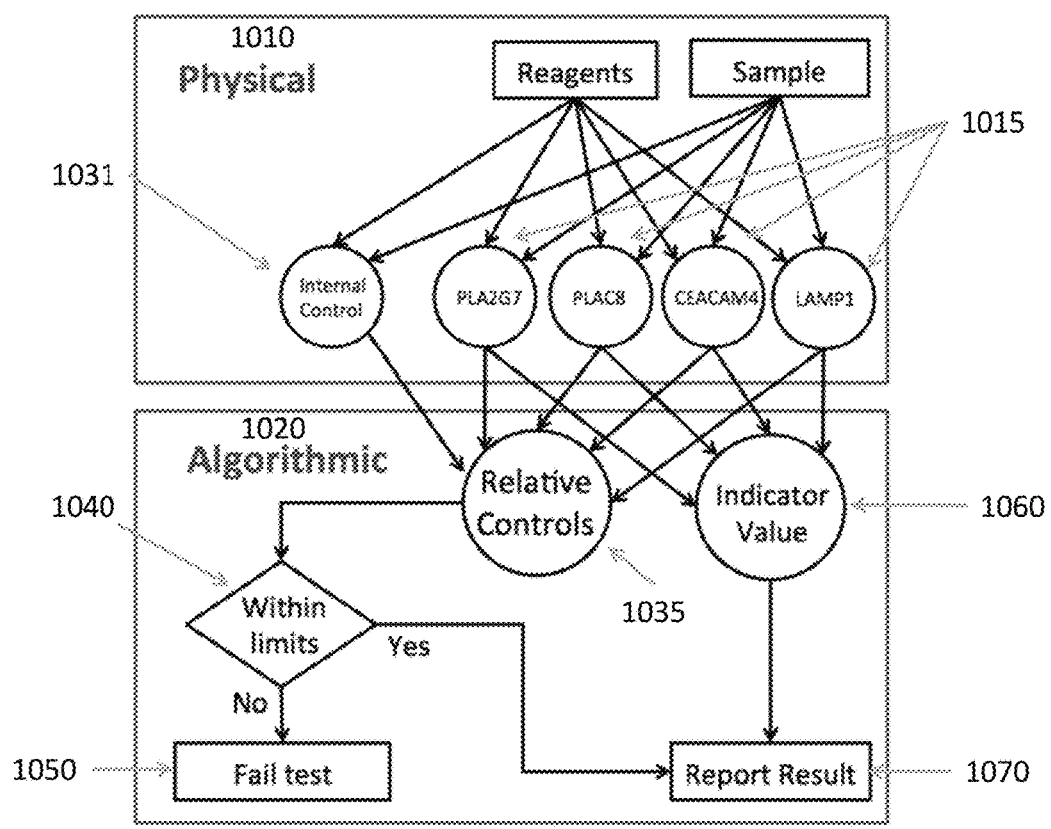
FIG. 10C is a flow chart of an example of the us of a hybrid of standard and relative controls in a multi-biomarker medical device

An extension of this method is example in FIG. 10C, which may be used in the event that the measured biomarkers 1015 are unable or impractical to produce relative controls 1035 that completely cover all instances where a failed sample must be detected 1040. The use of such additional internal relative controls is useful in the case where an indicator value may be invalid even if no combinations of controls comprising the indicator may be out of range. An example may be that a test is designed for use in people with an inflammatory response due to infection, and the indicator value may be a measure of the likelihood that the patient will improve or deteriorate in the following 24 hours. It may be that the indicator is highly prognostic in this population, and that an internal relative biomarker not related to this indicator can reliably distinguish those with and without infection. In this example the internal relative biomarker can be used as an additional control to ensure that the patient is indeed infected, and therefore part of the intended use population, and therefore that the indicator value is valid for use on this patient. In this case an additional measured biomarker 1031 can be run on the physical device 1010 in parallel with the measured biomarkers 1015 that are used for the indicator value 1060. Additional measured biomarkers 1031 need not be used in the indicator value (test result), and are specifically selected to ensure that any invalid samples, when tested for acceptable ranges 1040 will appropriately fail the test 1050. It will be appreciated that multiple additional internal controls 1031 may be required to cover all possible cases of invalid samples and that a plurality of functions may be applied to additional measured internal controls in combination with each other and the measured biomarkers comprising the indicator value to meet this goal. It will further be appreciated that generally it is simpler and cheaper to measure additional internal controls 1031 in a medical device than to use external controls 1030, and therefore even the addition of many internal controls will generally still provide cost and complexity advantages over the use of a small number of external controls.

An example will now be described with reference to FIGS. 12A to 12C, which show kernel density plots for this population. The distribution of Cycle Threshold (Ct) values for each gene is shown in solid lines, and the Ct values for synthesized In-Vitro Transcripts at known concentrations as controls is shown as dashed lines.

Figures 11A, 11B:
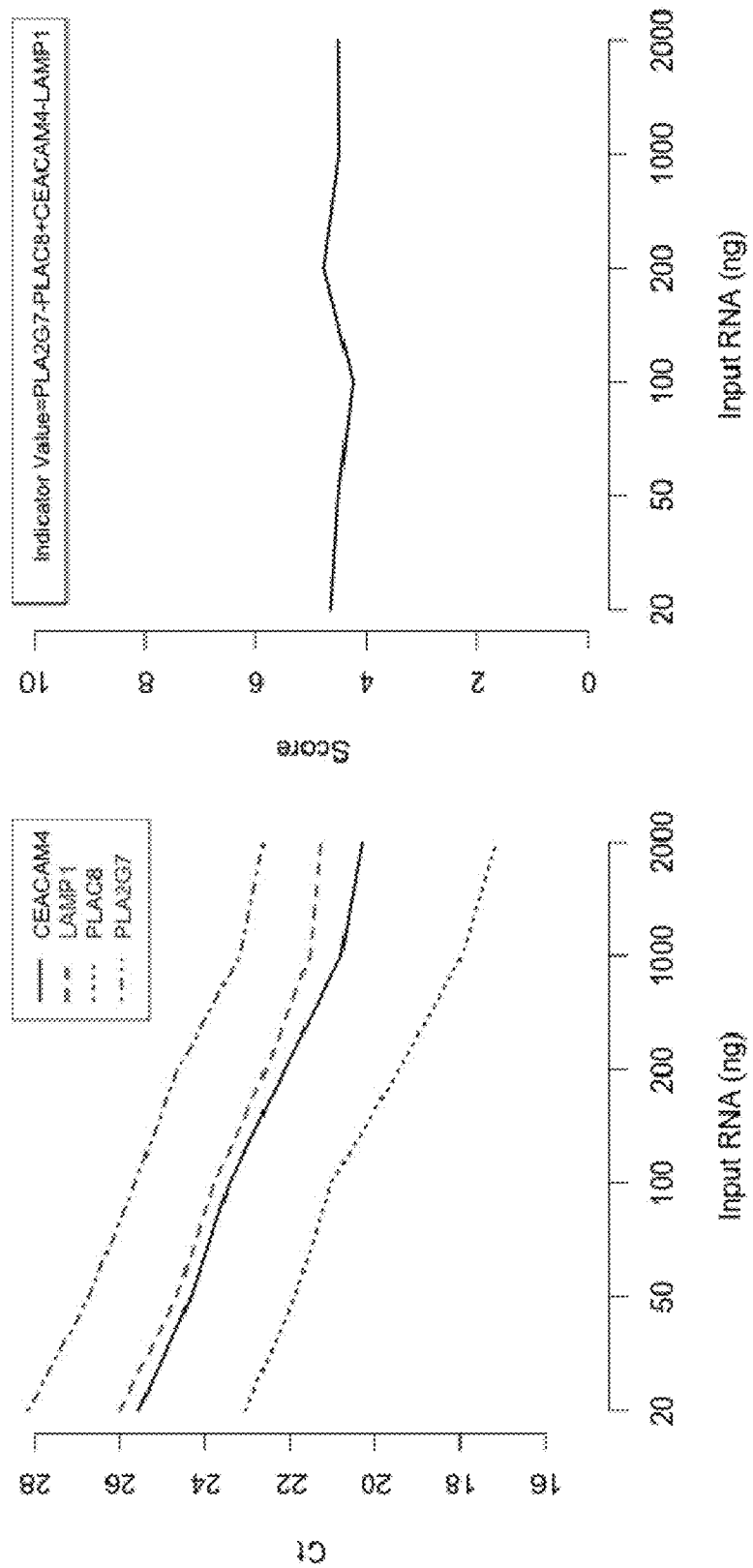
FIG. 11A is plots of cycle times obtained for measured biomarkers over a range of concentrations.
FIG. 11B is plots indicator values for biomarker values derived from the cycle times of FIG. 11A.

Another advantage of the use of relative controls method over standard measured controls will be described with reference to FIGS. 11A and 11B, using the same example. In FIG. 11A, the Ct value for each of the measured biomarkers ($Bm_1$, $Bm_2$, $Bm_3$, $Bm_4$) is shown over a range of concentrations ranging from 20 to 2000 ng input to the PCR reaction. In this example the indicator value is measured as a sum of proportions of these measured biomarkers:

$$In = In_1 + In_2 = (Bm_1/Bm_2) + (Bm_3/Bm_4)$$

The indicator value for these biomarkers at each concentration is shown in FIG. 11B, which shows a flat profile despite very large changes in concentration over the input range. These results demonstrate that the indicator is stable over a range of input concentrations because it measures the relative concentrations between the biomarkers. If a reference threshold (in Ct units) were applied over the stable indicator range (20 to 2000 ng input) to each of the measured biomarkers in FIG. 11A, then the reference ranges would be very wide. In this example, valid ranges for PLAC8 would range from 17 to 23 Ct units. Such wide control reference ranges are generally not appropriate, so typically assays specify a narrow input range so that reference ranges of measured biomarkers can be made sufficiently narrow. This step in creating an input concentration from a sample is an extra step in processing that can be removed if the indicator value uses relative information derived from measured biomarkers, and if the controls also use relative information derived from measured biomarkers. Such an example shows improved utility over controls using measured biomarkers in this case by the removal of a processing step requiring diluting to a specified input concentration, which saves time, cost and reduces complexity.

Figure 12A:
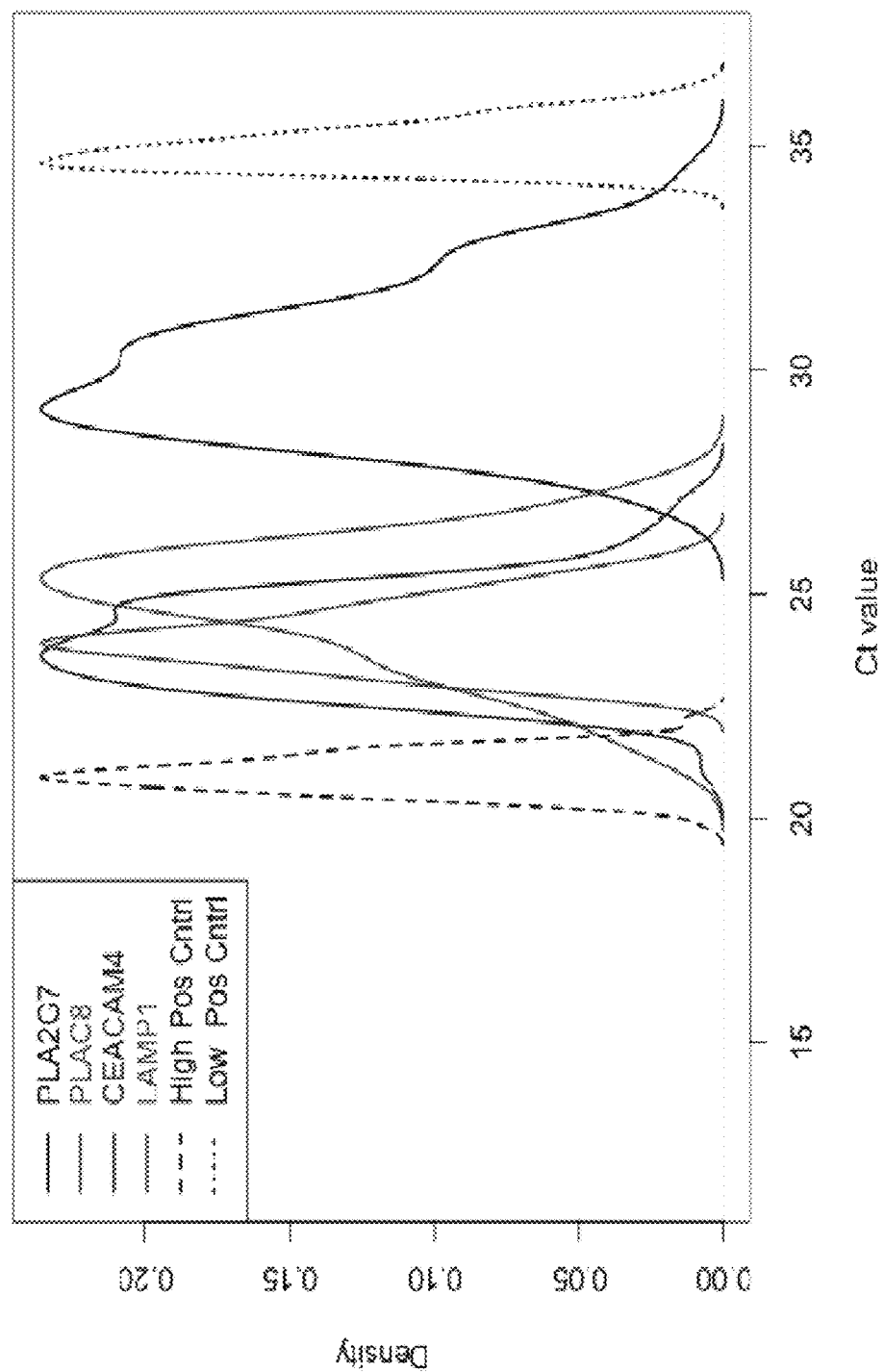
FIG. 12A is a density plot of measured biomarker values for a sample population.
Figure 12B:
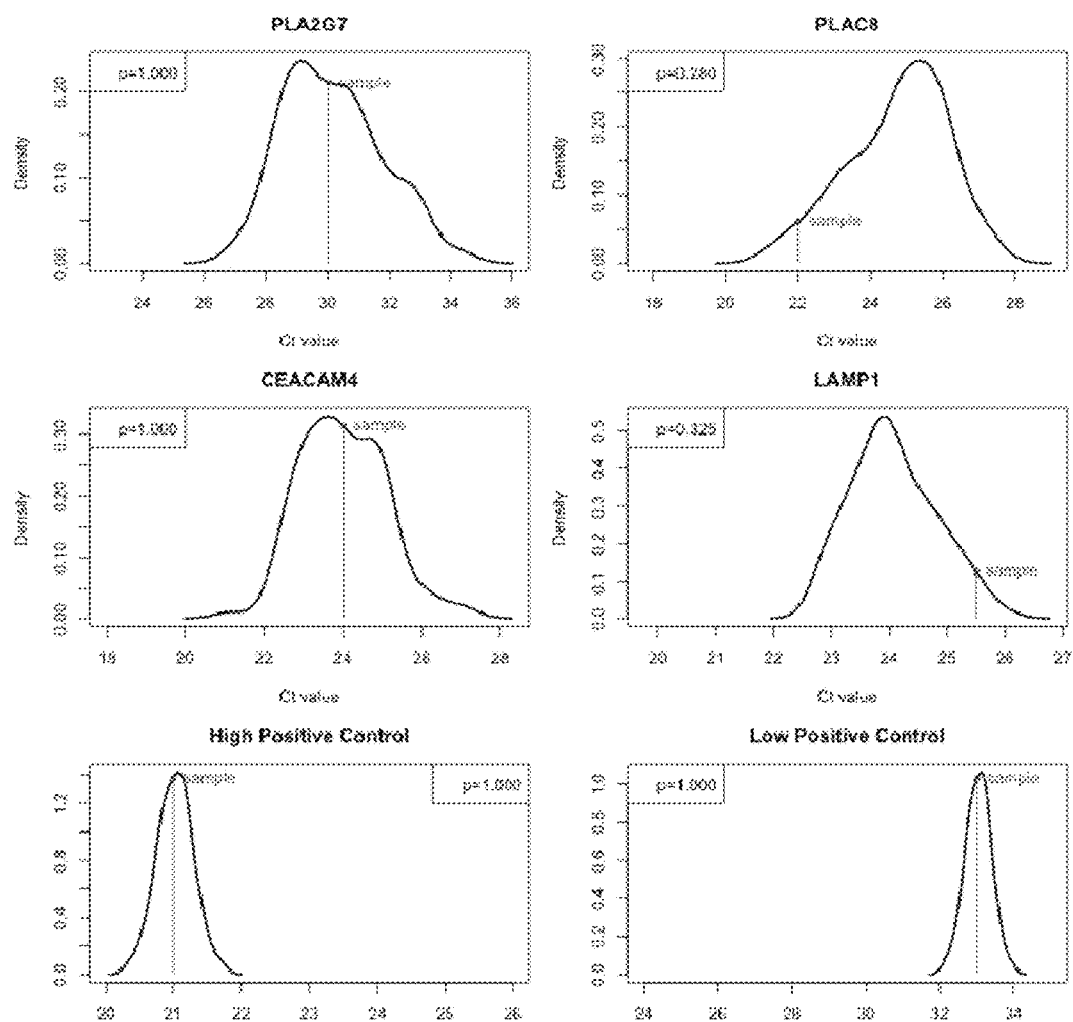
FIG. 12B is a plot of each measured biomarker value for an invalid sample shown against the reference population of measured biomarkers.

In this example, the data shown in FIG. 12A is taken from 106 consecutive samples with 2 or more ipSIRS criteria, divided in patients with or without infection, for biomarkers in the form of signature genes LAMP1, CEACAM4, PLAC8 and PLA2G7.

Next a failure of the measurement of one of the four signature genes will be described. Using sample number 13, and artificially reducing reaction efficiency of the LAMP1 reaction to 89% (failed assay) we reduce the recorded Ct value from 25.71 to 22.88. The probability based on reference Ct observations for this gene that the assay has failed is 32.5% as shown for LAMP1 in FIG. 12B, not sufficient to declare a failed assay. FIG. 12B shows the Ct values recorded for each of the other biomarkers (PLA2G7, PLAC8 and CEACAM4) for the failed sample, and also that for both the high and low positive controls, the values are in the expected ranges.

Table 2 shows that for each of the measured biomarkers and both controls that the values are within the reference ranges and there is not sufficient evidence (p<0.05) to identify the failed sample.

TABLE 2

|  | PLA2G7 | PLAC8 | CEACAM4 | LAMP1 | Hi Pos Cntl | Low Pos Cntl |
| --- | --- | --- | --- | --- | --- | --- |
| Sample Value | 30 | 22 | 24 | 25.5 | 21 | 33 |
| In range | Yes | Yes | Yes | Yes | Yes | Yes |
| P value | 1.000 | 0.280 | 1.000 | 0.325 | 1.00 | 1.00 |

Figure 12C:
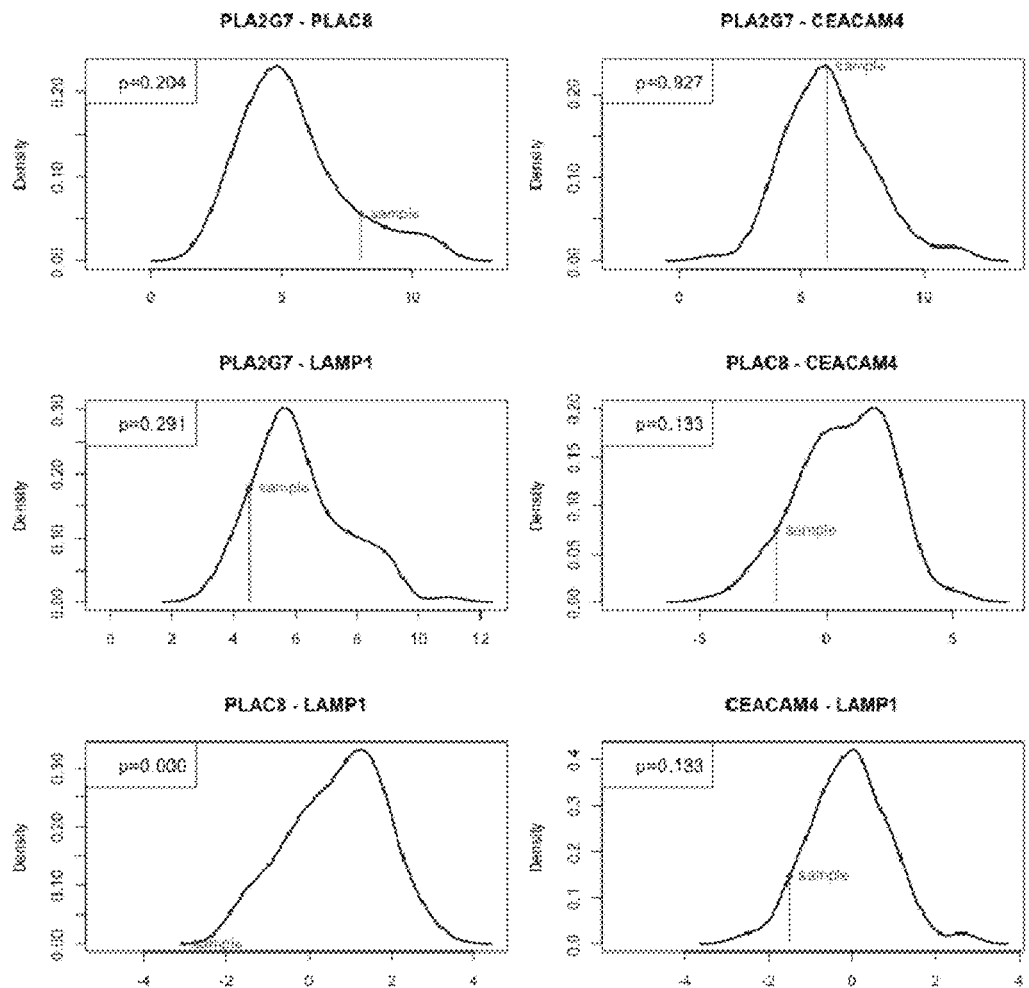
FIG. 12C is a plot of derived control values for an invalid sample shown against the reference derived control values.

Now looking at ratios between the measured biomarkers in FIG. 12C, the ratio PLAC8-LAMP1 clearly detects the failure p<0.001, which is sufficient to correctly declare the assay failed.

Table 3 shows that the failed assay is detected by a low p value (<0.01) for the relative values of PLAC8 to LAMP1.

TABLE 3

|  | PLA2G7-PLAC8 | PLA2G7-CEACAM4 | PLA2G7-LAMP1 | PLAC8-CEACAM4 | PLAC8-LAMP1 | CEACAM4-LAMP1 |
| --- | --- | --- | --- | --- | --- | --- |
| Sample Value | 8 | 6 | 4.5 | −2 | −3.5 | 1.5 |
| In range | Yes | Yes | Yes | Yes | No | Yes |
| P value | 0.204 | 0.927 | 0.291 | 0.133 | <0.001 | 0.133 |

Figure 12D:
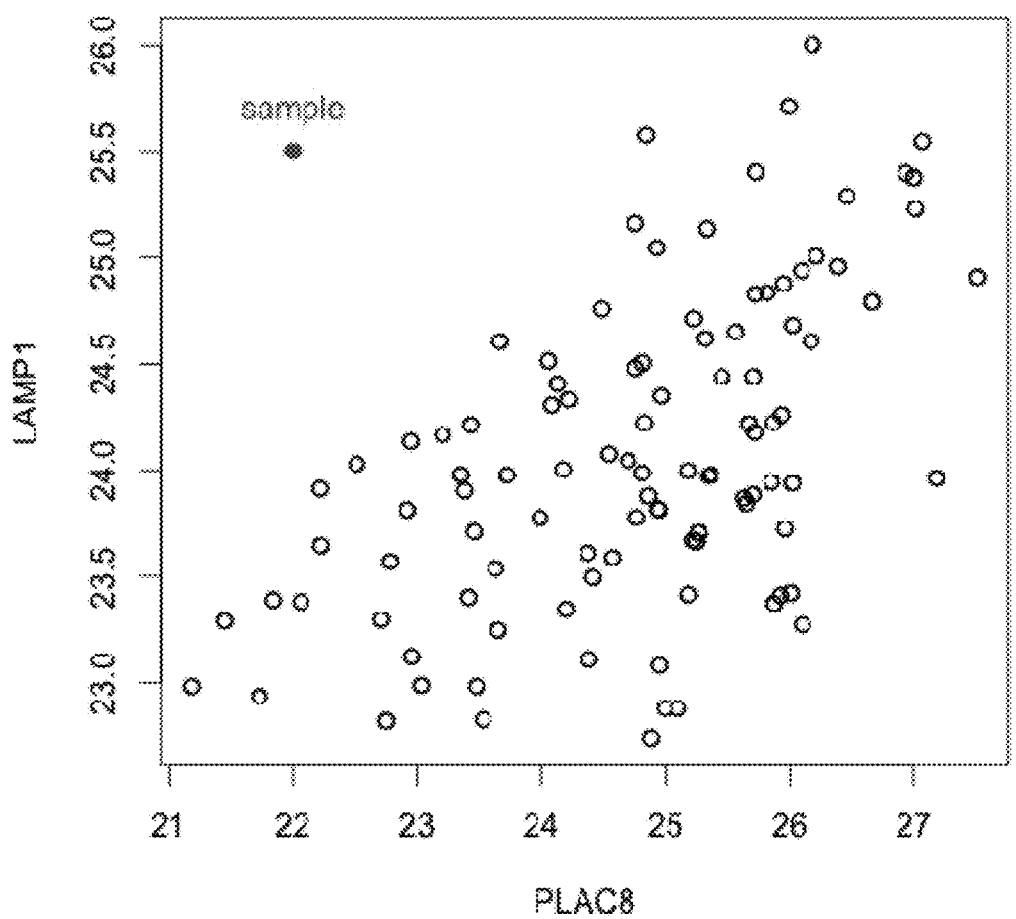
FIG. 12D is a scatterplot showing the invalid sample against one of the reference derived control biomarkers.

FIG. 12D plots the failed sample as a scatterplot of PLAC8 and LAMP1. It can be seen that although this sample is within the maximum and minimum ranges of both PLAC8 and LAMP1, it is a clear outlier when considering the relative position with respect to each of the these biomarkers. This is reflected in the low p value for this relative control, as it is outside of the reference range and thus is correctly identified as a failed sample.

Accordingly, using this approach, multiple relative controls that may not individually be sufficient to declare a failed assay can be combined using a Bayes Rule or other probabilistic method to give a joint probability of failure.

Accordingly, the above process described the use of controls comprised of ratios of measured biomarker values, such as expression of target genes, rather than the use of non-target internal or external controls or spike-ins, in gene expression experiments and analyses. Advantages of such an approach include no additional measurements beyond those used for the indicator values, the ability to analyse more targets in a single experiment and reduced overall costs of performing gene expression analysis in addition to higher sensitivity and the ability to skip an input normalizing step during processing if the indicator values are also comprised of ratios.

Figure 13A:
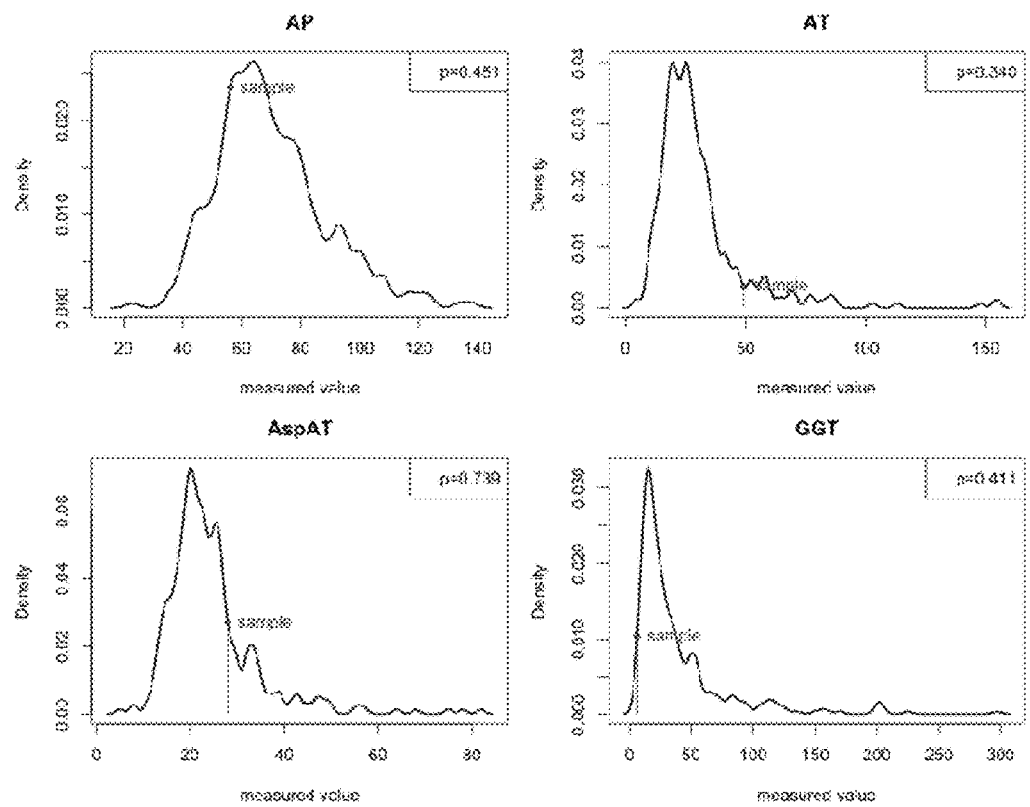
FIG. 13A is a plot showing an invalid sample against a reference population of measured biomarkers.

An example will now be described with reference to FIG. 13A which shows data from BUPA Medical Research Ltd in a study of male patients for the detection of liver damage due to alcoholism. In this study there were 144 enrolled volunteers classified as alcoholic, and 200 enrolled volunteers classified as non-alcoholic. Measurements of liver related proteins from peripheral blood were taken for each volunteer and a diagnostic combination of these proteins (the indicator) for alcohol related liver damage yielded 94% accuracy of classification (Comak, Emre, et al. "A new medical decision making system: Least square support vector machine (LSSVM) with Fuzzy Weighting Pre-processing." *Expert Systems with Applications* 32.2 (2007): 409-414.). The utility of this test is that an accurate diagnosis of liver damage due to alcoholism can be made with a multi-marker protein panel from peripheral blood in preference to an invasive and more expensive liver biopsy. Four proteins were measured from peripheral blood; Alkaline Phosphatase (AP), Aminotransferase (AT), Aspartate Aminotransferase (AspAT) and Gamma-glutamyl transpeptidase (GGT). The reference population is the set of patients in the study, and the reference data are the measured values for each of the protein concentrations plus the relative controls defined as all pair-wise ratios of abundance of each protein. In this example, consider a hypothetical new sample for a patient with unknown liver status with the following measurements AP=56, AT=49, AspAT=28 and GGT=6. An indicator value for liver disease may be generated from these measurements, but it is not yet known if the values are valid (if there has been some failure in measurement). All of these measurements are within the observed range of values for each of these proteins, so this sample would traditionally be considered as having satisfied the controls (being within the observed reference distribution. FIG. 13A shows the measured values for the new sample against the reference distribution for each measured biomarker (AP, AT, AspAT and GGT)). It can be seen that the sample falls within the reference range for each measured biomarker and therefore would traditionally be considered valid. Table 4 shows the values for each measured biomarker against the reference distribution and the probability of failure for each reference distribution.

TABLE 4

|  | AP | AT | AspAT | GGT |
|---|---|---|---|---|
| Sample Value | 56 | 49 | 28 | 6 |
| In range | Yes | Yes | Yes | Yes |
| P value | 0.451 | 0.340 | 0.739 | 0.411 |

Figure 13B:
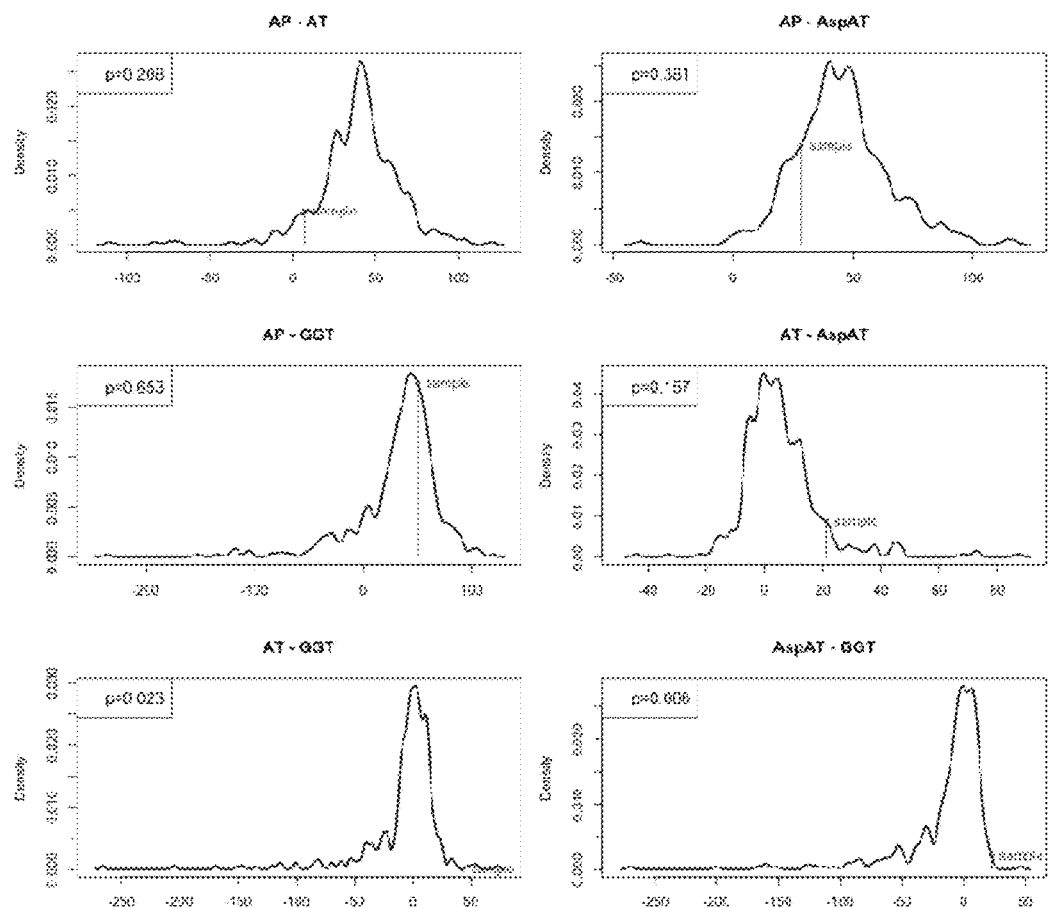
FIG. 13B is a plot showing the same invalid sample against a reference population of derived control biomarkers.

FIG. 13B shows the same sample against derived control distributions. In the case of AT-GGT and Asp-GGT, there are p values less than 0.05, indicating that this sample is unlikely to have come from the population of samples for which this test was designed, or there is some other failure, and therefore the indicator value (result) for this test is invalid.

Table 5 shows the relative control values for this sample and the specific controls capable of detecting this failure.

TABLE 5

|  | AP-AT | AP-AspAT | AP-GGT | AT-AspAT | AT-GGT | AspAT-GGT |
|---|---|---|---|---|---|---|
| Sample Value | 7 | 28 | 50 | 21 | 43 | 22 |
| In range | Yes | Yes | Yes | Yes | No | No |
| P value | 0.208 | 0.381 | 0.653 | 0.157 | 0.023 | 0.006 |

Accordingly, the above described system introduces the use of relative internal controls in the case of multi-biomarker medical devices, such that the need for controls that are not internal relative controls may be reduced or eliminated.

In one example, the relative internal controls are relative biomarkers internal to the sample that are used to ensure that the values used in establishing an indicator are valid. The relative biomarkers can be derived from measured biomarker values, with these being used by defining corresponding acceptable reference thresholds for each relative biomarker. These relative biomarkers may or may not include relative biomarkers used in determining the indicator, and could include the same biomarker values used in different or the same combinations. In one example, this provides a set of relevant controls without the need for any additional measured biomarkers being added to the assay.

The system can further be used to provide the appropriate use of these controls in a medical device using the relative biomarkers used in establishing the indicator value.

The system can also provide a method by which additional internal relative biomarkers may be added to the group of relative controls to meet any arbitrarily stringent control requirement such that a minimal set of additional measured biomarkers is required, thus providing an optimal performance for a minimum cost.

Despite allowing additional markers to be avoided, the system can successfully detect test failure in cases where prior art methods are not able to, a critical advance in the case of medical devices where acting on an invalid test results can have potentially life threatening consequences.

The system is also shown by example to appropriately pass a result in cases where prior art methods unnecessarily fail a sample. Also an important advance for medical devices with potentially life-critical consequences if a test is unnecessarily failed (and the result is therefore unavailable).

A further example will now be described using in-house data derived from the use of real-time polymerase chain reaction (RT-PCR) on 546 blood samples taken from patients with suspected sepsis. The results of the assay provide a probability of a patient having sepsis (or SIRS) based on a formula that uses the PCR Ct (cycle time) values for each of four target genes (PLA2G7, PLAC8, LAMP1 and CEACAM4).

The method in brief was as follows. Patient blood was collected directly into PAXgene tubes and total RNA extracted. The RT-PCR assay was provided in kit form to a hospital laboratory based in the Netherlands. The assay uses quantitative, real-time determination of the amount of each four host immune cell RNA transcripts in the sample based on the detection of fluorescence on a qRT-PCR instrument (e.g. Applied Biosystems 7500 Fast Dx Real-Time PCR Instrument, Applied Biosystems, Foster City, Calif., catalogue number 440685; K082562). Transcripts are each reverse-transcribed, amplified, detected, and quantified in a separate reaction well for each target gene using a probe that was visualized in the FAM channel. Each of the four target genes has a known Ct range and when assay results are obtained outside of these ranges the test is failed. For each sample the following internal controls were also run in separate reaction vessels—HIGH, LOW, NEGATIVE and a no-template (NTC). The HIGH, LOW and NEGATIVE internal controls contain a known quantity of an artificial DNA template—each of these separate reactions must also fall within a particular Ct range for the assay to pass, and the NTC must not amplify a PCR product.

A summary table of the results from running the assay on these 546 samples using both control methods ("Normal" and "Relative") is shown below in Table 6. Full results are shown in Tables 7, 8, 9 and 10.

TABLE 6

|  | Relative | |
|---|---|---|
| Normal | Fail | Pass |
| Fail (Controls) | 0 | 23 |
| Fail (Four Targets) | 2 | 3 |
| Pass | 13 | 505 |

A brief summary, explanation and discussion of these results follows.

505 samples (92.5%) were passed using both control methods.

Two (2) samples were failed using both control strategies. Using the Normal controls method both samples failed because the Ct values for the target gene PLA2G7 were out of the expected Ct range. Using the Relative controls method these same two samples were strongly failed because multiple Relative control p values were obtained that were less than 0.001.

26 samples were failed using Normal controls method but were passed using Relative control method. Of these 26 samples, 23 were failed because the LOW control was out of range. For these 23 samples, all individual gene target measurements (PLA2G7, PLAC8, LAMP1 and CEACAM4) were within the expected Ct range, and all Relative controls passed. Upon further inspection of the Ct values for individual genes and other Normal controls the 23 samples that were failed because of one out-of-range Normal control (LOW) should not have been. The Relative control strategy did not fail these samples. In practice this would mean that the use of the Relative controls strategy would have 'rescued' 23 valid diagnostic tests that would be denied to the patient using a Normal control method.

The other three (3) samples failed using the Normal method because the Ct values for PLA2G7 were out of the expected range for this gene. Of these three samples:

1) Sample IXP_128: reported adjusted p values for the Relative controls above 0.045. Such a p value suggests that this sample should not have been failed. Upon further inspection of the Ct values all individual gene measurements were comparatively high (in the high range for values expected for the other three genes but not out of range). Such a result suggests that the assay was run with a low input RNA concentration or low quality RNA. Despite this, a valid probability of sepsis was still able to be calculated. Further, the retrospective clinical diagnosis of the patient matched the sepsis probability from the assay, implying that the assay result was valid and should not have been failed.

2) Sample 6869: The Reported Relative control p values were as low as 0.0016. A result like this can be expected in 16 in every thousand normal tests.

3) Sample 1357: The Reported Relative control p values were as low as 0.002. A result like this can be expected in one in every five hundred normal tests.

The use of Relative control p values allows a clinical interpretation of the relevance of an abnormality level (p value), rather than an absolute call, allowing the treating physician (or a procedure on behalf of the physician) to determine the optimal p value at which to call a fail status on the test.

There were 13 instances where the Normal method passed samples whereas the Relative method did not. In these instances all measured gene markers were within the expected Ct range, and all Normal controls were also within range. However, these samples resulted in a low p value using the Relative method. In fact, the probability that the Relative controls measurements would happen by chance for any of these samples is less than one in one thousand. These Relative control results suggests a high level of abnormality for these 13 samples, and implies that these samples are not similar to other samples observed, nor similar to the patient population used for the development and interpretation of the diagnostic. Based on the high level of abnormality using the Relative control approach these 13 samples should be failed despite the measured markers and Normal controls falling within expected Ct range. In this instance the Relative control approach is especially useful, as it has identified patients for whom the interpretation of the diagnostic result using the Normal control approach is not valid. Further, the Relative control approach provides a confidence of the non-validity of the result. These latter two points are discussed in more detail below.

Considering sample 3787: all Ct values of the genes are within expected range, and the Normal internal controls all are within range. Thus, this result would be considered valid using the Normal control approach. However, the Relative control CEACAM4/LAMP1 has a p value of 0.0007642 and the Relative control LAMP1/PLAC8 has a p value of 3.96E-07 indicating that such a result occurs in less than one in a million cases (based on the distribution curve of expected results). Such a result can be interpreted in two ways:

1). The test values are correct, and this really is a one-in-a-million patient.

2). The test values are incorrect and there is some problem with the assay.

Any patient sample that generates a test result so radically different (1:1,000,000 chance) from all other patient samples should not be diagnosed with reference to other patient sample results that fit within the normal distribution—such a result should at least be further investigated (e.g. repeat the assay and/or investigate patient clinical notes).

Thus, when Relative controls approach reveal highly unlikely results (based on p value) the test should be failed. In these 13 cases, through appropriate failure of the samples, the Relative controls approach can 1) 'protect' patients from diagnostic calls that are unlikely to be actually valid, and 2) detect more sensitively test results that do not reflect the true status of the patient.

Full results of the 546 assays are shown in Tables 7, 8, 9 and 10.

Table 7 shows raw data results for 505 samples (of 546) that passed using both the Normal and Relative controls method.

TABLE 7

| | Normal Controls | | | | | | Relative Controls | | | | | | |
|---|---|---|---|---|---|---|---|---|---|---|---|---|---|
| Sample | CEA-CAM4 | LAMP1 | PLA-2G7 | PLAC8 | External Controls | Status | CEA-CAM4/ LAMP1 pVal | CEA-CAM4/ PLAC8 pVal | CEA-CAM4/ PLA2G7 pVal | LAMP1/ PLAC8 pVal | LAMP1/ PLA2G7 pVal | PLAC8/ PLA2G7 pVal | Status |
| 6607 | 21.3 | 23.7 | 25.0 | 21.6 | P | P | 0.368 | 0.233 | 0.472 | 0.535 | 0.222 | 0.185 | P |
| 6617 | 22.5 | 24.3 | 28.0 | 19.8 | P | P | 0.769 | 0.267 | 0.838 | 0.163 | 0.941 | 0.405 | P |
| 6629 | 21.6 | 24.0 | 27.3 | 21.1 | P | P | 0.363 | 0.581 | 0.762 | 0.945 | 0.897 | 0.948 | P |
| 6636 | 22.0 | 24.7 | 32.7 | 22.0 | P | P | 0.205 | 0.331 | 0.003 | 0.906 | 0.012 | 0.049 | P |
| 6648 | 23.7 | 23.6 | 29.2 | 22.3 | P | P | 0.072 | 0.916 | 0.810 | 0.233 | 0.248 | 0.787 | P |
| 6650 | 21.6 | 24.3 | 29.5 | 17.9 | P | P | 0.224 | 0.059 | 0.146 | 0.004 | 0.341 | 0.018 | P |
| 6653 | 21.2 | 24.0 | 26.8 | 18.3 | P | P | 0.183 | 0.193 | 0.809 | 0.019 | 0.685 | 0.328 | P |
| 6656 | 24.0 | 24.3 | 28.5 | 22.3 | P | P | 0.148 | 0.737 | 0.786 | 0.491 | 0.668 | 0.971 | P |
| 6657 | 22.4 | 23.2 | 26.9 | 21.2 | P | P | 0.414 | 0.963 | 0.753 | 0.521 | 0.944 | 0.765 | P |
| 6658 | 22.0 | 24.3 | 31.1 | 21.4 | P | P | 0.480 | 0.672 | 0.036 | 0.953 | 0.058 | 0.120 | P |
| IPX-098 | 21.5 | 23.8 | 30.5 | 19.3 | P | P | 0.433 | 0.422 | 0.041 | 0.155 | 0.072 | 0.025 | P |
| IXP-080 | 23.9 | 24.4 | 25.2 | 20.0 | P | P | 0.232 | 0.042 | 0.050 | 0.191 | 0.133 | 0.627 | P |
| IXP-081 | 23.6 | 24.3 | 27.2 | 22.0 | P | P | 0.368 | 0.778 | 0.451 | 0.725 | 0.719 | 0.628 | P |
| IXP-082 | 23.2 | 25.2 | 28.5 | 21.9 | P | P | 0.623 | 0.984 | 0.921 | 0.706 | 0.890 | 0.922 | P |
| IXP-083 | 24.0 | 24.7 | 29.5 | 22.1 | P | P | 0.317 | 0.592 | 0.820 | 0.879 | 0.458 | 0.608 | P |
| IXP-087 | 23.1 | 23.7 | 26.4 | 21.1 | P | P | 0.265 | 0.595 | 0.363 | 0.810 | 0.674 | 0.638 | P |
| IXP-088 | 22.5 | 24.7 | 25.5 | 21.6 | P | P | 0.489 | 0.816 | 0.263 | 0.800 | 0.122 | 0.270 | P |
| IXP-089 | 21.2 | 23.1 | 28.8 | 20.4 | P | P | 0.705 | 0.738 | 0.188 | 0.935 | 0.221 | 0.348 | P |
| IXP-090 | 21.1 | 23.7 | 29.0 | 21.2 | P | P | 0.256 | 0.319 | 0.142 | 0.810 | 0.313 | 0.498 | P |
| IXP-095 | 22.6 | 25.2 | 27.4 | 18.7 | P | P | 0.246 | 0.043 | 0.870 | 0.003 | 0.450 | 0.292 | P |
| IXP-096 | 22.9 | 24.5 | 27.3 | 22.0 | P | P | 0.954 | 0.779 | 0.708 | 0.797 | 0.666 | 0.624 | P |
| IXP-097 | 24.0 | 25.0 | 28.8 | 21.9 | P | P | 0.566 | 0.508 | 0.911 | 0.771 | 0.868 | 0.768 | P |
| 6681 | 25.2 | 26.0 | 30.3 | 23.1 | P | P | 0.380 | 0.530 | 0.977 | 0.972 | 0.640 | 0.692 | P |

TABLE 7-continued

| | Normal Controls | | | | | Relative Controls | | | | | | |
|---|---|---|---|---|---|---|---|---|---|---|---|---|
| Sample | CEA-CAM4 | LAMP1 | PLA-2G7 | PLAC8 | External Controls | Status | CEA-CAM4/ LAMP1 pVal | CEA-CAM4/ PLAC8 pVal | CEA-CAM4/ PLA2G7 pVal | LAMP1/ PLAC8 pVal | LAMP1/ PLA2G7 pVal | PLAC8/ PLA2G7 pVal | Status |
| 6694 | 21.4 | 24.3 | 27.3 | 21.7 | P | P | 0.159 | 0.248 | 0.669 | 0.831 | 0.808 | 0.754 | P |
| 6706 | 22.7 | 24.4 | 28.2 | 20.7 | P | P | 0.896 | 0.559 | 0.808 | 0.473 | 0.845 | 0.579 | P |
| 6709 | 21.5 | 24.5 | 26.9 | 21.3 | P | P | 0.102 | 0.423 | 0.860 | 0.743 | 0.532 | 0.748 | P |
| 6713 | 21.4 | 24.2 | 26.1 | 19.5 | P | P | 0.174 | 0.596 | 0.844 | 0.121 | 0.374 | 0.886 | P |
| 6718 | 23.2 | 24.3 | 29.7 | 19.6 | P | P | 0.612 | 0.069 | 0.452 | 0.116 | 0.289 | 0.085 | P |
| 6735 | 23.1 | 25.7 | 27.4 | 23.2 | P | P | 0.247 | 0.311 | 0.696 | 0.808 | 0.319 | 0.349 | P |
| 6744 | 20.5 | 23.7 | 31.1 | 19.1 | P | P | 0.066 | 0.923 | 0.004 | 0.151 | 0.027 | 0.010 | P |
| 6746 | 21.1 | 23.2 | 26.1 | 18.2 | P | P | 0.573 | 0.184 | 0.935 | 0.068 | 0.712 | 0.475 | P |
| 6750 | 22.3 | 23.6 | 26.1 | 21.0 | P | P | 0.759 | 0.923 | 0.492 | 0.906 | 0.559 | 0.592 | P |
| 6888 | 23.4 | 24.5 | 26.3 | 22.2 | P | P | 0.593 | 0.985 | 0.238 | 0.714 | 0.317 | 0.313 | P |
| IXP_099 | 23.0 | 24.6 | 25.5 | 21.2 | P | P | 0.997 | 0.639 | 0.175 | 0.619 | 0.146 | 0.372 | P |
| IXP_102 | 24.8 | 26.2 | 28.2 | 22.8 | P | P | 0.806 | 0.575 | 0.367 | 0.675 | 0.398 | 0.654 | P |
| IXP_104 | 24.4 | 25.7 | 28.9 | 22.5 | P | P | 0.783 | 0.646 | 0.763 | 0.772 | 0.852 | 0.992 | P |
| IXP_105 | 22.4 | 24.2 | 28.1 | 19.6 | P | P | 0.857 | 0.210 | 0.760 | 0.142 | 0.812 | 0.315 | P |
| IXP_107 | 22.5 | 23.6 | 25.2 | 21.3 | P | P | 0.532 | 0.996 | 0.214 | 0.648 | 0.307 | 0.282 | P |
| IXP_108 | 23.2 | 25.1 | 27.3 | 22.2 | P | P | 0.759 | 0.852 | 0.597 | 0.982 | 0.471 | 0.571 | P |
| IXP_110 | 22.1 | 23.9 | 29.4 | 19.5 | P | P | 0.829 | 0.291 | 0.261 | 0.200 | 0.272 | 0.111 | P |
| IXP_111 | 22.2 | 24.4 | 27.1 | 21.6 | P | P | 0.472 | 0.630 | 0.907 | 0.994 | 0.629 | 0.700 | P |
| IXP_112 | 24.2 | 25.2 | 27.2 | 22.9 | P | P | 0.486 | 0.949 | 0.271 | 0.663 | 0.405 | 0.362 | P |
| IXP_113 | 23.0 | 23.7 | 29.9 | 22.1 | P | P | 0.306 | 0.802 | 0.333 | 0.314 | 0.121 | 0.492 | P |
| IXP_117 | 22.0 | 22.7 | 28.3 | 19.6 | P | P | 0.327 | 0.371 | 0.540 | 0.807 | 0.252 | 0.290 | P |
| IXP_122 | 23.2 | 24.1 | 27.0 | 21.7 | P | P | 0.420 | 0.836 | 0.499 | 0.716 | 0.746 | 0.644 | P |
| 6762 | 25.1 | 24.9 | 29.0 | 20.4 | P | P | 0.050 | 0.008 | 0.531 | 0.164 | 0.761 | 0.310 | P |
| 6773 | 23.7 | 24.1 | 29.4 | 20.9 | P | P | 0.181 | 0.238 | 0.725 | 0.771 | 0.296 | 0.316 | P |
| 6776 | 22.7 | 24.3 | 28.8 | 20.1 | P | P | 0.998 | 0.298 | 0.587 | 0.266 | 0.561 | 0.278 | P |
| 6786 | 21.5 | 23.4 | 27.7 | 18.6 | P | P | 0.730 | 0.190 | 0.587 | 0.100 | 0.681 | 0.214 | P |
| 6796 | 25.1 | 25.4 | 29.9 | 20.5 | P | P | 0.169 | 0.011 | 0.889 | 0.085 | 0.592 | 0.166 | P |
| 6824 | 23.2 | 24.6 | 29.2 | 22.2 | P | P | 0.882 | 0.828 | 0.625 | 0.734 | 0.549 | 0.769 | P |
| 6825 | 22.2 | 24.4 | 27.8 | 23.4 | P | P | 0.517 | 0.065 | 0.779 | 0.135 | 0.982 | 0.397 | P |
| 6841 | 22.5 | 24.1 | 28.2 | 20.2 | P | P | 0.939 | 0.412 | 0.765 | 0.413 | 0.720 | 0.458 | P |
| 6844 | 22.2 | 23.7 | 29.1 | 20.4 | P | P | 0.973 | 0.690 | 0.329 | 0.688 | 0.287 | 0.281 | P |
| 6845 | 22.6 | 24.6 | 28.1 | 22.5 | P | P | 0.624 | 0.385 | 0.800 | 0.568 | 0.979 | 0.768 | P |
| 6867 | 21.0 | 23.2 | 24.5 | 20.2 | P | P | 0.474 | 0.731 | 0.411 | 0.880 | 0.215 | 0.361 | P |
| IXP_123 | 24.4 | 24.7 | 28.3 | 22.4 | P | P | 0.161 | 0.546 | 0.519 | 0.711 | 0.994 | 0.842 | P |
| IXP_124 | 22.4 | 25.1 | 29.1 | 19.3 | P | P | 0.200 | 0.174 | 0.398 | 0.017 | 0.789 | 0.125 | P |
| IXP_129 | 23.4 | 24.7 | 27.1 | 23.2 | P | P | 0.728 | 0.417 | 0.455 | 0.264 | 0.530 | 0.261 | P |
| IXP_130 | 23.0 | 23.8 | 26.0 | 21.1 | P | P | 0.404 | 0.607 | 0.278 | 0.956 | 0.454 | 0.527 | P |
| IXP_131 | 22.2 | 24.5 | 26.8 | 20.3 | P | P | 0.427 | 0.609 | 0.816 | 0.263 | 0.518 | 0.919 | P |
| IXP_132 | 22.9 | 24.7 | 25.4 | 20.4 | P | P | 0.841 | 0.351 | 0.182 | 0.255 | 0.125 | 0.547 | P |
| IXP_135 | 22.0 | 24.5 | 28.4 | 19.4 | P | P | 0.336 | 0.292 | 0.496 | 0.069 | 0.802 | 0.226 | P |
| IXP_137 | 23.4 | 24.7 | 30.1 | 22.1 | P | P | 0.808 | 0.964 | 0.398 | 0.898 | 0.303 | 0.449 | P |
| IXP_142 | 23.3 | 24.3 | 27.3 | 21.2 | P | P | 0.479 | 0.475 | 0.563 | 0.804 | 0.790 | 0.939 | P |
| IXP_145 | 22.9 | 25.0 | 28.2 | 22.5 | P | P | 0.561 | 0.530 | 0.892 | 0.803 | 0.885 | 0.799 | P |
| 6890 | 22.1 | 22.8 | 28.2 | 19.2 | P | P | 0.325 | 0.215 | 0.587 | 0.542 | 0.283 | 0.229 | P |
| 6650 | 22.3 | 22.7 | 29.8 | 18.6 | P | P | 0.175 | 0.060 | 0.209 | 0.306 | 0.043 | 0.028 | P |
| 6869 | 23.2 | 24.7 | 26.9 | 23.2 | P | P | 0.898 | 0.359 | 0.439 | 0.285 | 0.443 | 0.226 | P |
| IXP_128 | 25.6 | 26.7 | 30.8 | 24.1 | P | P | 0.560 | 0.869 | 0.935 | 0.805 | 0.705 | 0.867 | P |
| 6592 | 22.4 | 24.3 | 26.0 | 20.4 | P | P | 0.712 | 0.524 | 0.410 | 0.344 | 0.285 | 0.737 | P |
| 6598 | 21.3 | 22.6 | 26.0 | 20.5 | P | P | 0.739 | 0.698 | 0.872 | 0.512 | 0.995 | 0.713 | P |
| 6601 | 22.5 | 23.5 | 25.3 | 20.3 | P | P | 0.523 | 0.458 | 0.228 | 0.742 | 0.329 | 0.547 | P |
| 6603 | 22.1 | 23.3 | 29.0 | 22.2 | P | P | 0.651 | 0.328 | 0.360 | 0.170 | 0.227 | 0.832 | P |
| 6622 | 27.3 | 29.5 | 30.1 | 24.5 | P | P | 0.429 | 0.233 | 0.234 | 0.065 | 0.094 | 0.746 | P |
| 6624 | 23.0 | 24.0 | 27.5 | 21.1 | P | P | 0.492 | 0.611 | 0.736 | 0.964 | 0.985 | 0.992 | P |
| 6631 | 22.3 | 23.5 | 27.0 | 20.1 | P | P | 0.641 | 0.431 | 0.810 | 0.615 | 0.980 | 0.796 | P |
| 6641 | 21.9 | 23.0 | 26.2 | 19.7 | P | P | 0.559 | 0.466 | 0.678 | 0.723 | 0.878 | 0.942 | P |
| 6643 | 21.5 | 22.7 | 27.6 | 18.7 | P | P | 0.677 | 0.250 | 0.575 | 0.354 | 0.418 | 0.244 | P |
| 6647 | 20.4 | 24.1 | 30.9 | 23.2 | P | P | 0.016 | 0.002 | 0.004 | 0.129 | 0.064 | 0.516 | P |
| 6649 | 23.7 | 24.5 | 27.5 | 19.2 | P | P | 0.381 | 0.013 | 0.509 | 0.043 | 0.786 | 0.365 | P |
| 6665 | 24.1 | 23.6 | 29.3 | 20.6 | P | P | 0.017 | 0.082 | 0.990 | 0.905 | 0.227 | 0.299 | P |
| IXP-084 | 21.1 | 23.3 | 31.4 | 19.4 | P | P | 0.512 | 0.741 | 0.007 | 0.408 | 0.010 | 0.011 | P |
| IXP-085 | 22.0 | 25.3 | 25.1 | 20.0 | P | P | 0.066 | 0.555 | 0.292 | 0.050 | 0.041 | 0.575 | P |
| IXP-086 | 22.6 | 24.2 | 31.8 | 19.7 | P | P | 0.997 | 0.198 | 0.031 | 0.170 | 0.020 | 0.009 | P |
| IXP-091 | 23.8 | 25.0 | 26.9 | 22.5 | P | P | 0.692 | 0.945 | 0.291 | 0.832 | 0.350 | 0.384 | P |
| IXP-092 | 24.3 | 26.1 | 28.0 | 22.5 | P | P | 0.816 | 0.701 | 0.482 | 0.563 | 0.384 | 0.704 | P |
| IXP-093 | 22.5 | 24.2 | 28.1 | 20.0 | P | P | 0.966 | 0.324 | 0.794 | 0.278 | 0.795 | 0.418 | P |
| IXP-094 | 23.8 | 25.4 | 26.8 | 22.0 | P | P | 0.997 | 0.669 | 0.261 | 0.647 | 0.227 | 0.473 | P |
| IXP-100 | 24.0 | 25.9 | 25.6 | 22.1 | P | P | 0.730 | 0.594 | 0.064 | 0.413 | 0.031 | 0.200 | P |
| IXP-101 | 21.9 | 24.0 | 27.9 | 19.0 | P | P | 0.536 | 0.222 | 0.618 | 0.080 | 0.821 | 0.249 | P |
| IXP-103 | 22.7 | 24.9 | 29.5 | 20.1 | P | P | 0.473 | 0.318 | 0.378 | 0.113 | 0.557 | 0.177 | P |
| IXP-106 | 23.2 | 24.4 | 27.9 | 20.2 | P | P | 0.666 | 0.180 | 0.850 | 0.264 | 0.991 | 0.530 | P |
| IXP-114 | 23.9 | 25.6 | 27.1 | 21.8 | P | P | 0.918 | 0.477 | 0.307 | 0.405 | 0.251 | 0.644 | P |
| 6669 | 21.4 | 22.6 | 26.5 | 20.0 | P | P | 0.659 | 0.897 | 0.995 | 0.856 | 0.821 | 0.935 | P |
| 6678 | 22.1 | 23.2 | 26.4 | 20.4 | P | P | 0.584 | 0.717 | 0.680 | 0.991 | 0.866 | 0.887 | P |

TABLE 7-continued

|  | Normal Controls | | | | | | Relative Controls | | | | | | |
| --- | --- | --- | --- | --- | --- | --- | --- | --- | --- | --- | --- | --- | --- |
| Sample | CEA-CAM4 | LAMP1 | PLA-2G7 | PLAC8 | External Controls | Status | CEA-CAM4/ LAMP1 pVal | CEA-CAM4/ PLAC8 pVal | CEA-CAM4/ PLA2G7 pVal | LAMP 1/ PLAC8 pVal | LAMP 1/ PLA2G7 pVal | PLAC8/ PLA2G7 pVal | Status |
| 6679 | 23.1 | 23.4 | 27.8 | 20.7 | P | P | 0.141 | 0.366 | 0.860 | 0.919 | 0.586 | 0.703 | P |
| 6686 | 22.7 | 24.5 | 30.2 | 22.1 | P | P | 0.801 | 0.602 | 0.202 | 0.708 | 0.214 | 0.428 | P |
| 6689 | 21.9 | 24.1 | 29.9 | 22.0 | P | P | 0.497 | 0.297 | 0.124 | 0.535 | 0.190 | 0.477 | P |
| 6698 | 22.7 | 23.5 | 25.1 | 21.9 | P | P | 0.397 | 0.706 | 0.160 | 0.310 | 0.277 | 0.151 | P |
| 6715 | 20.2 | 22.6 | 27.7 | 19.2 | P | P | 0.362 | 0.830 | 0.203 | 0.666 | 0.362 | 0.331 | P |
| 6732 | 23.0 | 24.1 | 25.9 | 21.0 | P | P | 0.565 | 0.536 | 0.249 | 0.808 | 0.341 | 0.528 | P |
| 6748 | 22.0 | 23.9 | 25.5 | 21.9 | P | P | 0.739 | 0.386 | 0.406 | 0.494 | 0.290 | 0.218 | P |
| 6752 | 22.9 | 23.7 | 27.4 | 19.8 | P | P | 0.394 | 0.163 | 0.756 | 0.385 | 0.927 | 0.579 | P |
| 6758 | 21.6 | 22.4 | 27.1 | 18.3 | P | P | 0.407 | 0.125 | 0.830 | 0.301 | 0.520 | 0.275 | P |
| 6882 | 22.1 | 24.3 | 27.6 | 22.9 | P | P | 0.459 | 0.114 | 0.826 | 0.251 | 0.894 | 0.457 | P |
| IXP-115 | 22.4 | 24.1 | 26.4 | 20.5 | P | P | 0.883 | 0.607 | 0.574 | 0.512 | 0.498 | 0.856 | P |
| IXP-116 | 22.4 | 23.4 | 27.8 | 21.4 | P | P | 0.469 | 0.913 | 0.870 | 0.522 | 0.591 | 0.939 | P |
| IXP-118 | 21.2 | 24.4 | 27.6 | 22.9 | P | P | 0.064 | 0.026 | 0.481 | 0.299 | 0.867 | 0.477 | P |
| IXP-119 | 22.5 | 24.4 | 28.0 | 20.5 | P | P | 0.771 | 0.542 | 0.840 | 0.390 | 0.942 | 0.593 | P |
| IXP-120 | 22.5 | 24.0 | 28.0 | 21.8 | P | P | 0.936 | 0.680 | 0.840 | 0.618 | 0.797 | 0.945 | P |
| IXP-121 | 20.4 | 22.7 | 29.3 | 18.1 | P | P | 0.407 | 0.426 | 0.044 | 0.147 | 0.080 | 0.027 | P |
| IXP-125 | 22.7 | 25.1 | 28.8 | 22.7 | P | P | 0.382 | 0.341 | 0.595 | 0.703 | 0.893 | 0.918 | P |
| IXP-126 | 22.3 | 24.1 | 26.2 | 20.3 | P | P | 0.838 | 0.567 | 0.546 | 0.448 | 0.453 | 0.854 | P |
| IXP-127 | 23.0 | 24.4 | 26.2 | 21.2 | P | P | 0.869 | 0.674 | 0.322 | 0.742 | 0.326 | 0.544 | P |
| IXP-133 | 22.3 | 25.1 | 27.8 | 21.1 | P | P | 0.188 | 0.989 | 0.832 | 0.348 | 0.669 | 0.861 | P |
| IXP-134 | 23.2 | 25.9 | 25.4 | 19.0 | P | P | 0.209 | 0.028 | 0.138 | 0.001 | 0.027 | 0.983 | P |
| 3967 | 24.6 | 26.0 | 29.3 | 21.3 | P | P | 0.874 | 0.121 | 0.845 | 0.124 | 0.897 | 0.454 | P |
| 3746 | 20.7 | 23.1 | 24.9 | 20.9 | P | P | 0.375 | 0.265 | 0.653 | 0.585 | 0.355 | 0.295 | P |
| 3555 | 23.0 | 25.7 | 29.7 | 22.7 | P | P | 0.235 | 0.484 | 0.419 | 0.910 | 0.783 | 0.776 | P |
| 3469 | 20.1 | 23.0 | 26.8 | 19.8 | P | P | 0.134 | 0.487 | 0.399 | 0.731 | 0.874 | 0.750 | P |
| 3179 | 22.9 | 24.3 | 27.2 | 21.4 | P | P | 0.812 | 0.794 | 0.647 | 0.915 | 0.709 | 0.809 | P |
| 3363 | 21.0 | 23.4 | 25.3 | 19.5 | P | P | 0.346 | 0.839 | 0.685 | 0.369 | 0.365 | 0.818 | P |
| 2732 | 22.3 | 23.5 | 28.1 | 20.1 | P | P | 0.675 | 0.460 | 0.680 | 0.627 | 0.514 | 0.427 | P |
| 2603 | 22.3 | 23.9 | 26.1 | 21.6 | P | P | 0.952 | 0.652 | 0.519 | 0.661 | 0.470 | 0.410 | P |
| 2553 | 21.6 | 24.2 | 26.9 | 19.5 | P | P | 0.237 | 0.550 | 0.891 | 0.135 | 0.658 | 0.637 | P |
| 3974 | 23.1 | 25.4 | 30.5 | 22.5 | P | P | 0.408 | 0.592 | 0.230 | 0.978 | 0.381 | 0.472 | P |
| 3729_2 | 21.9 | 24.4 | 30.1 | 22.0 | P | P | 0.313 | 0.310 | 0.107 | 0.726 | 0.220 | 0.428 | P |
| 3499 | 24.6 | 24.9 | 27.8 | 22.2 | P | P | 0.140 | 0.382 | 0.314 | 0.892 | 0.729 | 0.724 | P |
| 3447 | 22.1 | 24.3 | 27.8 | 20.2 | P | P | 0.522 | 0.627 | 0.769 | 0.326 | 0.996 | 0.589 | P |
| 3248 | 22.3 | 24.3 | 27.6 | 19.7 | P | P | 0.623 | 0.322 | 0.905 | 0.158 | 0.907 | 0.491 | P |
| 3398 | 22.9 | 23.7 | 25.2 | 22.3 | P | P | 0.342 | 0.641 | 0.146 | 0.236 | 0.277 | 0.126 | P |
| 3008 | 22.5 | 24.2 | 26.5 | 21.1 | P | P | 0.935 | 0.874 | 0.552 | 0.820 | 0.497 | 0.674 | P |
| 2662 | 23.4 | 24.6 | 26.2 | 21.1 | P | P | 0.677 | 0.449 | 0.236 | 0.612 | 0.288 | 0.565 | P |
| 2568 | 22.3 | 24.4 | 29.3 | 20.3 | P | P | 0.548 | 0.564 | 0.298 | 0.293 | 0.414 | 0.215 | P |
| 3921 | 24.6 | 25.0 | 30.3 | 22.7 | P | P | 0.180 | 0.581 | 0.762 | 0.702 | 0.321 | 0.557 | P |
| 3729_1 | 21.1 | 22.7 | 27.1 | 19.0 | P | P | 0.959 | 0.485 | 0.638 | 0.434 | 0.632 | 0.413 | P |
| 3485 | 22.0 | 23.2 | 30.1 | 18.7 | P | P | 0.649 | 0.122 | 0.117 | 0.188 | 0.056 | 0.023 | P |
| 3445 | 22.4 | 23.9 | 30.6 | 18.6 | P | P | 0.965 | 0.049 | 0.104 | 0.039 | 0.077 | 0.010 | P |
| 3168 | 22.1 | 24.0 | 25.0 | 20.9 | P | P | 0.706 | 0.995 | 0.262 | 0.789 | 0.164 | 0.331 | P |
| 3367 | 23.8 | 26.0 | 29.0 | 21.0 | P | P | 0.447 | 0.243 | 0.946 | 0.073 | 0.759 | 0.454 | P |
| 3045 | 22.0 | 23.0 | 26.8 | 20.5 | P | P | 0.525 | 0.814 | 0.891 | 0.834 | 0.865 | 0.984 | P |
| 2776 | 23.0 | 24.5 | 28.0 | 21.8 | P | P | 0.918 | 0.979 | 0.993 | 0.919 | 0.967 | 0.982 | P |
| 2566 | 21.7 | 23.8 | 27.0 | 20.0 | P | P | 0.605 | 0.726 | 0.942 | 0.454 | 0.857 | 0.787 | P |
| 3934 | 20.6 | 22.8 | 27.7 | 17.8 | P | P | 0.507 | 0.238 | 0.277 | 0.082 | 0.404 | 0.102 | P |
| 3676_1 | 20.4 | 23.3 | 26.5 | 19.1 | P | P | 0.146 | 0.932 | 0.616 | 0.253 | 0.852 | 0.629 | P |
| 3485_1 | 22.3 | 24.7 | 29.4 | 21.8 | P | P | 0.387 | 0.610 | 0.312 | 0.934 | 0.513 | 0.567 | P |
| 3652 | 22.3 | 23.7 | 28.4 | 20.2 | P | P | 0.811 | 0.490 | 0.605 | 0.574 | 0.500 | 0.393 | P |
| 3201 | 21.6 | 23.5 | 24.5 | 19.6 | P | P | 0.666 | 0.563 | 0.250 | 0.353 | 0.147 | 0.515 | P |
| 3282 | 22.1 | 24.4 | 27.9 | 19.0 | P | P | 0.420 | 0.158 | 0.698 | 0.037 | 0.988 | 0.242 | P |
| 2990 | 23.0 | 24.8 | 25.9 | 21.2 | P | P | 0.862 | 0.650 | 0.245 | 0.542 | 0.182 | 0.462 | P |
| 2943 | 21.6 | 23.2 | 27.3 | 21.8 | P | P | 0.989 | 0.259 | 0.740 | 0.225 | 0.716 | 0.704 | P |
| 2541 | 22.0 | 23.4 | 31.0 | 19.9 | P | P | 0.858 | 0.545 | 0.039 | 0.605 | 0.021 | 0.032 | P |
| 3875 | 21.3 | 23.6 | 29.5 | 19.3 | P | P | 0.409 | 0.538 | 0.107 | 0.210 | 0.187 | 0.079 | P |
| 3677 | 21.3 | 23.9 | 26.2 | 20.3 | P | P | 0.245 | 0.852 | 0.926 | 0.520 | 0.497 | 0.849 | P |
| 3449 | 21.2 | 24.2 | 25.1 | 20.7 | P | P | 0.117 | 0.582 | 0.515 | 0.585 | 0.139 | 0.375 | P |
| 3136 | 22.6 | 23.1 | 24.9 | 20.2 | P | P | 0.262 | 0.398 | 0.149 | 0.929 | 0.322 | 0.455 | P |
| 3311 | 23.3 | 25.7 | 25.8 | 20.5 | P | P | 0.350 | 0.234 | 0.169 | 0.052 | 0.052 | 0.627 | P |
| 3333 | 23.1 | 23.8 | 27.1 | 20.8 | P | P | 0.317 | 0.408 | 0.538 | 0.876 | 0.872 | 0.965 | P |
| 3108 | 22.6 | 24.2 | 24.1 | 20.9 | P | P | 0.988 | 0.736 | 0.066 | 0.711 | 0.048 | 0.165 | P |
| 2855 | 21.4 | 23.3 | 25.1 | 20.8 | P | P | 0.735 | 0.639 | 0.448 | 0.798 | 0.325 | 0.351 | P |
| 2539 | 21.6 | 22.9 | 29.3 | 19.4 | P | P | 0.766 | 0.480 | 0.174 | 0.590 | 0.108 | 0.111 | P |
| 3900 | 22.0 | 25.1 | 26.1 | 19.8 | P | P | 0.092 | 0.461 | 0.605 | 0.045 | 0.163 | 0.991 | P |
| 3701 | 21.2 | 24.0 | 30.0 | 19.4 | P | P | 0.167 | 0.685 | 0.051 | 0.152 | 0.160 | 0.054 | P |
| 3803 | 22.3 | 24.5 | 28.6 | 20.5 | P | P | 0.486 | 0.670 | 0.505 | 0.337 | 0.713 | 0.408 | P |
| 3612 | 21.4 | 22.6 | 26.8 | 17.7 | P | P | 0.692 | 0.070 | 0.851 | 0.099 | 0.689 | 0.217 | P |
| 3233 | 24.0 | 25.1 | 30.1 | 21.4 | P | P | 0.543 | 0.274 | 0.624 | 0.468 | 0.406 | 0.284 | P |
| 3304 | 22.0 | 23.3 | 25.9 | 20.1 | P | P | 0.773 | 0.637 | 0.536 | 0.768 | 0.602 | 0.798 | P |
| 3059 | 22.2 | 24.5 | 28.6 | 22.8 | P | P | 0.422 | 0.165 | 0.496 | 0.369 | 0.741 | 0.816 | P |

TABLE 7-continued

| | Normal Controls | | | | | | Relative Controls | | | | | | |
|---|---|---|---|---|---|---|---|---|---|---|---|---|---|
| Sample | CEA-CAM4 | LAMP1 | PLA-2G7 | PLAC8 | External Controls | Status | CEA-CAM4/ LAMP1 pVal | CEA-CAM4/ PLAC8 pVal | CEA-CAM4/ PLA2G7 pVal | LAMP 1/ PLAC8 pVal | LAMP 1/ PLA2G7 pVal | PLAC8/ PLA2G7 pVal | Status |
| 3863 | 22.2 | 24.4 | 27.0 | 20.7 | P | P | 0.503 | 0.841 | 0.880 | 0.484 | 0.620 | 0.990 | P |
| 3676 | 22.2 | 23.9 | 27.4 | 19.4 | P | P | 0.957 | 0.238 | 0.968 | 0.194 | 0.987 | 0.464 | P |
| 3796 | 21.4 | 22.3 | 26.1 | 20.7 | P | P | 0.455 | 0.680 | 0.824 | 0.327 | 0.894 | 0.663 | P |
| 3583 | 21.9 | 22.6 | 26.8 | 19.3 | P | P | 0.312 | 0.288 | 0.933 | 0.689 | 0.678 | 0.578 | P |
| 3428 | 21.7 | 23.3 | 24.8 | 21.2 | P | P | 0.997 | 0.599 | 0.289 | 0.574 | 0.256 | 0.220 | P |
| 3317 | 23.2 | 26.1 | 29.8 | 19.5 | P | P | 0.159 | 0.063 | 0.437 | 0.003 | 0.894 | 0.076 | P |
| 3323 | 23.0 | 24.1 | 28.7 | 22.0 | P | P | 0.537 | 0.854 | 0.758 | 0.521 | 0.523 | 0.875 | P |
| 2960 | 20.3 | 22.2 | 26.4 | 17.1 | P | P | 0.727 | 0.145 | 0.574 | 0.071 | 0.668 | 0.178 | P |
| 3074 | 22.2 | 22.4 | 27.4 | 19.5 | P | P | 0.108 | 0.247 | 0.972 | 0.942 | 0.402 | 0.475 | P |
| 3848 | 21.6 | 23.5 | 27.8 | 18.3 | P | P | 0.746 | 0.110 | 0.561 | 0.052 | 0.643 | 0.148 | P |
| 3644 | 22.8 | 23.2 | 27.8 | 21.3 | P | P | 0.191 | 0.843 | 0.950 | 0.462 | 0.559 | 0.950 | P |
| 3729 | 21.6 | 24.3 | 26.7 | 22.6 | P | P | 0.226 | 0.089 | 0.984 | 0.348 | 0.532 | 0.306 | P |
| 3577 | 22.3 | 23.7 | 27.9 | 18.3 | P | P | 0.789 | 0.037 | 0.790 | 0.042 | 0.675 | 0.143 | P |
| 3390_1 | 20.9 | 23.5 | 27.5 | 18.0 | P | P | 0.299 | 0.183 | 0.435 | 0.030 | 0.749 | 0.144 | P |
| 3381 | 22.6 | 22.5 | 27.8 | 20.4 | P | P | 0.054 | 0.467 | 0.945 | 0.537 | 0.301 | 0.624 | P |
| 3330 | 20.4 | 23.1 | 26.0 | 20.2 | P | P | 0.238 | 0.445 | 0.786 | 0.969 | 0.766 | 0.828 | P |
| 2903 | 21.7 | 23.3 | 25.3 | 20.8 | P | P | 0.994 | 0.827 | 0.410 | 0.820 | 0.374 | 0.400 | P |
| 2582 | 22.2 | 23.8 | 28.3 | 21.1 | P | P | 0.903 | 0.889 | 0.590 | 0.952 | 0.605 | 0.702 | P |
| 3842 | 22.2 | 25.4 | 26.1 | 22.9 | P | P | 0.084 | 0.136 | 0.529 | 0.736 | 0.124 | 0.155 | P |
| 4001 | 21.0 | 23.9 | 30.7 | 17.3 | P | P | 0.158 | 0.051 | 0.017 | 0.002 | 0.062 | 0.001 | P |
| 3720 | 20.2 | 21.7 | 26.1 | 19.3 | P | P | 0.969 | 0.773 | 0.650 | 0.737 | 0.612 | 0.825 | P |
| 3575 | 20.7 | 23.0 | 28.4 | 21.1 | P | P | 0.429 | 0.208 | 0.179 | 0.441 | 0.294 | 0.677 | P |
| 3438 | 23.0 | 24.0 | 25.8 | 20.5 | P | P | 0.485 | 0.330 | 0.214 | 0.594 | 0.324 | 0.618 | P |
| 3320 | 22.9 | 24.4 | 27.7 | 21.3 | P | P | 0.929 | 0.793 | 0.849 | 0.830 | 0.873 | 0.992 | P |
| 3390 | 20.8 | 23.8 | 29.1 | 17.2 | P | P | 0.105 | 0.069 | 0.089 | 0.002 | 0.308 | 0.011 | P |
| 2832 | 23.1 | 23.8 | 27.2 | 21.3 | P | P | 0.350 | 0.700 | 0.617 | 0.791 | 0.944 | 0.839 | P |
| 2656_1 | 22.4 | 23.6 | 30.7 | 20.9 | P | P | 0.654 | 0.854 | 0.097 | 0.898 | 0.045 | 0.123 | P |
| 2462055 | 21.8 | 23.4 | 27.7 | 20.0 | P | P | 0.948 | 0.636 | 0.706 | 0.647 | 0.662 | 0.545 | P |
| 2724618 | 22.5 | 24.8 | 27.1 | 21.2 | P | P | 0.435 | 0.975 | 0.810 | 0.549 | 0.517 | 0.850 | P |
| 2114572 | 21.2 | 22.9 | 24.9 | 20.9 | P | P | 0.968 | 0.478 | 0.447 | 0.467 | 0.403 | 0.282 | P |
| 673 | 20.8 | 22.6 | 26.1 | 21.3 | P | P | 0.828 | 0.177 | 0.920 | 0.199 | 0.999 | 0.477 | P |
| 2040977 | 21.0 | 22.6 | 24.9 | 21.2 | P | P | 0.995 | 0.272 | 0.532 | 0.240 | 0.504 | 0.234 | P |
| 2110722 | 21.9 | 23.5 | 27.1 | 22.6 | P | P | 0.983 | 0.134 | 0.962 | 0.106 | 0.951 | 0.398 | P |
| 2699937 | 21.7 | 24.1 | 26.7 | 21.7 | P | P | 0.362 | 0.360 | 0.968 | 0.753 | 0.619 | 0.565 | P |
| 2965737 | 20.0 | 24.3 | 26.5 | 20.1 | P | P | 0.002 | 0.301 | 0.459 | 0.247 | 0.446 | 0.977 | P |
| 2765556 | 21.9 | 24.5 | 26.3 | 19.6 | P | P | 0.243 | 0.437 | 0.729 | 0.094 | 0.340 | 0.873 | P |
| 2690379 | 23.0 | 24.6 | 27.4 | 22.0 | P | P | 0.956 | 0.865 | 0.714 | 0.825 | 0.715 | 0.677 | P |
| 2568313 | 23.9 | 24.0 | 27.1 | 20.6 | P | P | 0.103 | 0.119 | 0.343 | 0.630 | 0.837 | 0.919 | P |
| 2746904 | 22.7 | 24.1 | 26.4 | 21.7 | P | P | 0.830 | 0.870 | 0.447 | 0.741 | 0.478 | 0.451 | P |
| 2983402 | 23.3 | 24.3 | 28.1 | 22.7 | P | P | 0.545 | 0.618 | 0.896 | 0.332 | 0.871 | 0.683 | P |
| 2661258 | 22.2 | 23.6 | 26.1 | 21.1 | P | P | 0.800 | 0.927 | 0.551 | 0.779 | 0.607 | 0.569 | P |
| 2392555 | 23.2 | 25.3 | 30.4 | 22.2 | P | P | 0.524 | 0.853 | 0.254 | 0.792 | 0.364 | 0.381 | P |
| 676 | 21.3 | 22.8 | 25.4 | 19.9 | P | P | 0.908 | 0.920 | 0.607 | 0.981 | 0.621 | 0.700 | P |
| 870 | 22.7 | 23.1 | 24.6 | 19.9 | P | P | 0.198 | 0.253 | 0.094 | 0.773 | 0.248 | 0.441 | P |
| 2235988 | 22.7 | 24.7 | 30.0 | 20.0 | P | P | 0.629 | 0.252 | 0.254 | 0.116 | 0.325 | 0.097 | P |
| 2256503 | 24.3 | 25.8 | 30.4 | 21.9 | P | P | 0.944 | 0.359 | 0.609 | 0.353 | 0.560 | 0.325 | P |
| 2258733 | 21.6 | 24.2 | 27.6 | 21.4 | P | P | 0.280 | 0.417 | 0.643 | 0.933 | 0.968 | 0.937 | P |
| 2488145 | 23.9 | 26.5 | 29.0 | 20.7 | P | P | 0.280 | 0.135 | 0.983 | 0.018 | 0.575 | 0.387 | P |
| 2140058 | 19.9 | 23.4 | 27.7 | 21.5 | P | P | 0.034 | 0.031 | 0.153 | 0.442 | 0.635 | 0.965 | P |
| 2668849 | 21.7 | 23.4 | 28.3 | 20.2 | P | P | 0.929 | 0.819 | 0.453 | 0.758 | 0.446 | 0.433 | P |
| 2752236 | 23.8 | 26.4 | 29.3 | 23.1 | P | P | 0.254 | 0.726 | 0.860 | 0.651 | 0.705 | 0.957 | P |
| 2405147 | 23.5 | 26.8 | 32.0 | 23.0 | P | P | 0.051 | 0.554 | 0.070 | 0.435 | 0.332 | 0.225 | P |
| 2267987 | 23.2 | 24.6 | 30.1 | 21.2 | P | P | 0.765 | 0.525 | 0.365 | 0.645 | 0.262 | 0.247 | P |
| 2303930 | 23.1 | 25.6 | 25.6 | 22.5 | P | P | 0.305 | 0.642 | 0.178 | 0.805 | 0.050 | 0.150 | P |
| 2268023 | 24.0 | 25.8 | 29.9 | 23.3 | P | P | 0.783 | 0.698 | 0.690 | 0.831 | 0.772 | 0.909 | P |
| 2235292 | 22.1 | 23.4 | 27.6 | 18.4 | P | P | 0.755 | 0.065 | 0.825 | 0.081 | 0.694 | 0.199 | P |
| 2260065 | 26.5 | 27.0 | 31.8 | 23.6 | P | P | 0.226 | 0.215 | 0.895 | 0.655 | 0.456 | 0.397 | P |
| 2557316 | 22.0 | 24.4 | 28.1 | 19.8 | P | P | 0.329 | 0.493 | 0.589 | 0.150 | 0.927 | 0.383 | P |
| 2564997 | 23.4 | 25.6 | 29.5 | 21.3 | P | P | 0.461 | 0.494 | 0.591 | 0.207 | 0.835 | 0.386 | P |
| 2197899 | 23.1 | 24.2 | 28.5 | 21.1 | P | P | 0.554 | 0.549 | 0.867 | 0.833 | 0.635 | 0.618 | P |
| 2202851 | 23.2 | 24.3 | 25.6 | 21.3 | P | P | 0.567 | 0.591 | 0.161 | 0.874 | 0.223 | 0.372 | P |
| 2370415 | 23.6 | 27.2 | 29.4 | 24.2 | P | P | 0.024 | 0.161 | 0.723 | 0.889 | 0.456 | 0.601 | P |
| 2387538 | 23.2 | 26.7 | 28.3 | 21.8 | P | P | 0.034 | 0.875 | 0.988 | 0.089 | 0.298 | 0.916 | P |
| 2520432 | 23.0 | 23.5 | 26.3 | 21.9 | P | P | 0.201 | 0.948 | 0.356 | 0.319 | 0.724 | 0.403 | P |
| 2469194 | 22.8 | 24.4 | 28.2 | 21.9 | P | P | 0.982 | 0.819 | 0.867 | 0.820 | 0.866 | 0.993 | P |
| 2493616 | 22.6 | 25.6 | 28.3 | 19.5 | P | P | 0.108 | 0.146 | 0.752 | 0.007 | 0.644 | 0.258 | P |
| 2511358 | 21.9 | 22.4 | 26.1 | 18.0 | P | P | 0.216 | 0.041 | 0.640 | 0.200 | 0.908 | 0.422 | P |
| 620 | 22.8 | 24.2 | 26.5 | 21.2 | P | P | 0.884 | 0.794 | 0.487 | 0.863 | 0.500 | 0.655 | P |
| 583 | 22.1 | 23.7 | 29.0 | 21.5 | P | P | 0.971 | 0.614 | 0.354 | 0.572 | 0.311 | 0.616 | P |
| 512 | 21.9 | 23.6 | 29.6 | 21.3 | P | P | 0.855 | 0.615 | 0.172 | 0.686 | 0.169 | 0.377 | P |
| 517 | 23.2 | 25.0 | 29.7 | 21.1 | P | P | 0.832 | 0.497 | 0.460 | 0.380 | 0.492 | 0.299 | P |
| 514 | 21.9 | 24.0 | 25.9 | 21.4 | P | P | 0.552 | 0.580 | 0.555 | 0.874 | 0.353 | 0.403 | P |
| 5678_1 | 20.9 | 22.9 | 27.1 | 16.9 | P | P | 0.720 | 0.033 | 0.581 | 0.011 | 0.679 | 0.083 | P |

TABLE 7-continued

|  | Normal Controls | | | | | | Relative Controls | | | | | | |
| --- | --- | --- | --- | --- | --- | --- | --- | --- | --- | --- | --- | --- | --- |
| Sample | CEA-CAM4 | LAMP1 | PLA-2G7 | PLAC8 | External Controls | Status | CEA-CAM4/ LAMP1 pVal | CEA-CAM4/ PLAC8 pVal | CEA-CAM4/ PLA2G7 pVal | LAMP 1/ PLAC8 pVal | LAMP 1/ PLA2G7 pVal | PLAC8/ PLA2G7 pVal | Status |
| 391 | 20.8 | 22.3 | 25.9 | 19.5 | P | P | 0.935 | 0.977 | 0.995 | 0.978 | 0.962 | 0.982 | P |
| 333 | 23.0 | 23.7 | 31.3 | 19.2 | P | P | 0.349 | 0.058 | 0.093 | 0.179 | 0.023 | 0.010 | P |
| 360 | 23.1 | 25.6 | 26.5 | 21.4 | P | P | 0.330 | 0.720 | 0.377 | 0.277 | 0.151 | 0.581 | P |
| 330 | 21.3 | 23.6 | 25.3 | 21.6 | P | P | 0.445 | 0.243 | 0.558 | 0.489 | 0.312 | 0.231 | P |
| 302 | 21.6 | 22.2 | 23.3 | 19.0 | P | P | 0.300 | 0.320 | 0.082 | 0.756 | 0.177 | 0.360 | P |
| 2475364 | 23.0 | 24.8 | 25.5 | 21.5 | P | P | 0.859 | 0.819 | 0.167 | 0.709 | 0.116 | 0.290 | P |
| 249291 | 22.4 | 24.2 | 27.0 | 22.5 | P | P | 0.809 | 0.330 | 0.797 | 0.387 | 0.691 | 0.424 | P |
| 4186 | 20.9 | 23.2 | 26.4 | 20.3 | P | P | 0.423 | 0.639 | 0.804 | 0.937 | 0.894 | 0.950 | P |
| 4109 | 23.3 | 25.3 | 30.8 | 19.1 | P | P | 0.685 | 0.023 | 0.215 | 0.007 | 0.259 | 0.016 | P |
| 4087 | 21.7 | 23.7 | 27.4 | 19.1 | P | P | 0.680 | 0.279 | 0.785 | 0.146 | 0.931 | 0.381 | P |
| 458 | 21.2 | 22.5 | 28.1 | 17.3 | P | P | 0.744 | 0.041 | 0.337 | 0.052 | 0.232 | 0.042 | P |
| 454_1 | 21.4 | 23.2 | 26.1 | 19.6 | P | P | 0.860 | 0.638 | 0.809 | 0.530 | 0.728 | 0.945 | P |
| 487 | 21.5 | 23.2 | 26.0 | 21.0 | P | P | 0.950 | 0.577 | 0.733 | 0.583 | 0.691 | 0.532 | P |
| 454 | 21.3 | 23.0 | 25.1 | 20.2 | P | P | 0.937 | 0.928 | 0.497 | 0.969 | 0.442 | 0.522 | P |
| 450 | 24.6 | 25.2 | 28.1 | 22.2 | P | P | 0.242 | 0.371 | 0.401 | 0.915 | 0.750 | 0.844 | P |
| 5769_1 | 23.1 | 25.9 | 30.3 | 21.2 | P | P | 0.157 | 0.620 | 0.261 | 0.120 | 0.617 | 0.206 | P |
| 286 | 22.6 | 23.5 | 27.2 | 21.4 | P | P | 0.447 | 0.989 | 0.800 | 0.571 | 0.914 | 0.820 | P |
| 204 | 20.3 | 22.7 | 25.7 | 21.1 | P | P | 0.387 | 0.134 | 0.875 | 0.331 | 0.792 | 0.453 | P |
| 194 | 22.0 | 23.2 | 26.5 | 20.9 | P | P | 0.640 | 0.925 | 0.756 | 0.661 | 0.920 | 0.746 | P |
| 4348 | 21.1 | 23.1 | 27.4 | 21.3 | P | P | 0.672 | 0.289 | 0.533 | 0.410 | 0.647 | 0.930 | P |
| 4229 | 21.7 | 24.2 | 27.4 | 21.5 | P | P | 0.291 | 0.414 | 0.746 | 0.915 | 0.858 | 0.839 | P |
| 4273 | 22.9 | 24.3 | 27.2 | 21.6 | P | P | 0.811 | 0.951 | 0.683 | 0.914 | 0.750 | 0.752 | P |
| 4206 | 24.2 | 25.6 | 31.2 | 20.1 | P | P | 0.839 | 0.025 | 0.320 | 0.025 | 0.242 | 0.029 | P |
| 4224 | 20.5 | 23.8 | 31.7 | 21.7 | P | P | 0.054 | 0.064 | 0.001 | 0.563 | 0.013 | 0.095 | P |
| 1654 | 23.0 | 26.8 | 27.4 | 22.2 | P | P | 0.012 | 0.725 | 0.696 | 0.152 | 0.096 | 0.586 | P |
| 3215498 | 22.6 | 24.1 | 26.3 | 21.9 | P | P | 0.917 | 0.706 | 0.444 | 0.633 | 0.442 | 0.377 | P |
| 2875063 | 21.9 | 23.8 | 25.1 | 20.2 | P | P | 0.706 | 0.750 | 0.322 | 0.540 | 0.211 | 0.504 | P |
| 2916462 | 23.2 | 25.2 | 30.3 | 23.3 | P | P | 0.621 | 0.328 | 0.286 | 0.493 | 0.368 | 0.731 | P |
| 2989696 | 24.9 | 26.2 | 28.1 | 22.4 | P | P | 0.725 | 0.345 | 0.338 | 0.452 | 0.393 | 0.787 | P |
| 3150468 | 22.0 | 22.3 | 25.7 | 18.5 | P | P | 0.155 | 0.084 | 0.458 | 0.415 | 0.932 | 0.702 | P |
| 3269616 | 22.5 | 23.6 | 28.5 | 21.0 | P | P | 0.661 | 0.840 | 0.613 | 0.919 | 0.446 | 0.578 | P |
| 2823098 | 21.2 | 24.3 | 31.1 | 21.8 | P | P | 0.077 | 0.143 | 0.011 | 0.780 | 0.063 | 0.180 | P |
| 3253112 | 22.6 | 24.2 | 28.0 | 20.5 | P | P | 0.994 | 0.481 | 0.869 | 0.449 | 0.862 | 0.576 | P |
| 3182559 | 20.5 | 22.1 | 24.3 | 19.9 | P | P | 0.982 | 0.618 | 0.492 | 0.606 | 0.454 | 0.374 | P |
| 2892503 | 24.0 | 25.2 | 28.9 | 22.9 | P | P | 0.712 | 0.912 | 0.931 | 0.701 | 0.927 | 0.889 | P |
| 2954473 | 22.0 | 24.0 | 26.5 | 21.0 | P | P | 0.644 | 0.831 | 0.774 | 0.914 | 0.590 | 0.709 | P |
| 3075030 | 21.9 | 23.2 | 25.1 | 20.7 | P | P | 0.695 | 0.981 | 0.301 | 0.757 | 0.360 | 0.364 | P |
| 3151800 | 24.2 | 25.3 | 30.3 | 21.9 | P | P | 0.589 | 0.400 | 0.608 | 0.613 | 0.412 | 0.347 | P |
| 2842448 | 24.6 | 25.0 | 30.7 | 21.3 | P | P | 0.205 | 0.114 | 0.584 | 0.442 | 0.223 | 0.159 | P |
| 2152744 | 21.4 | 23.5 | 29.1 | 22.9 | P | P | 0.564 | 0.033 | 0.166 | 0.063 | 0.230 | 0.948 | P |
| 3285480 | 24.1 | 24.7 | 27.7 | 23.1 | P | P | 0.285 | 0.854 | 0.447 | 0.332 | 0.777 | 0.444 | P |
| 3187134 | 21.8 | 21.3 | 24.7 | 19.3 | P | P | 0.018 | 0.332 | 0.238 | 0.497 | 0.932 | 0.656 | P |
| 2996445 | 22.0 | 24.2 | 28.2 | 20.5 | P | P | 0.533 | 0.844 | 0.585 | 0.508 | 0.783 | 0.557 | P |
| 2973087 | 21.8 | 23.3 | 25.3 | 19.5 | P | P | 0.950 | 0.455 | 0.430 | 0.452 | 0.414 | 0.810 | P |
| 3007078 | 23.2 | 24.7 | 29.3 | 19.1 | P | P | 0.892 | 0.028 | 0.610 | 0.024 | 0.538 | 0.081 | P |
| 3143971 | 21.7 | 24.0 | 27.2 | 19.5 | P | P | 0.441 | 0.456 | 0.831 | 0.177 | 0.877 | 0.532 | P |
| 3241087 | 21.8 | 22.2 | 25.0 | 20.0 | P | P | 0.161 | 0.658 | 0.328 | 0.587 | 0.727 | 0.560 | P |
| 2801327 | 24.5 | 25.3 | 26.7 | 22.3 | P | P | 0.380 | 0.453 | 0.121 | 0.869 | 0.220 | 0.370 | P |
| 2774672 | 22.9 | 24.4 | 26.8 | 19.8 | P | P | 0.902 | 0.146 | 0.541 | 0.144 | 0.552 | 0.740 | P |
| 3267724 | 24.1 | 24.1 | 26.8 | 20.1 | P | P | 0.070 | 0.032 | 0.214 | 0.329 | 0.667 | 0.846 | P |
| 3219499 | 24.8 | 25.5 | 26.9 | 20.5 | P | P | 0.367 | 0.021 | 0.128 | 0.070 | 0.237 | 0.958 | P |
| 3022381 | 21.8 | 21.9 | 25.0 | 19.4 | P | P | 0.105 | 0.399 | 0.325 | 0.786 | 0.803 | 0.725 | P |
| 2973476 | 24.2 | 25.3 | 30.1 | 22.0 | P | P | 0.600 | 0.501 | 0.637 | 0.736 | 0.443 | 0.421 | P |
| 3143818 | 22.3 | 24.0 | 26.6 | 21.2 | P | P | 0.874 | 0.930 | 0.691 | 0.983 | 0.613 | 0.692 | P |
| 3118227 | 24.2 | 24.6 | 29.2 | 23.8 | P | P | 0.179 | 0.516 | 0.967 | 0.096 | 0.532 | 0.674 | P |
| 3250409 | 22.5 | 24.2 | 27.5 | 20.5 | P | P | 0.878 | 0.583 | 0.954 | 0.486 | 0.890 | 0.783 | P |
| 2654918 | 24.0 | 25.2 | 26.7 | 21.5 | P | P | 0.664 | 0.370 | 0.229 | 0.522 | 0.282 | 0.610 | P |
| 2163170 | 22.3 | 23.5 | 28.1 | 20.1 | P | P | 0.695 | 0.489 | 0.678 | 0.650 | 0.522 | 0.443 | P |
| 3257803 | 23.4 | 24.7 | 28.6 | 21.8 | P | P | 0.733 | 0.761 | 0.989 | 0.939 | 0.853 | 0.848 | P |
| 2911717 | 23.9 | 25.0 | 29.3 | 22.9 | P | P | 0.563 | 0.875 | 0.873 | 0.558 | 0.645 | 0.964 | P |
| 3082897 | 24.7 | 25.3 | 30.7 | 20.3 | P | P | 0.261 | 0.014 | 0.622 | 0.071 | 0.276 | 0.060 | P |
| 2893476 | 24.0 | 26.9 | 30.0 | 24.1 | P | P | 0.167 | 0.306 | 0.668 | 0.928 | 0.818 | 0.814 | P |
| 3136847 | 22.1 | 23.2 | 26.1 | 21.7 | P | P | 0.557 | 0.503 | 0.557 | 0.254 | 0.735 | 0.366 | P |
| 3161091 | 20.4 | 22.2 | 24.9 | 19.6 | P | P | 0.761 | 0.740 | 0.762 | 0.893 | 0.634 | 0.647 | P |
| 3263354 | 23.2 | 24.0 | 26.9 | 20.1 | P | P | 0.354 | 0.163 | 0.474 | 0.413 | 0.760 | 0.836 | P |
| 2156886 | 23.7 | 25.2 | 29.6 | 22.5 | P | P | 0.999 | 0.958 | 0.655 | 0.956 | 0.632 | 0.723 | P |
| 3247954 | 20.6 | 24.1 | 26.8 | 20.8 | P | P | 0.031 | 0.281 | 0.578 | 0.681 | 0.633 | 0.876 | P |
| 3042060 | 24.6 | 26.9 | 27.6 | 22.8 | P | P | 0.373 | 0.670 | 0.289 | 0.272 | 0.114 | 0.507 | P |
| 2961182 | 25.1 | 26.5 | 32.4 | 23.7 | P | P | 0.859 | 0.896 | 0.258 | 0.992 | 0.192 | 0.292 | P |
| 3141749 | 21.0 | 23.0 | 24.0 | 20.0 | P | P | 0.610 | 0.844 | 0.287 | 0.873 | 0.162 | 0.300 | P |
| 3174398 | 22.5 | 23.4 | 27.2 | 22.2 | P | P | 0.466 | 0.492 | 0.842 | 0.207 | 0.881 | 0.563 | P |
| 2425352 | 21.3 | 23.2 | 24.4 | 20.0 | P | P | 0.713 | 0.969 | 0.287 | 0.758 | 0.185 | 0.370 | P |
| 2628334 | 21.1 | 25.0 | 27.1 | 22.4 | P | P | 0.009 | 0.054 | 0.642 | 0.870 | 0.421 | 0.461 | P |

TABLE 7-continued

| | Normal Controls | | | | | | Relative Controls | | | | | | |
|---|---|---|---|---|---|---|---|---|---|---|---|---|---|
| Sample | CEA-CAM4 | LAMP1 | PLA-2G7 | PLAC8 | External Controls | Status | CEA-CAM4/ LAMP1 pVal | CEA-CAM4/ PLAC8 pVal | CEA-CAM4/ PLA2G7 pVal | LAMP1/ PLAC8 pVal | LAMP1/ PLA2G7 pVal | PLAC8/ PLA2G7 pVal | Status |
| 2156857 | 22.4 | 23.5 | 27.7 | 20.7 | P | P | 0.553 | 0.753 | 0.893 | 0.925 | 0.660 | 0.762 | P |
| 3222786 | 22.9 | 24.0 | 27.4 | 20.9 | P | P | 0.622 | 0.586 | 0.770 | 0.824 | 0.946 | 0.945 | P |
| 3008502 | 23.1 | 24.4 | 28.1 | 19.3 | P | P | 0.749 | 0.047 | 0.950 | 0.059 | 0.927 | 0.263 | P |
| 3007162 | 23.4 | 25.9 | 28.1 | 23.0 | P | P | 0.335 | 0.536 | 0.845 | 0.969 | 0.490 | 0.593 | P |
| 3173057 | 24.3 | 24.8 | 31.1 | 21.7 | P | P | 0.213 | 0.320 | 0.366 | 0.875 | 0.112 | 0.172 | P |
| 3111443 | 21.0 | 23.4 | 28.2 | 19.1 | P | P | 0.353 | 0.625 | 0.265 | 0.233 | 0.463 | 0.211 | P |
| 2671979 | 24.0 | 25.8 | 29.6 | 22.7 | P | P | 0.817 | 0.935 | 0.792 | 0.799 | 0.867 | 0.783 | P |
| 2627904 | 22.8 | 24.7 | 27.6 | 22.0 | P | P | 0.686 | 0.703 | 0.900 | 0.909 | 0.737 | 0.739 | P |
| 2789061 | 22.2 | 25.3 | 29.6 | 24.1 | P | P | 0.074 | 0.016 | 0.210 | 0.204 | 0.649 | 0.735 | P |
| 3269868 | 21.6 | 24.6 | 27.0 | 22.1 | P | P | 0.118 | 0.197 | 0.865 | 0.806 | 0.550 | 0.538 | P |
| 3033996 | 22.4 | 24.5 | 26.8 | 21.4 | P | P | 0.576 | 0.864 | 0.706 | 0.824 | 0.494 | 0.670 | P |
| 2910981 | 23.4 | 27.5 | 29.8 | 24.4 | P | P | 0.005 | 0.095 | 0.503 | 0.815 | 0.505 | 0.684 | P |
| 3018183 | 22.0 | 24.3 | 28.9 | 21.1 | P | P | 0.420 | 0.808 | 0.346 | 0.745 | 0.543 | 0.503 | P |
| 3125147 | 23.1 | 24.7 | 27.4 | 22.8 | P | P | 0.981 | 0.485 | 0.687 | 0.467 | 0.657 | 0.447 | P |
| 3129468 | 21.0 | 24.5 | 28.4 | 22.1 | P | P | 0.030 | 0.075 | 0.224 | 0.748 | 0.826 | 0.999 | P |
| 2857601 | 22.5 | 23.8 | 26.8 | 21.9 | P | P | 0.784 | 0.616 | 0.682 | 0.463 | 0.762 | 0.515 | P |
| 2636623 | 25.4 | 27.0 | 31.6 | 24.4 | P | P | 0.953 | 0.806 | 0.558 | 0.826 | 0.549 | 0.719 | P |
| 2781026 | 24.2 | 27.5 | 31.4 | 25.3 | P | P | 0.045 | 0.073 | 0.260 | 0.641 | 0.833 | 0.929 | P |
| 3255360 | 23.1 | 24.7 | 27.4 | 21.5 | P | P | 0.951 | 0.803 | 0.698 | 0.756 | 0.655 | 0.851 | P |
| 3029652 | 23.8 | 26.8 | 27.0 | 22.7 | P | P | 0.115 | 0.966 | 0.313 | 0.273 | 0.062 | 0.370 | P |
| 2912013 | 25.7 | 27.1 | 33.5 | 25.4 | P | P | 0.819 | 0.455 | 0.146 | 0.336 | 0.094 | 0.415 | P |
| 2880471 | 22.9 | 25.3 | 29.5 | 20.8 | P | P | 0.419 | 0.497 | 0.442 | 0.190 | 0.673 | 0.286 | P |
| 3151473 | 22.3 | 23.1 | 25.3 | 20.5 | P | P | 0.369 | 0.646 | 0.276 | 0.873 | 0.472 | 0.504 | P |
| 3131243 | 23.4 | 24.3 | 26.2 | 20.9 | P | P | 0.444 | 0.328 | 0.234 | 0.625 | 0.371 | 0.653 | P |
| 2811174 | 22.3 | 26.2 | 27.9 | 21.9 | P | P | 0.009 | 0.541 | 0.804 | 0.217 | 0.301 | 0.883 | P |
| 2768722 | 24.3 | 25.8 | 29.1 | 21.7 | P | P | 0.953 | 0.324 | 0.895 | 0.314 | 0.911 | 0.639 | P |
| 2601748 | 22.3 | 23.1 | 27.1 | 20.2 | P | P | 0.370 | 0.496 | 0.871 | 0.938 | 0.785 | 0.793 | P |
| 2793139 | 21.2 | 21.4 | 26.5 | 17.9 | P | P | 0.103 | 0.114 | 0.900 | 0.615 | 0.343 | 0.297 | P |
| 175 | 22.8 | 23.6 | 28.7 | 18.0 | P | P | 0.380 | 0.007 | 0.665 | 0.026 | 0.366 | 0.050 | P |
| 1528 | 23.9 | 24.2 | 29.4 | 20.6 | P | P | 0.133 | 0.114 | 0.850 | 0.550 | 0.342 | 0.273 | P |
| 763 | 21.6 | 22.4 | 23.6 | 19.4 | P | P | 0.402 | 0.467 | 0.104 | 0.866 | 0.185 | 0.330 | P |
| 2449113 | 23.7 | 25.2 | 28.5 | 22.7 | P | P | 0.922 | 0.865 | 0.902 | 0.801 | 0.934 | 0.836 | P |
| 1239 | 23.7 | 25.9 | 27.6 | 23.1 | P | P | 0.508 | 0.631 | 0.530 | 0.974 | 0.315 | 0.409 | P |
| 2240 | 20.9 | 25.2 | 30.4 | 19.5 | P | P | 0.002 | 0.865 | 0.021 | 0.016 | 0.343 | 0.036 | P |
| 1894 | 23.3 | 25.5 | 27.6 | 23.2 | P | P | 0.475 | 0.390 | 0.691 | 0.690 | 0.434 | 0.395 | P |
| 1143 | 23.8 | 25.6 | 30.4 | 20.3 | P | P | 0.855 | 0.086 | 0.445 | 0.049 | 0.466 | 0.094 | P |
| 2888477 | 21.3 | 23.4 | 28.7 | 19.6 | P | P | 0.591 | 0.678 | 0.228 | 0.406 | 0.305 | 0.199 | P |
| 2786127 | 22.2 | 23.7 | 27.0 | 20.8 | P | P | 0.920 | 0.894 | 0.871 | 0.944 | 0.901 | 0.951 | P |
| 1782 | 26.3 | 25.0 | 30.0 | 21.2 | P | P | 0.001 | 0.003 | 0.492 | 0.443 | 0.376 | 0.255 | P |
| 2774321 | 24.8 | 26.2 | 31.1 | 19.8 | P | P | 0.887 | 0.005 | 0.509 | 0.004 | 0.435 | 0.025 | P |
| 2512541 | 21.6 | 23.6 | 27.8 | 18.1 | P | P | 0.612 | 0.089 | 0.571 | 0.029 | 0.723 | 0.135 | P |
| 2109 | 23.1 | 25.3 | 28.1 | 21.4 | P | P | 0.514 | 0.728 | 0.934 | 0.399 | 0.679 | 0.893 | P |
| 2005 | 22.1 | 24.2 | 27.8 | 21.7 | P | P | 0.543 | 0.518 | 0.768 | 0.803 | 0.989 | 0.899 | P |
| 1145 | 22.8 | 25.6 | 31.0 | 19.3 | P | P | 0.168 | 0.088 | 0.097 | 0.005 | 0.275 | 0.015 | P |
| 2545687 | 19.7 | 21.6 | 28.4 | 19.0 | P | P | 0.748 | 0.710 | 0.061 | 0.869 | 0.064 | 0.161 | P |
| 1824 | 26.1 | 25.2 | 30.0 | 21.0 | P | P | 0.004 | 0.003 | 0.539 | 0.266 | 0.443 | 0.217 | P |
| 554 | 22.3 | 22.6 | 25.8 | 19.1 | P | P | 0.150 | 0.131 | 0.405 | 0.572 | 0.860 | 0.864 | P |
| 2152399 | 25.2 | 25.0 | 31.4 | 20.1 | P | P | 0.047 | 0.003 | 0.573 | 0.083 | 0.111 | 0.025 | P |
| 1630 | 23.9 | 24.9 | 26.2 | 23.0 | P | P | 0.499 | 0.756 | 0.146 | 0.412 | 0.221 | 0.150 | P |
| 2089 | 22.5 | 24.3 | 28.3 | 20.3 | P | P | 0.812 | 0.467 | 0.732 | 0.343 | 0.803 | 0.468 | P |
| 1914 | 21.0 | 22.0 | 25.5 | 18.5 | P | P | 0.519 | 0.346 | 0.774 | 0.591 | 0.990 | 0.758 | P |
| 1189 | 20.9 | 24.5 | 28.0 | 20.3 | P | P | 0.024 | 0.613 | 0.289 | 0.275 | 0.989 | 0.538 | P |
| 2677542 | 25.1 | 26.7 | 30.1 | 22.9 | P | P | 0.989 | 0.472 | 0.952 | 0.438 | 0.943 | 0.710 | P |
| 2073538 | 23.5 | 23.5 | 29.5 | 20.4 | P | P | 0.074 | 0.152 | 0.656 | 0.814 | 0.171 | 0.218 | P |
| 1967 | 21.6 | 23.1 | 26.2 | 19.5 | P | P | 0.905 | 0.533 | 0.810 | 0.563 | 0.842 | 0.873 | P |
| 2550576 | 22.5 | 24.2 | 27.2 | 22.5 | P | P | 0.911 | 0.372 | 0.810 | 0.384 | 0.754 | 0.462 | P |
| 438 | 22.7 | 22.3 | 26.9 | 18.0 | P | P | 0.024 | 0.008 | 0.659 | 0.241 | 0.514 | 0.240 | P |
| 1550 | 25.1 | 26.0 | 30.1 | 23.2 | P | P | 0.420 | 0.635 | 0.970 | 0.938 | 0.718 | 0.804 | P |
| 2087 | 21.4 | 23.4 | 26.7 | 19.4 | P | P | 0.655 | 0.538 | 0.941 | 0.327 | 0.886 | 0.668 | P |
| 1902 | 22.4 | 24.4 | 26.5 | 21.4 | P | P | 0.591 | 0.820 | 0.619 | 0.884 | 0.423 | 0.573 | P |
| 3485126 | 24.1 | 27.1 | 29.8 | 23.9 | P | P | 0.108 | 0.421 | 0.720 | 0.761 | 0.678 | 0.868 | P |
| 1957 | 23.8 | 24.5 | 28.6 | 20.7 | P | P | 0.306 | 0.138 | 0.848 | 0.400 | 0.761 | 0.477 | P |
| 278 | 24.3 | 25.4 | 31.7 | 21.3 | P | P | 0.528 | 0.155 | 0.247 | 0.289 | 0.120 | 0.066 | P |
| 2276373 | 23.6 | 24.2 | 28.4 | 21.0 | P | P | 0.312 | 0.297 | 0.904 | 0.705 | 0.708 | 0.609 | P |
| 2318175 | 21.7 | 23.9 | 28.5 | 21.0 | P | P | 0.485 | 0.699 | 0.369 | 0.925 | 0.538 | 0.584 | P |
| 2079564 | 23.4 | 24.3 | 27.6 | 18.0 | P | P | 0.426 | 0.001 | 0.647 | 0.005 | 0.925 | 0.136 | P |
| 2295511 | 26.3 | 26.1 | 29.3 | 22.7 | P | P | 0.041 | 0.063 | 0.274 | 0.612 | 0.875 | 0.877 | P |
| 2495 | 23.5 | 25.5 | 27.0 | 21.3 | P | P | 0.575 | 0.466 | 0.420 | 0.237 | 0.252 | 0.791 | P |
| 1837 | 25.5 | 26.9 | 32.1 | 23.3 | P | P | 0.924 | 0.634 | 0.346 | 0.564 | 0.335 | 0.273 | P |
| 1223 | 24.8 | 26.3 | 28.9 | 23.1 | P | P | 0.934 | 0.719 | 0.575 | 0.747 | 0.576 | 0.786 | P |
| 2193 | 25.1 | 26.4 | 31.2 | 23.4 | P | P | 0.762 | 0.700 | 0.593 | 0.849 | 0.468 | 0.490 | P |
| 2045301 | 25.0 | 25.3 | 31.1 | 21.0 | P | P | 0.176 | 0.041 | 0.570 | 0.229 | 0.199 | 0.089 | P |
| 2469217 | 21.2 | 22.5 | 27.3 | 19.9 | P | P | 0.681 | 0.933 | 0.630 | 0.835 | 0.470 | 0.641 | P |

TABLE 7-continued

|  | Normal Controls | | | | | | Relative Controls | | | | | | |
| --- | --- | --- | --- | --- | --- | --- | --- | --- | --- | --- | --- | --- | --- |
| Sample | CEA-CAM4 | LAMP1 | PLA-2G7 | PLAC8 | External Controls | Status | CEA-CAM4/ LAMP1 pVal | CEA-CAM4/ PLAC8 pVal | CEA-CAM4/ PLA2G7 pVal | LAMP 1/ PLAC8 pVal | LAMP 1/ PLA2G7 pVal | PLAC8/ PLA2G7 pVal | Status |
| 2351284 | 20.9 | 21.9 | 22.4 | 19.2 | P | P | 0.466 | 0.733 | 0.057 | 0.870 | 0.094 | 0.150 | P |
| 2712378 | 21.6 | 23.2 | 26.5 | 19.3 | P | P | 0.949 | 0.415 | 0.921 | 0.411 | 0.941 | 0.692 | P |
| 2739656 | 24.6 | 26.2 | 29.0 | 23.6 | P | P | 0.984 | 0.856 | 0.704 | 0.858 | 0.676 | 0.664 | P |
| 2462 | 20.0 | 24.1 | 27.7 | 21.5 | P | P | 0.006 | 0.041 | 0.186 | 0.834 | 0.953 | 0.945 | P |
| 1835 | 22.1 | 23.5 | 26.6 | 21.1 | P | P | 0.848 | 0.837 | 0.767 | 0.720 | 0.824 | 0.705 | P |
| 1400 | 22.0 | 23.9 | 25.0 | 20.7 | P | P | 0.694 | 0.990 | 0.286 | 0.766 | 0.180 | 0.361 | P |
| 2662486 | 24.7 | 24.7 | 27.6 | 22.1 | P | P | 0.071 | 0.279 | 0.247 | 0.879 | 0.732 | 0.719 | P |
| 2654139 | 20.8 | 22.4 | 24.0 | 20.1 | P | P | 0.905 | 0.679 | 0.339 | 0.723 | 0.278 | 0.284 | P |
| 2309104 | 23.0 | 25.8 | 28.6 | 20.0 | P | P | 0.192 | 0.182 | 0.797 | 0.018 | 0.709 | 0.312 | P |
| 1426 | 23.4 | 24.1 | 28.9 | 21.7 | P | P | 0.329 | 0.767 | 0.810 | 0.696 | 0.457 | 0.702 | P |
| 2661366 | 26.4 | 25.9 | 29.9 | 22.2 | P | P | 0.018 | 0.022 | 0.410 | 0.466 | 0.765 | 0.519 | P |
| 2143801 | 25.0 | 25.6 | 28.9 | 22.6 | P | P | 0.255 | 0.363 | 0.542 | 0.884 | 0.931 | 0.991 | P |
| 1717 | 23.3 | 24.7 | 28.5 | 20.9 | P | P | 0.849 | 0.380 | 0.943 | 0.424 | 0.864 | 0.561 | P |
| 1863 | 23.7 | 25.6 | 26.9 | 22.4 | P | P | 0.771 | 0.970 | 0.310 | 0.801 | 0.216 | 0.392 | P |
| 1218 | 24.9 | 26.4 | 29.3 | 23.1 | P | P | 0.870 | 0.622 | 0.689 | 0.683 | 0.728 | 0.957 | P |
| 2566446 | 21.9 | 22.0 | 25.5 | 20.0 | P | P | 0.080 | 0.589 | 0.431 | 0.490 | 0.979 | 0.718 | P |
| 2355070 | 23.3 | 26.3 | 30.2 | 20.0 | P | P | 0.105 | 0.111 | 0.325 | 0.004 | 0.803 | 0.073 | P |
| 2512233 | 24.8 | 26.2 | 31.2 | 20.6 | P | P | 0.808 | 0.023 | 0.495 | 0.024 | 0.393 | 0.053 | P |
| 2317 | 22.1 | 25.1 | 25.8 | 21.9 | P | P | 0.111 | 0.428 | 0.489 | 0.757 | 0.124 | 0.287 | P |
| 2286 | 22.9 | 25.7 | 28.6 | 22.3 | P | P | 0.179 | 0.636 | 0.761 | 0.639 | 0.731 | 0.986 | P |
| 1128 | 21.6 | 25.0 | 27.7 | 22.3 | P | P | 0.037 | 0.131 | 0.605 | 0.923 | 0.626 | 0.656 | P |
| 1536 | 19.4 | 23.4 | 24.9 | 17.3 | P | P | 0.008 | 0.492 | 0.840 | 0.008 | 0.266 | 0.561 | P |
| 2257043 | 21.1 | 22.5 | 27.0 | 17.7 | P | P | 0.786 | 0.098 | 0.660 | 0.117 | 0.544 | 0.174 | P |
| 2231993 | 22.7 | 23.1 | 25.9 | 20.1 | P | P | 0.190 | 0.287 | 0.319 | 0.852 | 0.677 | 0.817 | P |
| 1521 | 25.5 | 24.8 | 27.5 | 22.3 | P | P | 0.011 | 0.142 | 0.111 | 0.785 | 0.657 | 0.611 | P |
| 220 | 24.1 | 24.8 | 27.5 | 20.0 | P | P | 0.338 | 0.027 | 0.360 | 0.097 | 0.614 | 0.606 | P |
| 893 | 23.8 | 24.8 | 28.5 | 20.8 | P | P | 0.490 | 0.177 | 0.826 | 0.348 | 0.913 | 0.543 | P |
| 2138 | 23.6 | 25.5 | 30.3 | 23.0 | P | P | 0.705 | 0.595 | 0.389 | 0.770 | 0.462 | 0.667 | P |
| 2076 | 22.3 | 24.3 | 25.8 | 22.6 | P | P | 0.660 | 0.250 | 0.400 | 0.364 | 0.261 | 0.159 | P |
| 1142 | 23.1 | 26.8 | 28.7 | 24.6 | P | P | 0.016 | 0.036 | 0.794 | 0.632 | 0.355 | 0.312 | P |
| 1539 | 22.8 | 24.3 | 30.3 | 20.8 | P | P | 0.923 | 0.552 | 0.211 | 0.572 | 0.165 | 0.152 | P |
| 349 | 21.9 | 23.6 | 26.2 | 20.1 | P | P | 0.887 | 0.652 | 0.672 | 0.560 | 0.599 | 0.921 | P |
| 1669 | 26.0 | 25.8 | 28.1 | 23.6 | P | P | 0.042 | 0.367 | 0.116 | 0.610 | 0.501 | 0.410 | P |
| 2740095 | 21.3 | 24.7 | 28.6 | 22.1 | P | P | 0.050 | 0.119 | 0.269 | 0.805 | 0.833 | 0.974 | P |
| 2855706 | 21.2 | 22.8 | 26.8 | 19.9 | P | P | 0.962 | 0.982 | 0.793 | 0.954 | 0.796 | 0.810 | P |
| 2259 | 20.6 | 22.1 | 27.0 | 16.6 | P | P | 0.908 | 0.032 | 0.502 | 0.027 | 0.436 | 0.064 | P |
| 2593636 | 22.0 | 22.6 | 28.3 | 17.2 | P | P | 0.230 | 0.006 | 0.531 | 0.042 | 0.204 | 0.032 | P |
| 2937810 | 22.8 | 24.3 | 30.0 | 20.8 | P | P | 0.862 | 0.540 | 0.270 | 0.597 | 0.204 | 0.189 | P |
| 2792222 | 24.2 | 25.4 | 29.2 | 23.2 | P | P | 0.656 | 0.846 | 0.931 | 0.596 | 0.896 | 0.850 | P |
| 1853 | 22.2 | 23.3 | 26.3 | 19.6 | P | P | 0.582 | 0.312 | 0.639 | 0.496 | 0.818 | 0.847 | P |
| 2802981 | 22.6 | 25.2 | 28.1 | 19.1 | P | P | 0.225 | 0.092 | 0.797 | 0.008 | 0.743 | 0.223 | P |
| 2060742 | 21.4 | 22.3 | 25.5 | 18.8 | P | P | 0.406 | 0.277 | 0.584 | 0.577 | 0.863 | 0.865 | P |
| 820 | 20.8 | 21.2 | 25.5 | 17.8 | P | P | 0.213 | 0.181 | 0.866 | 0.599 | 0.660 | 0.518 | P |
| 922 | 21.7 | 22.1 | 28.0 | 18.7 | P | P | 0.180 | 0.158 | 0.556 | 0.592 | 0.194 | 0.179 | P |
| 2319 | 25.9 | 25.8 | 34.3 | 21.2 | P | P | 0.059 | 0.008 | 0.088 | 0.143 | 0.006 | 0.002 | P |
| 1532 | 23.9 | 25.9 | 30.4 | 24.1 | P | P | 0.659 | 0.300 | 0.474 | 0.432 | 0.583 | 0.995 | P |
| 632 | 24.4 | 25.4 | 31.0 | 23.7 | P | P | 0.483 | 0.734 | 0.438 | 0.384 | 0.238 | 0.640 | P |
| 2226 | 24.1 | 25.1 | 29.6 | 22.4 | P | P | 0.507 | 0.721 | 0.830 | 0.920 | 0.575 | 0.692 | P |
| 2332187 | 21.5 | 23.7 | 26.8 | 18.3 | P | P | 0.497 | 0.134 | 0.915 | 0.037 | 0.822 | 0.328 | P |
| 2423724 | 23.7 | 26.1 | 29.6 | 20.9 | P | P | 0.391 | 0.222 | 0.692 | 0.055 | 0.998 | 0.287 | P |
| 2269 | 25.5 | 26.5 | 29.1 | 23.1 | P | P | 0.574 | 0.381 | 0.455 | 0.598 | 0.602 | 0.899 | P |
| 893_1 | 24.8 | 26.3 | 28.5 | 21.0 | P | P | 0.878 | 0.045 | 0.455 | 0.043 | 0.468 | 0.589 | P |
| 1016 | 24.8 | 24.9 | 26.8 | 21.4 | P | P | 0.113 | 0.106 | 0.107 | 0.565 | 0.347 | 0.662 | P |
| 2914265 | 24.4 | 25.8 | 28.7 | 21.1 | P | P | 0.912 | 0.130 | 0.687 | 0.125 | 0.705 | 0.585 | P |
| 2235173 | 23.6 | 24.5 | 31.8 | 19.8 | P | P | 0.454 | 0.055 | 0.098 | 0.133 | 0.032 | 0.010 | P |
| 615 | 24.3 | 25.3 | 30.3 | 23.8 | P | P | 0.525 | 0.592 | 0.629 | 0.302 | 0.404 | 0.920 | P |
| 2555715 | 24.5 | 26.5 | 30.7 | 21.5 | P | P | 0.664 | 0.173 | 0.557 | 0.077 | 0.679 | 0.189 | P |
| 3032 | 25.0 | 26.3 | 31.2 | 21.1 | P | P | 0.725 | 0.036 | 0.561 | 0.048 | 0.424 | 0.082 | P |
| 2533160 | 23.9 | 26.6 | 31.9 | 24.4 | P | P | 0.203 | 0.181 | 0.138 | 0.614 | 0338 | 0.623 | P |
| 2108553 | 25.0 | 25.6 | 30.4 | 21.1 | P | P | 0.280 | 0.039 | 0.889 | 0.157 | 0.491 | 0.181 | P |
| 2855460 | 24.3 | 25.6 | 26.6 | 21.5 | P | P | 0.718 | 0.223 | 0.149 | 0.299 | 0.171 | 0.598 | P |
| 2505890 | 25.3 | 26.9 | 30.1 | 21.5 | P | P | 0.945 | 0.046 | 0.851 | 0.037 | 0.867 | 0.308 | P |
| 438_1 | 24.9 | 24.5 | 28.7 | 21.4 | P | P | 0.028 | 0.089 | 0.522 | 0.820 | 0.685 | 0.651 | P |
| 1670 | 24.1 | 24.6 | 29.1 | 21.7 | P | P | 0.196 | 0.344 | 0.939 | 0.941 | 0.574 | 0.622 | P |
| 2895821 | 26.2 | 26.8 | 30.2 | 23.4 | P | P | 0.271 | 0.241 | 0.563 | 0.651 | 0.942 | 0.847 | P |
| 382 | 24.8 | 24.3 | 27.6 | 22.3 | P | P | 0.020 | 0.322 | 0.222 | 0.533 | 0.878 | 0.639 | P |
| 923 | 23.4 | 24.2 | 26.0 | 19.6 | P | P | 0.406 | 0.051 | 0.188 | 0.138 | 0.318 | 0.986 | P |
| 739 | 20.6 | 21.3 | 25.1 | 17.2 | P | P | 0.319 | 0.109 | 0.775 | 0.324 | 0.850 | 0.484 | P |
| 1023 | 25.4 | 25.7 | 29.0 | 21.7 | P | P | 0.127 | 0.058 | 0.431 | 0.358 | 0.932 | 0.659 | P |
| 2197135 | 26.2 | 26.7 | 33.0 | 22.2 | P | P | 0.234 | 0.033 | 0.365 | 0.160 | 0.117 | 0.041 | P |
| 2442 | 23.8 | 24.7 | 29.8 | 20.3 | P | P | 0.421 | 0.075 | 0.645 | 0.187 | 0.370 | 0.147 | P |

TABLE 7-continued

| | Normal Controls | | | | | Relative Controls | | | | | | |
|---|---|---|---|---|---|---|---|---|---|---|---|---|
| Sample | CEA-CAM4 | LAMP1 | PLA2G7 | PLAC8 | External Controls | Status | CEA-CAM4/LAMP1 pVal | CEA-CAM4/PLAC8 pVal | CEA-CAM4/PLA2G7 pVal | LAMP1/PLAC8 pVal | LAMP1/PLA2G7 pVal | PLAC8/PLA2G7 pVal | Status |
| 3245 | 23.0 | 25.3 | 29.1 | 21.8 | P | P | 0.486 | 0.967 | 0.607 | 0.584 | 0.838 | 0.640 | P |
| 2214618 | 22.5 | 23.5 | 27.9 | 20.1 | P | P | 0.502 | 0.375 | 0.865 | 0.645 | 0.605 | 0.502 | P |
| 2923104 | 25.6 | 28.3 | 31.1 | 24.1 | P | P | 0.216 | 0.829 | 0.836 | 0.260 | 0.693 | 0.759 | P |
| 2577185 | 25.3 | 25.9 | 26.8 | 23.8 | P | P | 0.229 | 0.839 | 0.058 | 0.513 | 0.152 | 0.130 | P |
| 2691741 | 25.6 | 25.9 | 29.1 | 23.6 | P | P | 0.147 | 0.583 | 0.394 | 0.642 | 0.848 | 0.681 | P |
| 2067 | 26.1 | 27.6 | 29.9 | 23.7 | P | P | 0.940 | 0.360 | 0.497 | 0.357 | 0.490 | 0.964 | P |
| 2866838 | 24.6 | 27.4 | 29.7 | 24.1 | P | P | 0.193 | 0.592 | 0.993 | 0.711 | 0.510 | 0.746 | P |
| 651 | 24.2 | 25.8 | 25.2 | 19.1 | P | P | 0.979 | 0.003 | 0.033 | 0.002 | 0.023 | 0.935 | P |
| 784 | 22.8 | 24.4 | 27.8 | 21.8 | P | P | 0.991 | 0.854 | 0.966 | 0.851 | 0.959 | 0.884 | P |
| 2538 | 22.5 | 22.5 | 24.8 | 20.5 | P | P | 0.072 | 0.530 | 0.135 | 0.526 | 0.479 | 0.357 | P |
| 243 | 22.6 | 22.8 | 25.3 | 18.1 | P | P | 0.134 | 0.014 | 0.210 | 0.126 | 0.551 | 0.713 | P |
| 2024940 | 23.7 | 26.4 | 30.3 | 25.1 | P | P | 0.195 | 0.043 | 0.428 | 0.222 | 0.839 | 0.608 | P |
| 2473497 | 25.3 | 26.5 | 29.8 | 21.3 | P | P | 0.657 | 0.037 | 0.776 | 0.058 | 0.934 | 0.325 | P |
| 2727912 | 24.6 | 25.6 | 27.0 | 21.1 | P | P | 0.569 | 0.093 | 0.161 | 0.168 | 0.222 | 0.828 | P |
| 687 | 24.3 | 25.5 | 31.0 | 20.4 | P | P | 0.662 | 0.039 | 0.400 | 0.059 | 0.262 | 0.051 | P |
| 160 | 24.3 | 24.8 | 29.0 | 21.2 | P | P | 0.245 | 0.167 | 0.858 | 0.527 | 0.698 | 0.507 | P |
| 670 | 27.3 | 27.5 | 29.9 | 24.9 | P | P | 0.109 | 0.394 | 0.200 | 0.802 | 0.565 | 0.547 | P |
| 2629101 | 26.5 | 26.9 | 30.3 | 24.4 | P | P | 0.186 | 0.526 | 0.513 | 0.778 | 0.967 | 0.850 | P |
| 2532 | 23.1 | 24.3 | 28.2 | 17.7 | P | P | 0.706 | 0.001 | 0.999 | 0.002 | 0.852 | 0.060 | P |
| 2071896 | 24.0 | 25.9 | 29.8 | 20.8 | P | P | 0.713 | 0.132 | 0.725 | 0.061 | 0.846 | 0.233 | P |
| 2788747 | 25.9 | 27.6 | 29.8 | 22.6 | P | P | 0.903 | 0.108 | 0.550 | 0.072 | 0.482 | 0.665 | P |
| 1611 | 22.8 | 24.3 | 27.6 | 17.9 | P | P | 0.919 | 0.005 | 0.904 | 0.004 | 0.937 | 0.121 | P |
| 1248 | 21.8 | 23.1 | 28.7 | 18.9 | P | P | 0.738 | 0.215 | 0.346 | 0.280 | 0.239 | 0.122 | P |
| 790 | 23.6 | 23.7 | 27.3 | 19.4 | P | P | 0.091 | 0.021 | 0.454 | 0.216 | 0.969 | 0.474 | P |
| 1079 | 24.3 | 25.2 | 30.3 | 24.0 | P | P | 0.483 | 0.438 | 0.624 | 0.182 | 0.381 | 0.972 | P |
| 3063 | 24.7 | 25.9 | 29.9 | 20.2 | P | P | 0.651 | 0.013 | 0.947 | 0.020 | 0.767 | 0.127 | P |
| 3117 | 25.0 | 25.3 | 29.7 | 20.8 | P | P | 0.143 | 0.024 | 0.865 | 0.176 | 0.583 | 0.234 | P |
| 852 | 25.5 | 26.2 | 29.4 | 22.6 | P | P | 0.351 | 0.223 | 0.527 | 0.532 | 0.831 | 0.862 | P |
| 2295 | 23.8 | 23.8 | 25.1 | 20.4 | P | P | 0.072 | 0.096 | 0.046 | 0.637 | 0.214 | 0.460 | P |
| 2912 | 25.1 | 26.1 | 31.0 | 20.9 | P | P | 0.488 | 0.022 | 0.672 | 0.053 | 0.423 | 0.086 | P |
| 3137 | 24.9 | 25.8 | 29.1 | 22.5 | P | P | 0.398 | 0.359 | 0.621 | 0.715 | 0.914 | 0.908 | P |
| 1206 | 22.0 | 22.5 | 25.0 | 20.1 | P | P | 0.200 | 0.581 | 0.271 | 0.734 | 0.589 | 0.533 | P |
| 2974887 | 23.0 | 24.6 | 29.5 | 20.8 | P | P | 0.972 | 0.464 | 0.446 | 0.450 | 0.404 | 0.275 | P |
| 2526 | 23.1 | 25.3 | 30.7 | 21.6 | P | P | 0.495 | 0.809 | 0.190 | 0.452 | 0.286 | 0.202 | P |
| 3044 | 22.0 | 22.8 | 27.0 | 20.1 | P | P | 0.336 | 0.586 | 0.960 | 0.907 | 0.669 | 0.780 | P |
| 2907847 | 22.8 | 23.6 | 26.6 | 19.1 | P | P | 0.337 | 0.060 | 0.476 | 0.191 | 0.775 | 0.620 | P |
| 3210 | 23.3 | 25.0 | 26.2 | 22.1 | P | P | 0.913 | 0.994 | 0.235 | 0.943 | 0.184 | 0.303 | P |
| 3199 | 25.4 | 25.1 | 30.0 | 21.4 | P | P | 0.033 | 0.039 | 0.801 | 0.508 | 0.429 | 0.316 | P |
| 3318 | 26.5 | 27.4 | 32.4 | 22.5 | P | P | 0.431 | 0.037 | 0.659 | 0.098 | 0.386 | 0.106 | P |
| 3111 | 24.5 | 26.1 | 29.1 | 21.3 | P | P | 0.990 | 0.140 | 0.803 | 0.113 | 0.784 | 0.511 | P |
| 3210_1 | 26.4 | 26.7 | 29.5 | 23.2 | P | P | 0.160 | 0.129 | 0.310 | 0.547 | 0.698 | 0.983 | P |
| 3088 | 24.0 | 24.8 | 26.9 | 20.0 | P | P | 0.398 | 0.037 | 0.246 | 0.107 | 0.410 | 0.818 | P |
| 2912876 | 27.2 | 28.4 | 32.7 | 26.0 | P | P | 0.635 | 0.995 | 0.831 | 0.726 | 0.642 | 0.857 | P |
| 2825793 | 25.6 | 25.4 | 30.2 | 22.1 | P | P | 0.044 | 0.083 | 0.769 | 0.695 | 0.491 | 0.440 | P |
| 2761 | 20.7 | 21.2 | 25.9 | 17.4 | P | P | 0.233 | 0.127 | 0.936 | 0.444 | 0.496 | 0.331 | P |
| 2440 | 22.1 | 22.4 | 26.1 | 20.0 | P | P | 0.128 | 0.473 | 0.542 | 0.737 | 0.917 | 0.919 | P |

Table 8 shows raw data results for 2 samples (of 546) that failed both the Normal controls and Relative controls method.

TABLE 8

| | Normal Controls | | | | | Relative Controls | | | | | | |
|---|---|---|---|---|---|---|---|---|---|---|---|---|
| Sample | CEA-CAM4 | LAMP1 | PLA2G7 | PLAC8 | Status | CEA-CAM4/LAMP1 pVal | CEA-CAM4/PLAC8 pVal | CEA-CAM4/PLA2G7 pVal | LAMP1/PLAC8 pVal | LAMP1/PLA2G7 pVal | PLAC8/PLA2G7 pVal | Status |
| 2712753 | 21.30 | 22.23 | 36.06 | 18.67 | F | 0.460 | 0.286 | 0.000 | 0.547 | 0.000 | 0.000 | F |
| 2023537 | 25.29 | 25.22 | 37.02 | 21.26 | F | 0.062 | 0.032 | 0.001 | 0.351 | 0.000 | 0.000 | F |

Table 9 shows raw data results for 26 samples (of 546) that failed both the Normal controls but passed the Relative controls method.

TABLE 9

| | Normal Controls | | | | | | Relative Controls | | | | | | |
|---|---|---|---|---|---|---|---|---|---|---|---|---|---|
| Sample | CEA-CAM4 | LAMP1 | PLA2G7 | PLAC8 | External Control | Status | CEA-CAM4/ LAMP1 pVal | CEA-CAM4/ PLAC8 pVal | CEA-CAM4/ PLA2G7 pVal | LAMP1/ PLAC8 pVal | LAMP1/ PLA2G7 pVal | PLAC8/ PLA2G7 pVal | Status |
| 6759 | 22.50 | 23.66 | 26.51 | 22.02 | F | F | 0.629 | 0.566 | 0.570 | 0.337 | 0.712 | 0.407 | P |
| 6769 | 23.89 | 24.05 | 27.32 | 21.34 | F | F | 0.107 | 0.317 | 0.385 | 0.921 | 0.897 | 0.873 | P |
| 6789 | 22.52 | 23.26 | 26.83 | 21.76 | F | F | 0.338 | 0.717 | 0.681 | 0.280 | 0.971 | 0.569 | P |
| 6812 | 21.97 | 23.71 | 26.12 | 22.12 | F | F | 0.864 | 0.290 | 0.622 | 0.315 | 0.539 | 0.293 | P |
| 6829 | 22.04 | 23.95 | 26.75 | 22.49 | F | F | 0.721 | 0.197 | 0.842 | 0.264 | 0.695 | 0.350 | P |
| 6834 | 21.29 | 23.97 | 29.11 | 20.88 | F | F | 0.221 | 0.526 | 0.153 | 0.834 | 0.356 | 0.391 | P |
| 6836 | 21.20 | 23.52 | 27.88 | 20.38 | F | F | 0.412 | 0.753 | 0.405 | 0.796 | 0.627 | 0.594 | P |
| 6843 | 21.42 | 22.58 | 24.07 | 20.46 | F | F | 0.632 | 0.833 | 0.200 | 0.568 | 0.256 | 0.218 | P |
| 6852 | 21.90 | 24.03 | 26.33 | 22.64 | F | F | 0.546 | 0.132 | 0.726 | 0.242 | 0.498 | 0.233 | P |
| 6853 | 23.87 | 24.49 | 25.97 | 21.25 | F | F | 0.273 | 0.289 | 0.117 | 0.736 | 0.256 | 0.467 | P |
| 6870 | 24.10 | 25.35 | 28.17 | 22.11 | F | F | 0.702 | 0.564 | 0.593 | 0.735 | 0.702 | 0.904 | P |
| IXP-109 | 22.61 | 24.05 | 27.79 | 20.50 | F | F | 0.866 | 0.503 | 0.961 | 0.554 | 0.891 | 0.661 | P |
| ixp-136 | 23.04 | 24.41 | 25.56 | 19.59 | F | F | 0.808 | 0.090 | 0.178 | 0.103 | 0.185 | 0.871 | P |
| IXP-138 | 23.47 | 24.12 | 28.75 | 20.79 | F | F | 0.291 | 0.272 | 0.920 | 0.683 | 0.526 | 0.461 | P |
| IXP-139 | 22.12 | 23.35 | 26.09 | 20.97 | F | F | 0.688 | 0.947 | 0.555 | 0.718 | 0.665 | 0.583 | P |
| IXP-140 | 21.48 | 23.36 | 27.55 | 22.04 | F | F | 0.744 | 0.168 | 0.607 | 0.218 | 0.697 | 0.711 | P |
| IXP-141 | 23.95 | 25.12 | 27.55 | 20.63 | F | F | 0.637 | 0.111 | 0.434 | 0.174 | 0.546 | 0.789 | P |
| IXP-143 | 23.24 | 24.40 | 26.09 | 22.16 | F | F | 0.635 | 0.903 | 0.240 | 0.635 | 0.306 | 0.277 | P |
| IXP-144 | 22.52 | 24.89 | 27.06 | 22.01 | F | F | 0.378 | 0.579 | 0.774 | 0.963 | 0.455 | 0.564 | P |
| IXP-146 | 22.05 | 24.19 | 27.20 | 21.35 | F | F | 0.531 | 0.682 | 0.974 | 0.986 | 0.781 | 0.830 | P |
| IXP-147 | 24.99 | 25.72 | 26.24 | 21.69 | F | F | 0.332 | 0.115 | 0.044 | 0.329 | 0.094 | 0.420 | P |
| IXP-148 | 21.46 | 23.18 | 25.75 | 21.80 | F | F | 0.887 | 0.228 | 0.674 | 0.237 | 0.602 | 0.282 | P |
| IXP-149 | 23.67 | 24.19 | 25.50 | 22.14 | F | F | 0.226 | 0.821 | 0.087 | 0.526 | 0.218 | 0.179 | P |
| 6869 | 31.60 | 35.99 | 37.22 | 33.46 | P | F | 0.002 | 0.018 | 0.784 | 0.809 | 0.201 | 0.245 | P |
| IXP-128 | 31.87 | 33.39 | 38.03 | 28.11 | P | F | 0.940 | 0.053 | 0.578 | 0.045 | 0.526 | 0.105 | P |
| 1357 | 27.27 | 27.05 | 35.06 | 22.12 | P | F | 0.042 | 0.003 | 0.157 | 0.085 | 0.011 | 0.003 | P |

Table 10 shows raw data results for 13 samples (of 546) that passed the Normal controls but failed the Relative controls method.

TABLE 10

| | Normal Controls | | | | | | Relative Controls | | | | | | |
|---|---|---|---|---|---|---|---|---|---|---|---|---|---|
| Sample | CEA-CAM4 | LAMP1 | PLA2G7 | PLAC8 | External Control | Status | CEA-CAM4/ LAMP1 pVal | CEA-CAM4/ PLAC8 pVal | CEA-CAM4/ PLA2G7 pVal | LAMP1/ PLAC8 pVal | LAMP1/ PLA2G7 pVal | PLAC8/ PLA2G7 pVal | Status |
| 2400065 | 21.11 | 27.01 | 29.58 | 23.37 | P | P | 0.000 | 0.008 | 0.077 | 0.508 | 0.600 | 0.956 | F |
| 2491930 | 21.48 | 26.42 | 28.04 | 23.01 | P | P | 0.000 | 0.035 | 0.443 | 0.628 | 0.287 | 0.557 | F |
| 2283614 | 22.05 | 26.95 | 30.13 | 24.69 | P | P | 0.000 | 0.003 | 0.118 | 0.651 | 0.852 | 0.688 | F |
| 2541845 | 20.28 | 25.17 | 27.53 | 22.41 | P | P | 0.000 | 0.010 | 0.259 | 0.956 | 0.521 | 0.585 | F |
| 3787 | 26.15 | 30.73 | 31.07 | 21.69 | P | P | 0.001 | 0.013 | 0.929 | 0.000 | 0.076 | 0.166 | F |
| 2781056 | 22.21 | 27.49 | 29.08 | 24.38 | P | P | 0.000 | 0.009 | 0.352 | 0.818 | 0.283 | 0.461 | F |
| 2636948 | 19.62 | 24.71 | 27.18 | 21.20 | P | P | 0.000 | 0.031 | 0.196 | 0.574 | 0.563 | 0.877 | F |
| 2580739 | 27.27 | 26.55 | 29.78 | 20.66 | P | P | 0.009 | 0.000 | 0.177 | 0.012 | 0.880 | 0.206 | F |
| 1329 | 26.14 | 24.03 | 30.86 | 22.36 | P | P | 0.000 | 0.052 | 0.847 | 0.346 | 0.061 | 0.326 | F |
| 2423113 | 23.90 | 26.72 | 32.41 | 19.80 | P | P | 0.164 | 0.029 | 0.073 | 0.001 | 0.219 | 0.004 | F |
| 2791 | 25.57 | 23.59 | 31.40 | 19.13 | P | P | 0.000 | 0.000 | 0.701 | 0.180 | 0.016 | 0.007 | F |
| 1914 | 24.65 | 26.29 | 29.91 | 17.72 | P | P | 0.958 | 0.000 | 0.933 | 0.000 | 0.948 | 0.008 | F |
| 2452 | 23.48 | 22.98 | 26.30 | 17.56 | P | P | 0.018 | 0.000 | 0.234 | 0.035 | 0.920 | 0.276 | F |

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

Persons skilled in the art will appreciate that numerous variations and modifications will become apparent. All such variations and modifications which become apparent to persons skilled in the art, should be considered to fall within the spirit and scope that the invention broadly appearing before described.

The invention claimed is:

1. A method for validating quantification of biomarker values to ensure each biomarker value is correctly quantified, measured, or calculated, the method including,
   (a) obtaining a blood sample from a human biological subject, the blood sample including nucleic acid gene expression products;
   (b) performing quantitative amplification of the gene expression products in the blood sample;

(c) for at least four gene expression products, determining an amplification amount representing a degree of amplification required to obtain a defined level of the respective gene expression product, each amplification amount corresponding to a respective biomarker value; and (d) in one or more electronic processing devices:
   i) receiving four biomarker values including a biomarker value for each of the at least four gene expression products, wherein each biomarker value is a measurement of a concentration of a nucleic acid respective biomarker in the blood sample from the human biological subject, and the biomarkers being nucleic acid gene expression products, and wherein the at least four gene expression products used for validation are indicative of a likelihood that a biological subject has ipSIRS (infection positive Systemic Inflammatory Response Syndrome), and the four biomarker values include:
      (1) a first biomarker value indicative of a relative concentration of LAMP1 (Lysosomal-associated membrane protein 1);
      (2) a second biomarker value indicative of a relative concentration of CEACAM4 (Carcinoembryonic antigen related cell adhesion molecule 4);
      (3) a third biomarker value indicative of a relative concentration of PLAC8 (Placenta specific 8); and,
      (4) a fourth biomarker value indicative of a relative concentration of PLA2G7 (Phospholipase A2 Group VII);
   ii) calculating:
      (1) a first control value indicative of a ratio of the first and third biomarker values;
      (2) a second control value indicative of a ratio of the first and fourth biomarker values;
      (3) a third control value indicative of a ratio of the second and third biomarker values; and
      (4) a fourth control value indicative of a ratio of the second and fourth biomarker values;
   iii) retrieving a respective control reference for each of the four control values from a database, the control reference being a control value threshold range;
   iv) comparing each control value to a respective control value threshold range, wherein the control value reference range is derived from biomarker values collected from a number of individuals in a sample population using previously defined valid tests and using a computer-implemented classifier algorithm trained on the biomarker values for the sample population;
   v) calculating a p value for each control value based on the comparison;
   vi) determining at least one of the biomarker values to be invalid if any one of the control values has a p value of less than 0.01; and,
   vii) validating quantification of biomarker values to ensure each biomarker value is correctly quantified, measured, or calculated if no biomarker values are invalid, wherein the method is performed without requiring the use of external additional controls, or use of extraneous housekeeping genes.

2. A method according to claim 1, further includes calculating
   a) a fifth control value indicative of a ratio of the first and second biomarker values; and
   b) a sixth control value indicative of a ratio of the third and fourth biomarker values.

3. A method according to claim 1, wherein the ratio of two biomarker values is calculated by subtracting amplification amounts for the respective gene expression products.

4. A method according to claim 1, further includes determining control values including:
   a) a fifth control value using a ratio of first and second biomarker values;
   b) a sixth control value using a ratio of third and fourth biomarker values; and,
   c) controls values calculated using a ratio of measured biomarkers not used in determining an indicator value.

5. A method according to claim 1, wherein the control reference is a control value distribution, and wherein the method includes:
   a) comparing each control value to a respective control value distribution; and,
   b) determining the validity using the results of the comparisons.

6. A method according to claim 1, wherein the sample population is selected from the group consisting of at least one of:
   a) a plurality of individuals of different sexes;
   b) a plurality of individuals of different ethnicities;
   c) a plurality of healthy individuals;
   d) a plurality of individuals suffering from at least one diagnosed medical condition;
   e) a plurality of individuals showing clinical signs of at least one medical condition; and,
   f) first and second groups of individuals, each group of individuals suffering from a respective diagnosed medical condition.

7. A method according to claim 1, wherein the method further includes individuals selected from the group consisting of:
   a) individuals presenting with clinical signs of the at least one medical condition;
   b) individuals diagnosed with the at least one medical condition; and,
   c) healthy individuals.

8. A method according to claim 1, wherein the method further includes, in the one or more processing devices, generating an indicator by:
   a) calculating:
      (i) a first indicator value indicative of a ratio of first and second ones of the four biomarker values; and
      (ii) a second indicator value indicative of a ratio of third and fourth ones of the four biomarker values; and
   (b) combining the first and second indicator values using an additive model.

9. A method according to claim 1, wherein the method further includes:
   a) determining an indicator value;
   b) comparing the indicator value to at least one indicator value range; and,
   c) determining the indicator at least in part using a result of the comparison.

10. A method according to claim 8, wherein the method further includes generating a representation of the indicator.

11. A method according to claim 10, wherein the representation includes:
   a) an alphanumeric indication of the indicator value; and
   b) a graphical indication of a comparison of the indicator value to one or more thresholds.

12. A method according to claim 1, wherein the method further includes:

a) determining a validity probability based on the result of the comparison; and
b) using the validity probability to determine if the biomarker values are valid.

13. A method according to claim 1, wherein the method further includes:
a) determining a control value probability for the comparison of each control value to the respective control reference; and,
b) combining the control value probabilities to determine the validity probability.

14. A method according to claim 1, wherein quantitative amplification of the gene expression products is performed using polymerase chain reaction (PCR).

15. A method according to claim 14, wherein the PCR is quantitative real time PCR (qPCR).

* * * * *